(12) United States Patent
Weuster-Botz et al.

(10) Patent No.: US 10,544,441 B2
(45) Date of Patent: Jan. 28, 2020

(54) METHOD FOR BIOCATALYTIC WHOLE CELL REDUCTION OF DEHYDROCHOLIC ACID COMPOUNDS, AND 7-β-HYDROXYSTEROID DEHYDROGENASE MUTANTS

(71) Applicant: Pharmazell GmbH, Raubling (DE)

(72) Inventors: Dirk Weuster-Botz, München (DE); Boqiao Sun, München (DE); Christian Quirin, Branneburg (DE)

(73) Assignee: PharmaZell GmbH, Raubling (DE)

( * ) Notice: Subject to any disclaimer, the term of this patent is extended or adjusted under 35 U.S.C. 154(b) by 230 days.

(21) Appl. No.: 15/314,155

(22) PCT Filed: Jun. 24, 2015

(86) PCT No.: PCT/EP2015/064264
§ 371 (c)(1),
(2) Date: Nov. 28, 2016

(87) PCT Pub. No.: WO2015/197698
PCT Pub. Date: Dec. 30, 2015

(65) Prior Publication Data
US 2017/0191104 A1    Jul. 6, 2017

(30) Foreign Application Priority Data

Jun. 24, 2014 (EP) .................. 14173747
Aug. 26, 2014 (EP) .................. 14182290

(51) Int. Cl.
*C12P 33/00*    (2006.01)
*C12N 9/04*    (2006.01)

(52) U.S. Cl.
CPC ............ *C12P 33/00* (2013.01); *C12N 9/0006* (2013.01); *C12Y 101/01047* (2013.01); *C12Y 101/01145* (2013.01); *C12Y 101/01201* (2013.01)

(58) Field of Classification Search
None
See application file for complete search history.

(56) References Cited

U.S. PATENT DOCUMENTS

| 2011/0091921 A1 | 8/2011 | Aigner |
| 2013/0040341 A1 | 2/2013 | Liu |
| 2014/0087421 A1* | 3/2014 | Weuster-Botz ...... C12N 9/0006 435/61 |

FOREIGN PATENT DOCUMENTS

| WO | 2001064404 A2 | 9/2001 |
| WO | 2009118176 A8 | 10/2009 |
| WO | 2012080504 A1 | 6/2012 |

OTHER PUBLICATIONS

International Search Report of the International Searching Authority dated Dec. 11, 2015 for PCT/EP2015/064264.

(Continued)

*Primary Examiner* — Anand U Desai
(74) *Attorney, Agent, or Firm* — Saul Ewing Arnstein & Lehr LLP

(57) ABSTRACT

The invention relates to novel biocatalytic processes comprising the whole cell reduction of dehydrocholic acid (DHCA) compounds, novel 7β-hydroxy steroid dehydrogenase mutants, the sequences coding for these enzyme mutants, methods for producing the enzyme mutants and use thereof in enzymatic conversions of cholic acid compounds, and in particular in the production of ursodesoxycholic acid (UDCA); also a subject of the invention are novel methods for the synthesis of UDCA using the enzyme mutants; and in particular a further improved method for producing UDCA using recombinant whole cell biocatalysts.

37 Claims, 18 Drawing Sheets
Specification includes a Sequence Listing.

(56) References Cited

OTHER PUBLICATIONS

Boqiao Sun et al., "Multi-Enzymatic One-Pot Reduction of Dehydrocholic Acid to 12-Keto-Ursodeoxycholic Acid with Whole-Cell Biocatalysts" Biotechnology and Bioengineering, vol. 110, No. 1, pp. 68-77 (2013).
H. J. Moon et al., "Molecular Determinants of the Cofactor Specificity of Ribitol Dehydrogenase, a Short-Chain Dehydrogenase/Reductase", Applied and Environmental Microbiology, vol. 78, No. 9, pp. 3079-3086 (2012).
S. Delagrave, et al., "Recursive Ensemple Mutagenesis", Protein Engineering, vol. 6, No. 3, pp. 327-331, 1993.
A. Arkin, et al., "An Algorithm for Protein Engineering: Simulations of Recursive ensemble Mutagenesis", Proc. Natl. Acad. Sci., vol. 89, pp. 7811-7815, 1992.
S. Hirano, et al., "Characterization of NAPD-Dependent 7β-Hydroxysteroid Dehydrogenases from Peptostreptococcus and Eubacterium Aerofaciens", Appl. Environ. Microbio., vol. 43, No. 5, pp. 1057-1063, 1982.
Y. Ike, et al., "Solid Phase Synthesis of Polynucleotides. VIII. Synthesis of Mixed Oligodeoxyribonucleotides by the Phosphotriester Solid Phase Method", Nucleric Acids Research, vol. 11, No. 2, 1983.
I. A. MacDonald, et al., "Bile Salt Induction of 7α and 7β-Hydroxysteroid Dehydrogenases in Clostridium Absonum", Biochim Biophys, Acta vol. 665, No. 2, pp. 262-269, 1981.
K. Itakura, et al., "Synthesis and Use of Synthetic Oligonucleotides", Annu. Rev. Biochem, 53: 323-356, 1984.
S. A. Narang, et al., "DNA Synthesis", Tetraherdron, vol. 39, No. 1, pp. 3-22, 1983.
J. E. Pawlowski, et al., "Cloning and Sequencing of the cDNA for Rat Liver 3α-Hydroxysteroid/Dihydrodol Dehydrogenase", J. Biol Chem, vol. 266, No. 14, pp. 8820-8825, 1991.
D. Zhu, et al., "Enzymatic Enantioselective reduction of α-Ketoesters by a Thermostable 7α-Hydroxysteroid Dehydrogenase from Bacteroides Fragilis", Tetraherdron, vol. 62, No. 18, pp. 4535-4539, 2006.
K. Itakura, et al., "Expression in *Escherichia coli* of a Chemically Synthesized Gene for Hormone Somatostatin", Science, vol. 198, p. 1056, 1991.

\* cited by examiner

7ß-HSDH from *Collinsella aerofaciens*
Accession No.: ZP_01773061

```
  1  mnlrekygew  glilgategv  gkafcekiaa  ggmnvvmvgr  reeklnvlag
eiretygvet
 61  kvvradfsqp  gaaetvfaat  egldmgfmsy  vaclhsfgki  qdtpwekhea
minvnvvtfl
121  kcfhhymrif  aaqdrgavin  vssmtgisss  pwngqygagk  afilkmteav
acecegtgvd
181  vevitlgttl  tpsllsnlpg  gpqgeavmki  altpeecvde  afeklgkels
viagqrnkds
241  vhdwkanhte  deyirymgsf  yrd
```

Fig. 1A

Nucleic acid sequence coding for 7ß-HSDH *from Collinsella aerofaciens*
Accession No.: NZ_AAVN02000010, Region: 52005..52796

```
  1   atgaacctga   gggagaagta   cggtgagtgg   ggcctgatcc   tgggcgcgac
cgagggcgtc
 61   ggcaaggcgt   tctgcgagaa   gatcgccgcc   ggcggcatga   acgtcgtcat
ggtcggccgt
121   cgcgaggaga   agctgaacgt   gctcgcaggc   gagatccgcg   agacctacgg
cgtggagacc
181   aaggtcgtgc   gcgccgactt   tagccagccc   ggcgctgccg   agaccgtctt
cgccgcgacc
241   gagggcctgg   acatgggctt   catgagctac   gtggcctgcc   tgcacagctt
cggtaagatc
301   caggacaccc   cctgggagaa   gcacgaggcc   atgatcaacg   tcaacgtcgt
gaccttcctc
361   aagtgcttcc   accactacat   gcggatcttt   gccgcccagg   accgcggcgc
cgtgatcaac
421   gtctcgtcga   tgaccggcat   cagctccagc   ccctggaacg   gccagtacgg
cgcgggcaag
481   gccttcatcc   tcaagatgac   cgaggccgtg   gcctgcgagt   gcgagggcac
cggcgtcgac
541   gtcgaggtca   tcaccctcgg   caccaccta   accccagcc   tgctgtccaa
cctccccggc
601   ggcccgcagg   gcgaggccgt   catgaagatc   gccctcaccc   ccgaggagtg
cgttgacgag
661   gcctttgaga   agctgggtaa   ggagctctcc   gtcatcgccg   gccagcgcaa
caaggactcc
721   gtccacgact   ggaaggcaaa   ccacaccgag   gacgagtaca   tccgctacat
ggggtcgttc
781 taccgcgact ag
```

Fig.1B

3α-HSDH

Source: *Comamonas testosteroni* ATCC 11996

1 msiivisgca tgigaatrkv leaaghqivg idirdaevia dlstaegrkq aiadvlakcs
61 kgmdglvlca glgpqtkvlg nvvsvnyfga telmdaflpa lkkghqpaav vissvasahl
121 afdknplala leageeakar aivehageqg gnlayagskn altvavrkra aawgeagvrl
181 ntiapgatet pllqaglqdp rygesiakfv ppmgrraeps emasviaflm spaasyvhga
241 qividggida vmrptqf

Fig.1C

Nucleic acid sequence coding for 3α-HSDH

Source: *Comamonas testosteroni* ATCC 11996

Accession No.: AF092031, Region: 158..931

```
  1 atgtccatca tcgtgataag cggctgcgcc accggcattg gtgcggctac gcgcaaggtc
 61 ctggaggcgg ccggtcacca gatcgtaggc atcgatatac gcgatgcgga agtgattgcc
121 gatctctcga cggccgaagg tcgaaagcag gcgattgccg atgtactggc gaagtgcagc
181 aagggcatgg acggcctggt gctgtgcgcc ggcctgggac cgcagaccaa ggtgcttggc
241 aatgtggttt cggtcaatta ttttggcgcg accgagctga tggatgcctt tttgccagcg
301 ctgaaaaaag gccatcagcc cgcagccgtc gtcatctcgt ccgtggcttc cgcgcatctg
361 gcttttgaca agaacccact ggcgctggca ctggaagccg gcgaggaagc caaggcccgc
421 gccattgtcg aacatgcggg agagcagggc ggaaatctgg cctatgcggg cagcaagaat
481 gctttgacgg tggctgtgcg caaacgcgcc gccgcctggg gcgaggctgg cgtgcgcctg
541 aacaccatcg ccccggtgc aaccgagact cccttgctgc aggcgggcct gcaggacccg
601 cgctatggcg aatccattgc caagttcgtt cctcccatgg gccgccgtgc cgagccgtcc
661 gagatggcgt cggtcatcgc cttttttgatg agcccggccg caagctatgt gcatggcgcg
721 cagatcgtca ttgatggcgg cattgatgcg gtgatgcgcc cgacacagtt ctga
```

Fig.1D

Wild type:

MNLREKYGEWGLILGATEGVGKAFCEKIAAGGMNVVMVGRREEKLNV
LAGEIRETYGVETKVVRADFSQPGAAETVFAATEGLDMGFMSYVACL
HSFGKIQDTPWEKHEAMINVNVVTFLKCFHHYMRIFAAQDRGAVINV
SSMTGISSSPWNGQYGAGKAFILKMTEAVACECEGTGVDVEVITLGT
TLTPSLLSNLPGGPQGEAVMKIALTPEECVDEAFEKLGKELSVIAGQ
RNKDSVHDWKANHTEDEYIRYMGSFYRD*

G39D:

MNLREKYGEWGLILGATEGVGKAFCEKIAAGGMNVVMVDRREEKLNV
LAGEIRETYGVETKVVRADFSQPGAAETVFAATEGLDMGFMSYVACL
HSFGKIQDTPWEKHEAMINVNVVTFLKCFHHYMRIFAAQDRGAVINV
SSMTGISSSPWNGQYGAGKAFILKMTEAVACECEGTGVDVEVITLGT
TLTPSLLSNLPGGPQGEAVMKIALTPEECVDEAFEKLGKELSVIAGQ
RNKDSVHDWKANHTEDEYIRYMGSFYRD*

G39D R40F:

MNLREKYGEWGLILGATEGVGKAFCEKIAAGGMNVVMVDFREEKLNV
LAGEIRETYGVETKVVRADFSQPGAAETVFAATEGLDMGFMSYVACL
HSFGKIQDTPWEKHEAMINVNVVTFLKCFHHYMRIFAAQDRGAVINV
SSMTGISSSPWNGQYGAGKAFILKMTEAVACECEGTGVDVEVITLGT
TLTPSLLSNLPGGPQGEAVMKIALTPEECVDEAFEKLGKELSVIAGQ
RNKDSVHDWKANHTEDEYIRYMGSFYRD*

MNLREKYGEWGLILGATEGVGKAFCEKIAAGGMNVVMVDFKEEKLNV
LAGEIRETYGVETKVVRADFSQPGAAETVFAATEGLDMGFMSYVACL
HSFGKIQDTPWEKHEAMINVNVVTFLKCFHHYMRIFAAQDRGAVINV
SSMTGISSSPWNGQYGAGKAFILKMTEAVACECEGTGVDVEVITLGT
TLTPSLLSNLPGGPQGEAVMKIALTPEECVDEAFEKLGKELSVIAGQ
RNKDSVHDWKANHTEDEYIRYMGSFYRD*

G39D R40F R41K K44G:

MNLREKYGEWGLILGATEGVGKAFCEKIAAGGMNVVMVDFKEEGLNV
LAGEIRETYGVETKVVRADFSQPGAAETVFAATEGLDMGFMSYVACL
HSFGKIQDTPWEKHEAMINVNVVTFLKCFHHYMRIFAAQDRGAVINV
SSMTGISSSPWNGQYGAGKAFILKMTEAVACECEGTGVDVEVITLGT
TLTPSLLSNLPGGPQGEAVMKIALTPEECVDEAFEKLGKELSVIAGQ
RNKDSVHDWKANHTEDEYIRYMGSFYRD*

Fig.1E (cont'd)

| | |
|---|---|
| 7beta-HSDH wild type REEKLNVLAG | MNLREKYGEW GLILGATEGV GKAFCEKIAA GGMNVVMVGR |
| 7beta-HSDH G39D REEKLNVLAG | MNLREKYGEW GLILGATEGV GKAFCEKIAA GGMNVVMV<u>D</u>R |
| 7beta-HSDH G39D R40I REEKLNVLAG | MNLREKYGEW GLILGATEGV GKAFCEKIAA GGMNVVMV<u>DI</u> |
| 7beta-HSDH DF REEKLNVLAG | MNLREKYGEW GLILGATEGV GKAFCEKIAA GGMNVVMV<u>DF</u> |
| 7beta-HSDH DFK <u>K</u>EEKLNVLAG | MNLREKYGEW GLILGATEGV GKAFCEKIAA GGMNVVMV<u>DF</u> |
| 7beta-HSDH DFKG <u>KEE</u><u>G</u>LNVLAG | MNLREKYGEW GLILGATEGV GKAFCEKIAA GGMNVVMV<u>DF</u> |
| | |
| 7beta-HSDH wild type VACLHSFGKI | EIRETYGVET KVVRADFSQP GAAETVFAAT EGLDMGFMSY |
| 7beta-HSDH G39D VACLHSFGKI | EIRETYGVET KVVRADFSQP GAAETVFAAT EGLDMGFMSY |
| 7beta-HSDH G39D R40I VACLHSFGKI | EIRETYGVET KVVRADFSQP GAAETVFAAT EGLDMGFMSY |
| 7beta-HSDH DF VACLHSFGKI | EIRETYGVET KVVRADFSQP GAAETVFAAT EGLDMGFMSY |
| 7beta-HSDH DFK VACLHSFGKI | EIRETYGVET KVVRADFSQP GAAETVFAAT EGLDMGFMSY |
| 7beta-HSDH DFKG VACLHSFGKI | EIRETYGVET KVVRADFSQP GAAETVFAAT EGLDMGFMSY |

Fig. 8

```
7beta-HSDH Wild type        QDTPWEKHEA MINVNVVTFL KCFHHYMRIF AAQDRGAVIN
VSSMTGISSS
7beta-HSDH G39D             QDTPWEKHEA MINVNVVTFL KCFHHYMRIF AAQDRGAVIN
VSSMTGISSS
7beta-HSDH G39D R40I        QDTPWEKHEA MINVNVVTFL KCFHHYMRIF AAQDRGAVIN
VSSMTGISSS
7beta-HSDH DF               QDTPWEKHEA MINVNVVTFL KCFHHYMRIF AAQDRGAVIN
VSSMTGISSS
7beta-HSDH DFK              QDTPWEKHEA MINVNVVTFL KCFHHYMRIF AAQDRGAVIN
VSSMTGISSS
7beta-HSDH DFKG             QDTPWEKHEA MINVNVVTFL KCFHHYMRIF AAQDRGAVIN
VSSMTGISSS 7beta-HSDH Wild type        PWNGQYGAGK AFILKMTEAV ACECEGTGVD VEVITLGTTL
TPSLLSNLPG
7beta-HSDH G39D             PWNGQYGAGK AFILKMTEAV ACECEGTGVD VEVITLGTTL
TPSLLSNLPG
7beta-HSDH G39D R40I        PWNGQYGAGK AFILKMTEAV ACECEGTGVD VEVITLGTTL
TPSLLSNLPG
7beta-HSDH DF               PWNGQYGAGK AFILKMTEAV ACECEGTGVD VEVITLGTTL
TPSLLSNLPG
7beta-HSDH DFK              PWNGQYGAGK AFILKMTEAV ACECEGTGVD VEVITLGTTL
TPSLLSNLPG
7beta-HSDH DFK              PWNGQYGAGK AFILKMTEAV ACECEGTGVD VEVITLGTTL
TPSLLSNLPG
```

Fig. 8 (cont'd)

| | | |
|---|---|---|
| 7beta-HSDH Wild type | GPQGEAVMKI ALTPEECVDE AFEKLGKELS VIAGQRNKDS | |
| VHDWKANHTE | | |
| 7beta-HSDH G39D | GPQGEAVMKI ALTPEECVDE AFEKLGKELS VIAGQRNKDS | |
| VHDWKANHTE | | |
| 7beta-HSDH G39D R40I | GPQGEAVMKI ALTPEECVDE AFEKLGKELS VIAGQRNKDS | |
| VHDWKANHTE | | |
| 7beta-HSDH DF | GPQGEAVMKI ALTPEECVDE AFEKLGKELS VIAGQRNKDS | |
| VHDWKANHTE | | |
| 7beta-HSDH DFK | GPQGEAVMKI ALTPEECVDE AFEKLGKELS VIAGQRNKDS | |
| VHDWKANHTE | | |
| 7beta-HSDH DFKG | GPQGEAVMKI ALTPEECVDE AFEKLGKELS VIAGQRNKDS | |
| VHDWKANHTE | | |

| | | | |
|---|---|---|---|
| 7beta-HSDH | Wild type | DEYIRYMGSF | YRD |
| 7beta-HSDH | G39D | DEYIRYMGSF | YRD |
| 7beta-HSDH | G39D R40I | DEYIRYMGSF | YRD |
| 7beta-HSDH | DF | DEYIRYMGSF | YRD |
| 7beta-HSDH DFK | DEYIRYMGSF YRD | | |
| 7beta-HSDH DFKG | DEYIRYMGSF YRD | | |

Fig. 8 (cont'd)

METHOD FOR BIOCATALYTIC WHOLE CELL REDUCTION OF DEHYDROCHOLIC ACID COMPOUNDS, AND 7-β-HYDROXYSTEROID DEHYDROGENASE MUTANTS

CROSS-REFERENCE TO RELATED APPLICATIONS:

This application is the U.S. national phase, pursuant to 35 U.S.C. § 371, of PCT international application Ser. No. PCT/EP2015/064264, Jun. 24, 2015, designating the United States and published in German on Dec. 30, 2015 as publication WO 2015/197698 A3, which claims priority under 35 U.S.C. § 119(a) to European patent application Nos. 14173747.8 and 14182290.8, filed Jun. 24, 2014 and Aug. 26, 2015, respectively. The entire disclosures of the aforementioned patent applications are hereby incorporated herein by reference.

The invention relates to novel biocatalytic processes comprising the whole cell reduction of dehydrocholic acid (DHCA) compounds, novel 7-β-hydroxysteroid dehydrogenase mutants, the sequences coding for these enzyme mutants, methods for producing the enzyme mutants and use thereof in enzymatic conversions of cholic acid compounds (bile acid derivatives), and in particular in the production of ursodesoxycholic acid (UDCA); also a subject of the invention are novel methods for synthesis of UDCA using the enzyme mutants, and in particular a further improved method for producing UDCA using recombinant whole cell biocatalysts.

Sequence Listing:

This application contains a Sequence Listing which has been submitted electronically in ASCII format and is hereby incorporated by reference in its entirety. Said ASCII copy, created on Feb. 16, 2017, is named 054410_00063(US)_SL.TXT and is 78,803 bytes in size.

BACKGROUND OF THE INVENTION

For the medicinal treatment of gallstone problems, the bile salt active substances ursodesoxycholic acid (UDCS or UDCA) and the corresponding diastereomer chenodesoxycholic acid (CDCS or CDCA) inter alia have been used for many years. The two compounds differ only in the configuration of the hydroxy group at C atom 7 (UDCA: β-configuration, CDCA: α-configuration). In the prior art, various methods are described for the production of UDCA, which are performed purely chemically or consist of a combination of chemical and enzymatic process steps. The starting point in each case is cholic acid (CA or CA) or CDCA produced from cholic acid.

Thus the classical chemical method for UDCA production can be represented schematically as follows:

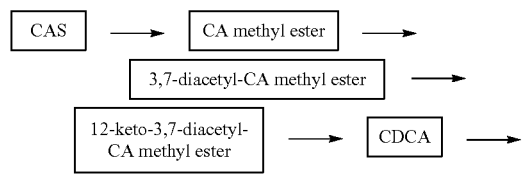

Inter alia, a serious disadvantage is as follows: since the chemical oxidation is not selective, the carboxy group and the 3α and 7α-hydroxy group must be protected by esterification.

An alternative chemical/enzymatic method based on the use of the enzyme 12α-hydroxysteroid dehydrogenase (12α-HSDH) can be represented as follows and is for example described in PCT/EP2009/002190 by the present applicant.

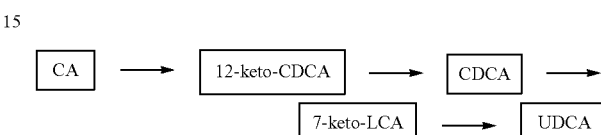

Here the 12α-HSDH oxidizes CA selectively to 12-keto-CDCA. As a result, the two protection steps necessary according to the classical chemical methods become superfluous.

Furthermore, an alternative enzymatic/chemical method is described by Monti, D., et al., (*One-Pot Multienzymatic Synthesis of* 12-*ketoursodeoxycholic Acid: Subtle Cofactor Specificities Rule the Reaction Equilibria of Five Biocatalysts Working in a Row*. Advanced Synthesis & Catalysis, 2009), which is schematically representable as follows:

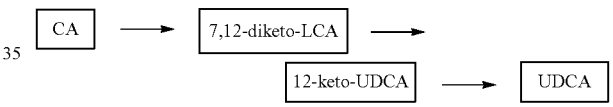

The CA is firstly oxidized to 7,12-diketo-LCA by 7α-HSDH from *Bacteroides fragilis* ATCC 25285 (Zhu, D., et al., *Enzymatic enantioselective reduction of keto esters by a thermostable 7-hydroxysteroid dehydrogenase from Bacteroides fragilis*. Tetrahedron, 2006. 62(18): p. 4535-4539) and 12α-HSDH. These two enzymes are both NADH-dependent. After the reduction by 7β-HSDH (NADPH-dependent) from *Clostridium absonum* ATCC 27555 (DSM 599) (MacDonald, I. A. and P. D. Roach, *Bile induction of 7 alpha- and 7 beta-hydroxysteroid dehydrogenases in Clostridium absonum*. Biochim Biophys Acta, 1981. 665(2): p. 262-9), 12-keto-UDCA is formed. The end product is obtained by Wolff-Kishner reduction. In this method, it is disadvantageous that because of the equilibrium position of the catalyzed reaction a complete conversion is not possible, and that for the first stage of the conversion two different enzymes must be used, which renders the method expensive. For the cofactor regeneration, lactate dehydrogenase (LDH; for regeneration of $NAD^+$) and glucose dehydrogenase (GlcDH or GDH, for regeneration of NADPH) are used. In the cofactor regeneration used there, it is disadvantageous that the co-product produced can only be removed from the reaction mixture with great difficulty, so that the reaction equilibrium cannot be favorably influenced, which results in incomplete conversion of the educt.

A 7β-HSDH from the strain *Collinsella aerofaciens* ATCC 25986 (DSM 3979; former *Eubacterium aerofaciens*) was described in 1982 by Hirano and Masuda (Hirano, S. and N. Masuda, *Characterization of NADP-dependent 7* beta-hydroxysteroid dehydrogenases from *Peptostreptococcus productus* and *Eubacterium aerofaciens*. Appl Environ Microbiol, 1982. 43(5): p. 1057-63). Sequence information on this enzyme was not disclosed. The molecular weight determined by gel filtration was 45,000 Da (see Hirano, page 1059, left-hand column). Furthermore, the reduction of the 7-oxo group to the 7β-hydroxy group could not be observed for the enzyme there (see Hirano, page 1061, Discussion 1$^{st}$paragraph). Those skilled in the art thus recognize that the enzyme described by Hirano et al is not suitable for the catalysis of the reduction of dehydrocholic acid (DHCA or DHCA) in the 7-position to 3,12-diketo-UDCA.

In the applicant's WO2011/064404, a novel 7β-HSDH from *Collinsella aerofaciens* ATCC 25986 is described, which inter alia has a molecular weight (on SDS gel electrophoresis) of about 28-32 kDa, a molecular weight (on gel filtration, under non-denaturing conditions, such as in particular without SDS) of about 53 to 60 kDa, and has the capacity to effect the stereoselective reduction of the 7-carbonyl group of 7-keto LCA to a 7β-hydroxy group.

Apart from this, in WO2011/064404 a method for UDCA production is provided, which is schematically representable as follows:

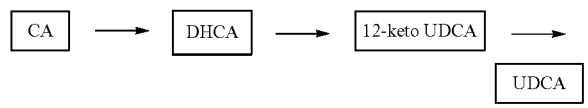

Here the oxidation of CA takes place simply by a classical chemical route. The DHCA is reduced to 12-keto-UDCA by the enzyme pair 7β-HSDH and 3α-HSDH singly in succession or in one pot. Combined with the Wolff-Kishner reduction, UDCA can thus be synthesized from CA in only three steps. While the 7β-HSDH is dependent on the cofactor NADPH, the 3α-HSDH requires the cofactor NADH. The availability of enzyme pairs with dependence on the same cofactor or extended dependence (e.g. on the cofactors NADH and NADPH) would be advantageous, since the cofactor regeneration could thereby be simplified In the applicant's WO2012/080504, in particular a whole cell method for biocatalytic reduction of dehydrocholic acid compounds (DHCA) and in particular a novel method for producing UDCA using recombinant whole cell catalysts which express 7β-HSDH and 3α-HSDH and wherein the enzymatic reduction steps for the cofactor regeneration are coupled with a cofactor-regenerating enzyme, such as for example a suitable glucose dehydrogenase (GDH), is described.

Critical for the efficiency of an enzymatic synthesis is the manner in which the required enzymes are used. In this, whole cell biocatalysis is a proven approach. Here, the often heterologous enzymes are overexpressed within the host organism and the cell as a whole is used as a biocatalyst. A special whole cell biocatalyst from WO2012/080504 heterologously expresses a for example NADPH-dependent, 7β-HSDH from *Collinsella aerofaciens*, a for example NADH-dependent 3α-HSDH from *Comamonas testosteroni* and a GDH utilizing both NADH and also NADPH from *Bacillus subtilis* and is used as a whole cell biocatalyst for the reduction of DHCA to 12-keto-ursodesoxycholic acid (12-keto-UDCA). There, for example 17.7 gBDM L-1 biocatalyst were used to convert 100 mM DHCA 98% to 12-keto-UDCA. Since biocatalysts are a main cost factor in this production process, the present technical challenge consists in the discovery of technical solutions in which the process costs can be decreased, for example by partially replacing the biocatalysts by other substances.

A first objective therefore consists in the provision of novel biocatalytic processes which are characterized in particular by higher cost efficiency in the reductive production of UDCA via DHCA.

A further objective of the invention is the provision of further improved 7β-HSDHs. In particular, enzyme mutants should be provided which can still more advantageously be used for the enzymatic or microbial (biocatalytic) production of UDCA via the stereospecific reduction of DHCA in the 7-position, and in particular have a modified cofactor usage (in particular an improved NADH specificity).

Outline of the Invention

The first problem above could surprisingly be solved by a novel whole cell method for biocatalytic reduction of DHCA compounds, in which the biomass required for the whole cell catalysis can be decreased in that this can partly be replaced by the addition of cofactor NAD and/or NADP. In this, either NAD or NADP or NAD and NADP can be added to the reaction mixture.

In particular, the first problem above was solved by provision of an improved biocatalytic (microbial or enzymatic) process, in particular a whole cell process, comprising the enzymatic conversion of DHCA via two reductive component steps catalyzed by 7β-HSDH and 3α-HSDH respectively, which can proceed simultaneously or separated in time in any order, to 12-keto-UDCA and cofactor regeneration by use of glucose dehydrogenase (GDH) enzymes which regenerate the used cofactor from both reductive component steps.

The second problem above could be solved by creation and characterization of mutants of the 7β-HSDH from aerobic bacteria of the genus *Collinsella*, in particular of the strain *Collinsella aerofaciens*, with improved NADH specificity, wherein the mutants are advantageously also used in the (enzymatic or microbial) conversion, in particular in the context of a whole cell process, of cholic acid compounds, in particular in the production of UDCA.

DESCRIPTION OF DIAGRAMS

FIG. 1a shows the amino acid sequence of the 7β-HSDH from Collinsella aerofaciens (SEQ ID NO: 2) and FIG. 1b the coding nucleic acid sequence for the amino acid sequence of FIG. 1a (SEQ ID NO: 1); FIG. 1c shows the amino acid sequence of the 3α-HSDH from Comanomonas testosteroni (SEQ ID NO: 4) and FIG. 1d the coding nucleic acid sequence for the amino acid sequence of FIG. 1c (SEQ ID NO: 23); FIG. 1e shows in comparison the amino acid sequences of 7β-HSDH wild type (WT) SEQ ID NO: 2) and various mutants: 7β-HSDH D (SEQ ID NO: 9), 7β-HSDH DF (SEQ ID NO: 11), 7β-HSDH DFK (SEQ ID NO: 12) and 7β-HSDH DFKG (SEQ ID NO: 13).

FIG. 2 shows a schematic representation of the two-stage enzymatic reduction of dehydrocholic acid to 12-keto-ursodesoxycholic acid using a whole cell biocatalyst, wherein the component steps of the reduction are catalyzed by a 7β-HSDH and a 3α-HSDH. The used cofactor (NADH or NADPH) is regenerated by a GDH also expressed by the whole cell catalyst GDH with consumption of glucose (formation of glucono-1,5-lactone).

FIG. 8 shows the amino acid sequence alignment of the unmodified 7β-HSDH, the enzyme mutants 7β-HSDH G39D and 7β-HSDH G39D R401 known from the prior art with specific enzyme mutants according to the invention. Positions which deviate from the original sequence are shown underlined. FIG. 8 discloses SEQ ID NOS 2 and 9-13, respectively, in order of appearance.

Figure 9:
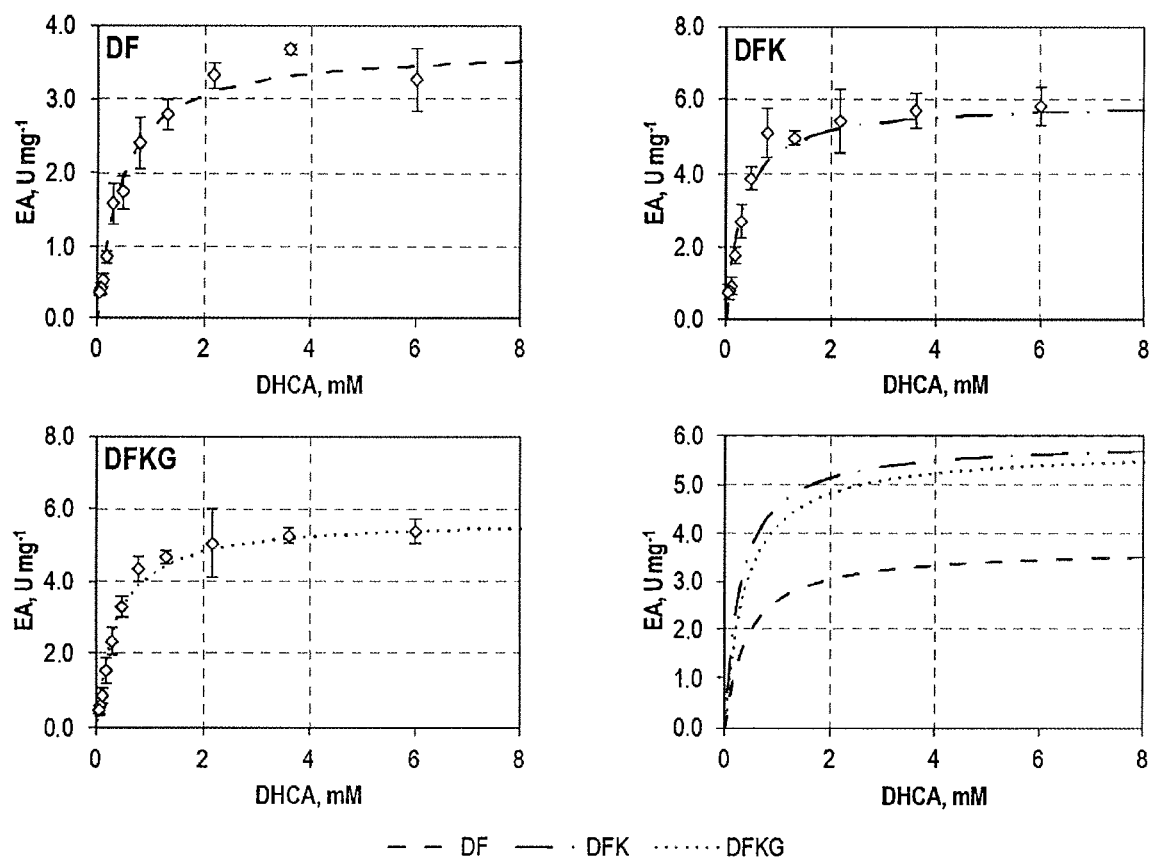

FIG. 9 shows the enzyme kinetic study of 7β-HSDH mutants according to the invention. Plot of the specific enzyme activity against different substrate concentrations used (DHCA/DHCA) at a constant cofactor concentration 0.5 mM NADH.

Figure 10:
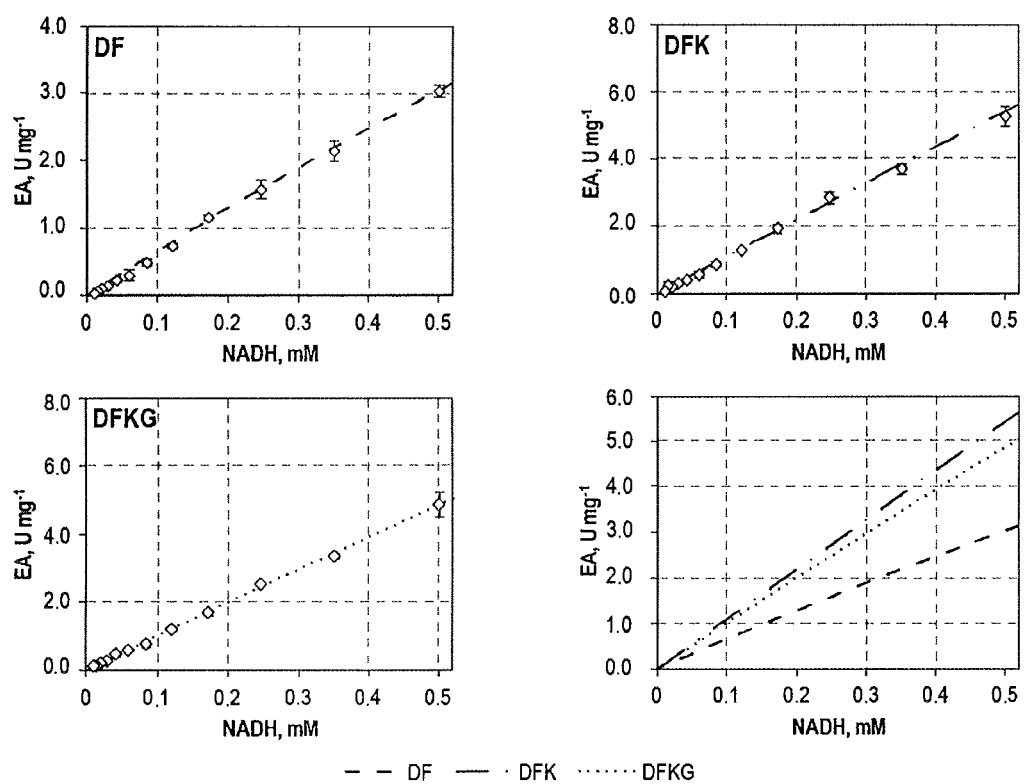

FIG. 10 shows the enzyme kinetic study of 7β-HSDH mutants according to the invention. Plot of the specific enzyme activity against different cofactor concentrations (NADH) used at a constant substrate concentration of 10 mM DHCA/DHCA.

Figure 11:
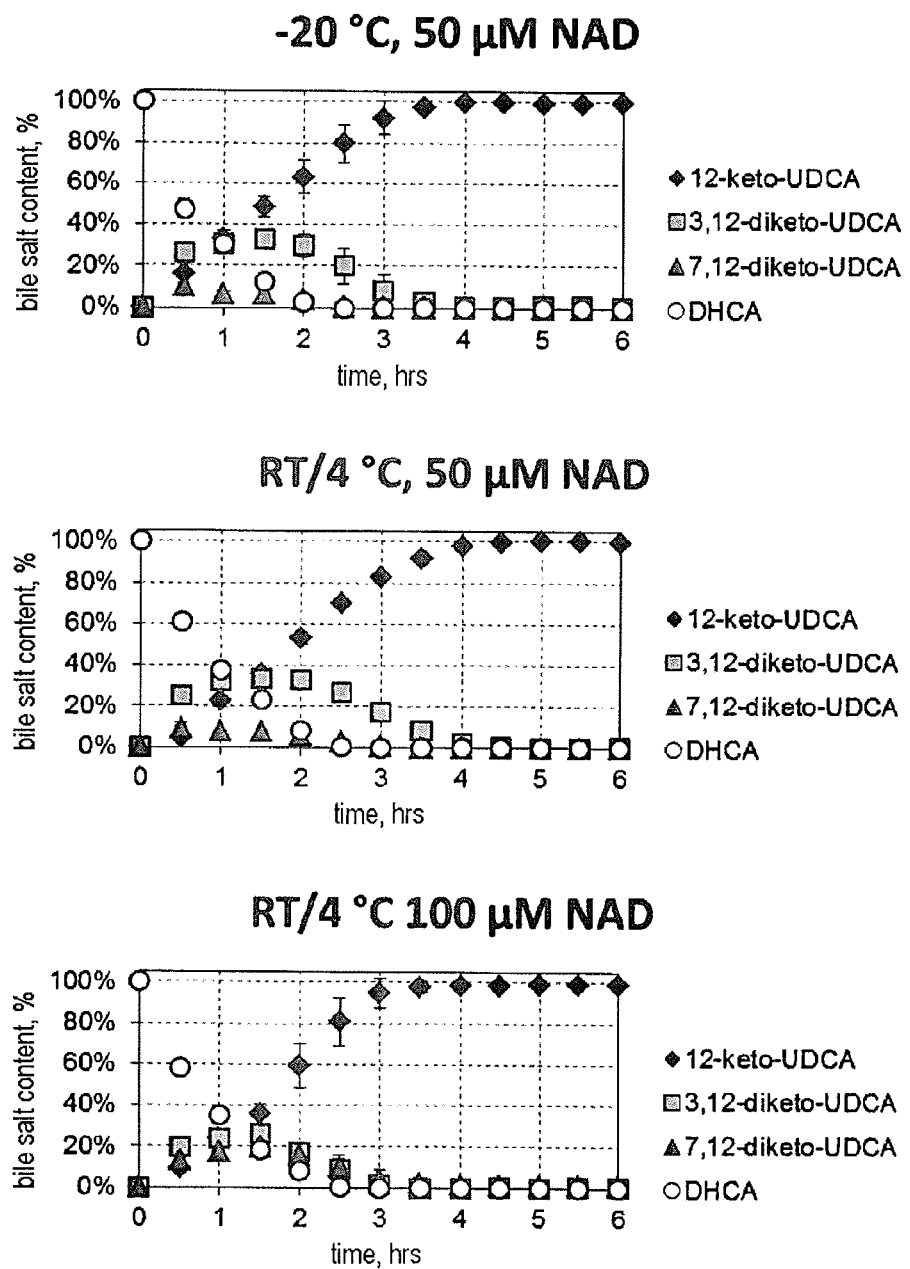

FIG. 11 shows whole cell biotransformations with cells of the whole cell biocatalyst *E. coli* BLLiu p7(A)T3TG-K stored at −20° C. and at room temperature/4° C. The two preparations above were performed under standard conditions: 70 mM DHCA, 350 mM glucose, OD 2 cells, 50 μM NAD, 10 μM NADP, 1 mM MgCl2, 50 mM KPi buffer (pH 7.0) and 30° C. In the lower preparation, the NAD concentration was doubled to 100 μM with otherwise unchanged conditions. The pH was manually adjusted half-hourly to the initial value with NaOH solution (5 M). Mean values from runs in triplicate shown, and the standard deviations are represented by error indicators.

Figure 12:
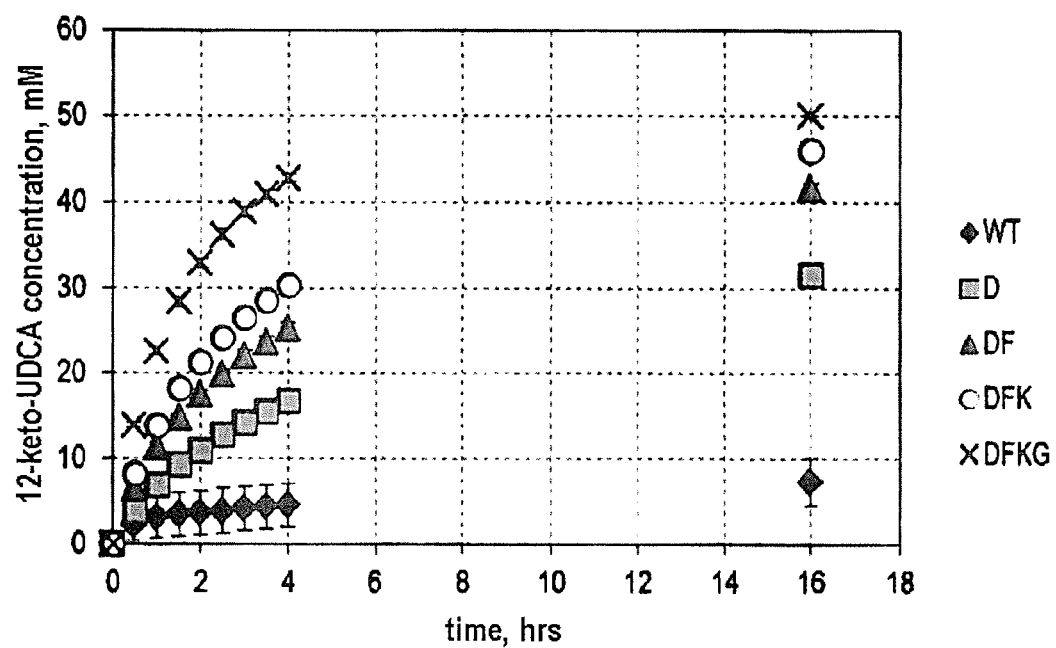

FIG. 12 shows the comparison of the NADH-dependent 7β-HSDH mutants D, DF, DFK and DKFG with the wild type (WT) enzyme. In each case, the reaction conditions were 0.2 mg mL$^{-1}$ 7β-HSDH, 10 U mL$^{-1}$ GDH, 0.5 mM NAD, 50 mM DHCA, 200 mM glucose, 500 mM potassium phosphate, pH 8.0 and 30° C. The reactions were performed in shaken deep well plates without pH control in the strongly buffered system. Standard deviations of the runs in triplicate are represented by error indicators.

Figure 13:
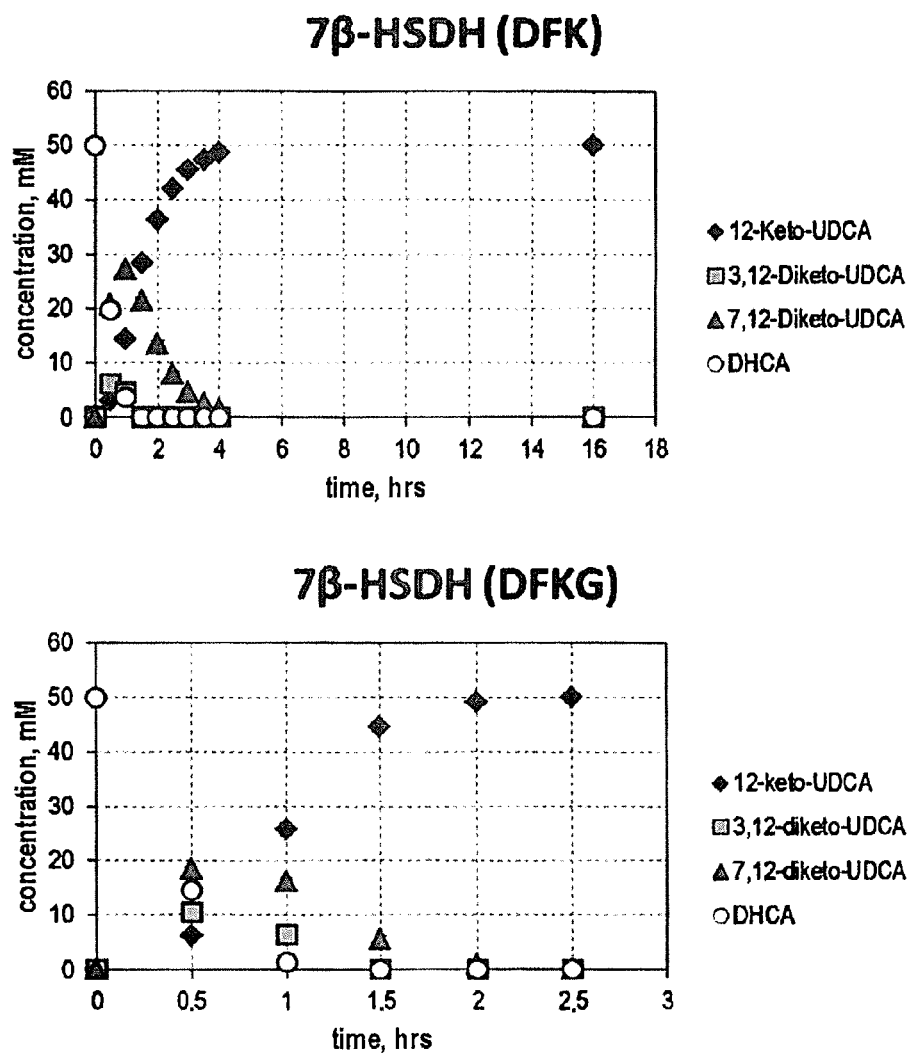

FIG. 13 shows the reaction courses of two-stage biotransformations with the NADH-dependent 7β-HSDH mutants DFK and DFKG. In each case, the reaction conditions were 0.2 mg mL$^{-1}$ 7β-HSDH, 1 U mL$^{-1}$ 3α-HSDH, 10 U mL$^{-1}$ GDH, 0.5 mM NAD, 50 mM DHCA, 200 mM glucose, 500 mM potassium phosphate, pH 8.0 and 30° C. The reactions were performed in shaken deep well plates without pH control in the strongly buffered system. Standard deviations of the runs in triplicate are represented by error indicators.

SPECIFIC EMBODIMENTS OF THE INVENTION

The invention in particular relates to the following specific embodiments:

1. A method for biocatalytic reduction, in particular whole cell reduction, of a dehydrocholic acid compound (DHCA) of the general formula 3:

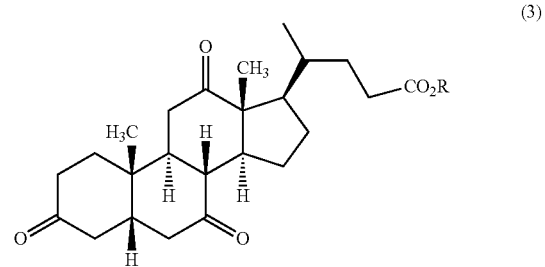

(3)

wherein
R stands for alkyl, H, an alkali metal ion or N(R$^3$)$_4^+$, wherein the residues R$^3$ are the same or different and stand for H or alkyl, or the group —CO$_2$R is replaced by the acid amide group —CONR$^1$R$^2$, wherein R$^1$ and R$^2$ mutually independently stand for an alkyl residue;
to the corresponding 12-keto-ursodesoxycholic acid compound (12-keto-UDCA) of the formula (5)

(5)

wherein R has the meanings stated above, or the group —CO$_2$R is replaced by the acid amide group —CONR$^1$R$^2$, as defined above,
wherein one or more same or different whole cell biocatalysts, in particular one whole cell biocatalyst, in a liquid reaction medium, comprising depending on the cofactor specificity of the enzymes required for the conversion, NAD(H) and/or NADP(H), glucose and optionally further additives, and at least one substrate of the formula (3) is brought into contact with the whole cell biocatalyst(s), and optionally the reaction product is isolated from the reaction medium; wherein the reaction takes place in the presence of 7β-hydroxysteroid dehydrogenase (7β-HSDH), (NAD(H)- and/or NADP(H)-dependent, in particular NADP(H)-dependent); 3α-hydroxysteroid dehydrogenase (3α-HSDH) (NAD (H)- and/or NADP(H)-dependent, in particular NAD(H)-dependent) and glucose dehydrogenase (GDH) (NAD(H)- and/or NADP(H)-dependent; in particular cofactor-nonspecific, i.e. NAD(H)- and NADP(H)-utilizing) wherein NAD (H) and/or NADP(H), depending on the cofactor specificity of the required enzymes, glucose and optionally further additives, and at least one substrate of the formula (3), are essentially not endogenous components of the biocatalyst but are added to the liquid, in particular aqueous, reaction medium; and wherein the whole cell biocatalyst (or the various whole cell biocatalysts together) simultaneously expresses (express) the enzyme activities
(1) 7β-HSDH and
(2) 3α-HSDH, and optionally
(3) expresses (express) GDH, if GDH is not added to the liquid reaction medium;
and wherein the concentrations of whole cell biocatalyst, NAD(H), NADP(H) and substrate of the formula (3) in the reaction mixture are in the following mathematical relationship:

$X < Y \cdot 200$ or $X < Y \cdot 175$, such as in particular $X < Y \cdot 150$ with $Y = c_{DHCA}/70$ and $X = c_{Cat} \cdot 40 + c_{NAD(H)} \cdot 300 + c_{NADP(H)} \cdot 1200$ wherein the parameters are defined as follows:
$c_{DHCA}$=initial substrate concentration [mM] of a compound of the formula (3)
$c_{Cat}$=whole cell biocatalyst concentration [$g_{BDM}$ $L^{-1}$]
$c_{NAD(H)}$=NAD(H) concentration [mM]
$c_{NADP(H)}$=NADP (H) concentration [mM].

Here the following preferred meanings in particular apply singly or as a whole for the parameters stated above:
a) lies in the range from 0.05 to 50, 0.1 to 10, $c_{Cat}$ in particular 0.5 to 5 $g_{BDM}$ $L^{-1}$, wherein "BDM" stands for bacterial dry mass;
b) $c_{NAD(H)}$ and $c_{NADP(H)}$ do not simultaneously stand for 0; in particular both values are greater than 0, i.e. both an NAD(H)- and also an NADP(H)-dependent step is part of the biocatalytic method,
c) the sum of $c_{NAD(H)} + c_{NADP(H)}$ is at least 10 μM, in particular at least 20 μM, such as for example 10 to 1000 mM, or 15 to 500 mM or 20 to 250 mM or 25 to 100 mM.
d) $c_{NAD(H)}$ and $c_{NADP(H)}$ are each lower than the respective saturation concentration of NAD(H) and NADP(H), such as for example in each case 1 to 500 mM, to 200 mM or 10 to 150 mM or 15 to 100 mM, and
e) $c_{DHCA}$ lies in a range from about 0.1 to 500 mM, in particular 1 to 200 mM, or 10 to 100 mM.

For example, at least the conditions a), b) and c), or a), b), c) and d) or, or a) to e) are to be simultaneously set according to the above definition.

A preferred configuration comprises the use of a whole cell biocatalyst, in a liquid reaction medium; wherein the reaction takes place in the presence of 7β-hydroxysteroid dehydrogenase (7β-HSDH), (NADP(H)-dependent); 3α-hydroxysteroid dehydrogenase (3α-HSDH) (NAD(H)-dependent) and glucose dehydrogenase (GDH) (cofactor-nonspecific, i.e. NAD(H)- and NADP(H)-utilizing).

A further preferred configuration comprises a whole cell catalyst which simultaneously expresses the enzyme activities
(1) 7β-HSDH
(2) 3α-HSDH and
(3) GDH
of the above preferred cofactor specificity.

In particular, by following the teaching according to the invention those skilled in the art can select the above concentration values such that a conversion of >95%, >98%, >99% or >99.5% is reached in a time interval of 4 to 24 hrs, in particular 6 to 12 or 7 to 8 hrs, such as for example >98% within 6 to 12 or 7 to 8 hrs; or >99.5% takes place within 4 to 24 hrs, or 6 to 12. Especially preferred are conversions of >99% within a reaction time of less than 10 hrs, such as in particular 3 to 9.5 hrs or 4 to 9 hrs, 5 to 9 hrs, 6 to 9 hrs or 7 to 9 hrs and above all about 8 hrs. These conversions can be determined for example by standard test methods (IPC methods), as are explained in more detail in the following experimental section, wherein the conversion of DHCA to 12-keto-UDCA is determined.

2. The method as described in embodiment 1, wherein the whole cell biocatalyst is a recombinant microorganism.

3. The method as described in one of the previous embodiments, wherein the biocatalyst bears the coding sequences for the enzyme activities of 7β-HSDH, 3α-HSDH and GDH to be expressed, on one or more, in particular one or two, plasmids, or genome-integrated, in particular a plasmid. For example the plasmids:
p7(A)T3rG=p7(A)T3rG-A=pET22b 7beta-HSDH (G39A) T7P 3alpha-HSDH rbs bsGDH (SEQ ID No. 18);
p7(A)T3rG-K=pET28a 7beta-HSDH(G39A) T7P 3alpha-HSDH rbs bsGDH (SEQ ID No. 19);
p7(A)T3TG=p7(A)T3TG-A=pET22b 7beta-HSDH(G39A) T7P 3alpha-HSDH T7P bsGDH (SEQ ID No. 20);
p7(A)T3TG-K=pET28a 7beta-HSDH(G39A) T7P 3alpha-HSDH T7P bsGDH (SEQ ID No. 21) are to be mentioned; and plasmids derived therefrom, wherein one or more of the enzyme-coding sequences contained therein is replaced by a sequence coding for an enzyme mutant, for example the 7beta-HSDH(G39A) coding sequence can be replaced by another 7β-HSDH mutant sequence, such as for example one which codes for a mutant according to SEQ ID No. 9, 10, 11, 12 or 13, or another mutant described herein or known from the prior art.

4. The method as described in one of the previous embodiments, wherein the biocatalyst expresses no 7α-HSDH enzyme activity (in particular none according to SEQ ID No. 6).

5. The method as described in one of the previous embodiments, wherein the 7β-HSDH, 3α-HSDH and GDH are exogenously expressed enzyme activities, i.e. are not endogenous components of the recombinant microorganism (whole cell catalyst).

6. The method as described in one of the previous embodiments, wherein the 7β-HSDH, 3α-HSDH and/or GDH are wild type enzymes or genetically modified enzymes (enzyme mutants).

7. The method as described in one of the previous embodiments, wherein
   a) the 7β-HSDH has an amino acid sequence according to SEQ ID No.2 or an amino acid sequence derived therefrom with at least 60% sequence identity such as for example at least 65, 70, 75, 80, 85, or 90, such as for example at least 91, 92, 93, 94, 95, 96, 97, 98, 99 or 99.5% to this sequence; such as for example an enzyme mutant selected from the mutants known from the applicant's WO2012/080504, such as for example the single mutants: G39A, G39S, G39D, G39V, G39T, G39P, G39N, G39E, G39Q, G39H, G39R, G39K and G39W, and R40D, R40E, R40I, R40V, R40L, R40G and R40A
   the double mutants: (G39D,R40I), (G39D,R40L), (G39D,R40V), (R40D,R41I), (R40D,R41L), (R40D, R41V), (R40I,R41I), (R40V,R41I) and (R40L,R41I). or the triple mutants (G39D,R40I,R41N), or the multiple mutants newly described herein in the following embodiments 20 to 24;
b) the 3α-HSDH has an amino acid sequence according to SEQ ID No.4 or an amino acid sequence derived therefrom with at least 60% sequence identity such as for example at least 65, 70, 75, 80, 85, or 90, such as for example at least 91, 92, 93, 94, 95, 96, 97, 98, 99 or 99.5% to this sequence; and/or
c) the GDH has an amino acid sequence according to SEQ ID No.8 or an amino acid sequence derived therefrom with at least 60% sequence identity such as for example at least 65, 70, 75, 80, 85, or 90, such as for example at least 91, 92, 93, 94, 95, 96, 97, 98, 99 or 99.5% to this sequence;

8. The method as described in one of the previous embodiments, wherein the biocatalyst is a recombinant strain of microorganisms of the genus *Escherichia*, in particular an *E. coli* strain.

9. The method as described in one of the previous embodiments, wherein the 7β-HSDH, 3α-HSDH and GDH utilize the same or different cofactors, selected from NAD(H) and NADP(H); as for example 7β-HSDH utilizes NADP(H), 3α-HSDH utilizes (NAD(H) and GDH utilizes NAD(H) and NADP(H).

10. The method as described in one of the previous embodiments, wherein the GDH is capable of at least partial, in particular complete regeneration of the cofactors (NAD(H) and/or NADP(H), in particular NAD(H) and NADP(H), consumed in the part reactions catalyzed by 7β-HSDH and by 3α-HSDH.

11. The method as described in one of the previous embodiments, wherein the reaction is performed in a buffered aqueous reaction medium, at pH=6-8.

12. The method as described in one of the previous embodiments, wherein glucose is used at an initial concentration of 10 mM to 3000 mM, such as for example 100 to 1000 mM.

13. The method as described in one of the previous embodiments, wherein the reaction is performed continuously or discontinuously.

14. The method as described in one of the previous embodiments, wherein the biocatalyst is non-immobilized or is immobilized on an inert support material.

15. The method as described in one of the previous embodiments, wherein the reaction medium contains further additives, such as alkali or alkaline earth metal salts, polyhydric low molecular weight alcohols and/or buffers. In particular, one or more additives, such as for example alkali or alkaline earth metal salts, such as for example $MgCl_2$ (e.g. 0-20, in particular 1 to 10 mM) and/or polyhydric low molecular weight alcohols, such as glycerin 0-30, in particular 1 to 20% (v/v), can be added to the reaction medium. Furthermore, buffer substances, such as for example tris, acetate, or phosphate buffer, can be added in the range from 10 to 500 mM, in particular 20 to 150 or 25 to 100 mM, such as for example sodium or in particular potassium phosphate buffer. The pH here can be adjusted in the range from 5.5 to 9, in particular 6 to 8, such as for example 7 to 7.5.

16. The method as described in one of the previous embodiments, wherein a whole cell biocatalyst optionally no longer able to proliferate in the reaction medium is used.

17. The method as described in embodiment 16, wherein the whole cell biocatalyst is obtained by activating it by damaging its cell membrane, before it is added to the reaction medium.

There are several possibilities for "activating" the whole cell biocatalyst. In principle, only the membrane should be damaged, e.g. by freezing and thawing, or by storage at room temperature or at 4° C. or by chemically or mechanically perforating the cell membranes.

18. A method for producing an ursodesoxycholic acid compound (UDCA) of the formula (1)

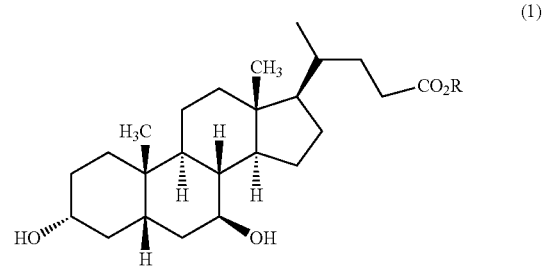

wherein
R stands for alkyl, H, an alkali metal ion or $N(R^3)_4^+$, wherein the residues $R^3$ are the same or different and stand for H or alkyl, or the group —$CO_2R$ is replaced by the acid amide group —$CONR^1R^2$, wherein $R^1$ and $R^2$ mutually independently stand for an alkyl residue;
wherein
a) optionally a cholic acid (CA) of the formula (2)

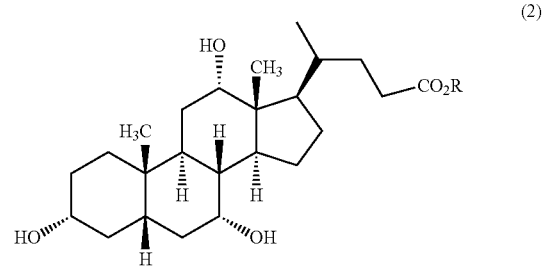

wherein R has the meanings stated above or the group —$CO_2R$ is replaced by the acid amide group —$CONR^1R^2$, as defined above, is oxidized, such as for example chemically or enzymatically, in particular chemically, to the dehydrocholic acid compound (DHCA) of the formula (3)

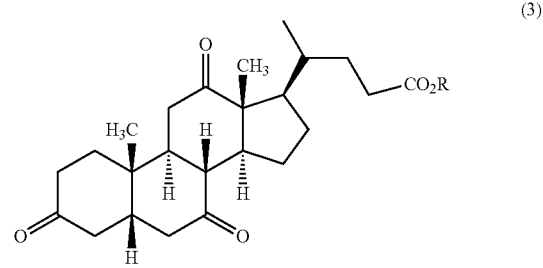

wherein R has the meanings stated above, or the group —$CO_2R$ is replaced by the acid amide group —$CONR^1R^2$, as defined above;
b) DHCA is reduced by a biocatalytic method as described in one of the previous embodiments to the corresponding 12-keto-ursodesoxycholic acid compound (12-keto-UDCA) of the formula (5)

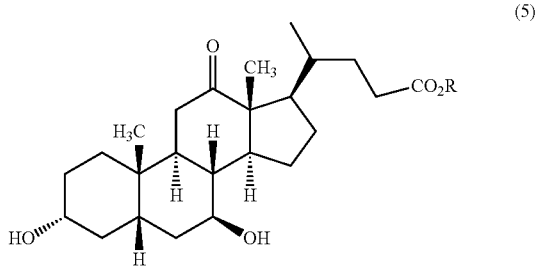

(5)

wherein R has the meanings stated above, or the group —CO₂R is replaced by the acid amide group —CONR¹R², as defined above and then c) 12-keto-UDCA of the formula (5) is chemically reduced to the UDCA compound; and d) the reaction product is optionally further purified.

19. The method as described in one of the previous embodiments, wherein the enzyme activities are contained in the reaction mixture in the following concentration range
    (1) 7β-HSDH: 100 to 3000, such as for example 100 to 1500, such as for example 500 to 1000 U/$g_{BDM}$
    (2) 3α-HSDH: 50 to 500, such as for example 10 to 300 U/$g_{BDM}$
    (3) GDH: 100 to 2000, such as for example 200 to 1000 U/$g_{BDM}$ wherein $c_{Cat}$ lies in the range from 0.05 to 50, 0.1 to 10, in particular 0.5 to 5 $g_{BDM}$ $L^{-1}$.

20. A 7β-hydroxysteroid dehydrogenase (7β-HSDH), which catalyzes at least the stereospecific enzymatic reduction of a 7-ketosteroid to the corresponding 7-hydroxysteroid, wherein the enzyme includes a mutation in each of the positions G39 and R40 of SEQ ID No.2 and optionally in the positions R41 and/or optionally the position K44 of SEQ ID No.2 or in the respective corresponding sequence positions of an amino acid sequence derived therefrom with at least 80% sequence identity to SEQ ID No.2, such as for example at least 85, or 90, such as for example at least 91, 92, 93, 94, 95, 96, 97, 98, 99 or 99.5% to this sequence.

21. The 7β-HSDH as described in embodiment 20, comprising the double mutation G39D/R40F.

22. The 7β-HSDH as described in embodiment 20 or 21, comprising the triple mutation G39D/R40F/R41X₁, wherein X₁ stands for any other amino acid residue, in particular proteinogenic amino acid residue, in particular a residue increasing the NADH specificity, in particular for K, Q, S or R and above all for K.

23. 7β-HSDH as described in one of the embodiments 20 to 22, comprising the quadruple mutation G39D/R40F/R41X₁/K44X₂, wherein X₁ stands for any other amino acid residue, in particular proteinogenic amino acid residue, in particular a residue increasing the NADH specificity in particular for K, Q, S or R and above all K, and X₂ stands for any other amino acid residue, in particular proteinogenic amino acid residue, in particular a residue increasing the NADH specificity, in particular for G, N or Q, and above all G.

24. The 7β-HSDH as described in one of the embodiments 20 to 23, which in comparison to the 7β-HSDH with SEQ ID No.2 exhibits the following property profile:
    a) an increased specific activity (Vmax [U/mg]) for NADH in the enzymatic reduction of DHCA with NADH as cofactor; and optionally
    b) an increased specific activity (Vmax [U/mg]) for NADH in the enzymatic reduction of 7-ketosteroids (in particular bile salts with a keto group in position C7 of the steroid ring), with NADH as cofactor;

25. A nucleotide sequence coding for a 7β-HSDH as described in one of the embodiments 20 to 24.

26. An expression cassette, comprising at least one nucleotide sequence as described in embodiment 25 under the control of at least one regulatory sequence, and optionally coding sequences for at least one (such as for example 1, 2 or 3) further enzyme selected from hydroxysteroid dehydrogenases, in particular 3α-HSDH, and dehydrogenases suitable for the cofactor regeneration, such as for example FDH, GDH, ADH, G-6-PDH or PDH. In particular, the enzymes contained in an expression cassette can utilize different, but preferably the same cofactor pairs, such as for example the cofactor pair NAD+/NADH or NADP+/NADPH.

27. An expression vector comprising at least one expression cassette as described in embodiment 26.

28. A recombinant microorganism which bears at least one nucleotide sequence as described in embodiment 25 or at least one expression cassette as described in embodiment 26 or at least one expression vector as described in embodiment 27.

29. The recombinant microorganism as described in embodiment 28, which additionally optionally bears the coding sequence for at least one further enzyme, selected from hydroxysteroid dehydrogenases (HSDH) and dehydrogenases suitable for the cofactor regeneration.

30. The recombinant microorganism as described in embodiment 29, wherein
    the further HSDH is selected from 3α-HSDHs; and
    the dehydrogenase is selected from NADH-regenerating enzymes, such as NADH dehydrogenases, alcohol dehydrogenases (ADH), and NADH regenerating formate dehydrogenases (FDH), and glucose dehydrogenase (GDH), glucose-6-phosphate dehydrogenase (G-6-PDH), or phosphite dehydrogenases (PtDH), and NADH regenerating glucose dehydrogenases (GDH).

31. The recombinant microorganism as described in one of the embodiments 28 to 30 which is a 7α-HSDH knockout strain.

32. The method as described in one of the embodiments 1 to 19, performed using a microorganism as described in one of the embodiments 28 to 30.

33. A method for enzymatic or microbial synthesis of 7β-hydroxysteroids, wherein the corresponding 7-ketosteroid is reduced in the presence of a 7β-HSDH according to the definition in one of the embodiments to 24 or in the presence of a recombinant microorganism expressing this 7β-HSDH as described in one of the embodiments 28 to 32, and optionally at least one reduction product formed is isolated from the reaction mixture.

34. The method as described in embodiment 33, wherein the 7-ketosteroid is selected from
    dehydrocholic acid (DHCA),
    7-keto-lithocholic acid (7-keto-LCA),
    7,12-diketo-lithocholic acid (7,12-diketo-LCA) and
    the derivatives thereof, such as in particular a salt, amide or alkyl ester of the acid.

35. The method as described in embodiment 33 or 34, wherein the reduction takes place in the presence of and in particular with consumption of NADH and/or NAPH; in particular with consumption of NADH.

36. The method as described in embodiment 35, wherein used NADH is regenerated by coupling with an NADH-regenerating enzyme, wherein this is in particular selected from NADPH dehydrogenases, alcohol dehydrogenases (ADH), and NADH-regenerating formate dehydrogenases (FDH) and an NADH-regenerating glucose dehydrogenase (GDH), wherein the NADH-regenerating enzyme is optionally expressed by a recombinant microorganism;

and/or wherein used NADPH is regenerated by coupling with an NADPH-regenerating enzyme, wherein this is in particular selected from NADPH dehydrogenases, NADPH-regenerating formate dehydrogenases (FDH), NADPH-regenerating alcohol dehydrogenases (ADH), NADPH-regenerating glucose-6-phosphate dehydrogenases (G6PDH), NADH-regenerating phosphite dehydrogenases (PtDH) and NADPH-regenerating glucose dehydrogenases (GDH), wherein the NADPH-regenerating enzyme is optionally expressed in a recombinant microorganism.

37. The method as described in embodiment 36, wherein the NADPH-regenerating enzyme is selected from GDHs.

38. A method for producing ursodesoxycholic acid (UDCA) of the formula (1)

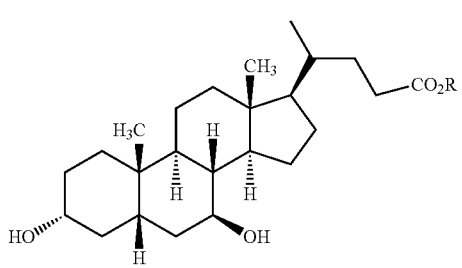

(1)

wherein

R stands for alkyl, H, an alkali metal ion or $N(R^3)_4^+$, wherein the residues $R^3$ are the same or different and stand for H or alkyl, or the group —$CO_2R$ is replaced by the acid amide group —$CONR^1R^2$, wherein $R^1$ and $R^2$ mutually independently stand for an alkyl residue;

wherein a) optionally a cholic acid (CA) of the formula (2)

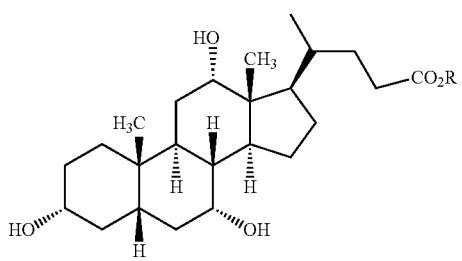

(2)

wherein R has the meanings stated above or the group —$CO_2R$ is replaced by the acid amide group —$CONR^1R^2$, as defined above, is oxidized, such as for example chemically or enzymatically, in particular chemically to the dehydrocholic acid (DHCA) of the formula (3)

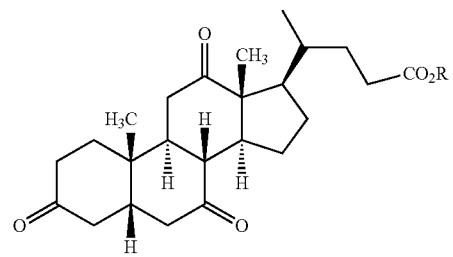

(3)

wherein R has the meanings stated above, or the group —$CO_2R$ is replaced by the acid amide group —$CONR^1R^2$, as defined above;

b) DHCA in the presence of at least one 7β-HSDH mutant according to the definition in one of the embodiments 20 to 24 and in the presence of at least one 3α-HSDH is reduced to the corresponding 12-keto-ursodesoxycholic acid (12-keto-UDCA) of the formula (5)

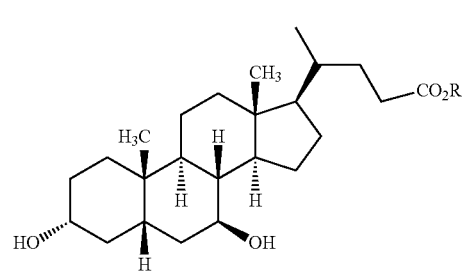

(5)

wherein R has the meanings stated above, or the group —$CO_2R$ is replaced by the acid amide group —$CONR^1R^2$, as defined above, in particular in the presence and with consumption of NADH and/or NADPH and then c) 12-keto-UDCA of the formula (5) is chemically reduced to UDCA; and d) the reaction product is optionally further purified.

39. The method as described in embodiment 38 wherein at least step b) is performed in the presence of a recombinant microorganism as described in one of the embodiments 28 to 32.

40. The method as described in embodiment 38 or 39, wherein step b) is coupled with the same or different cofactor regeneration systems.

41. A method for producing UDCA of the formula (1)

(1)

wherein

R stands for alkyl, $NR^1R^2$, H, an alkali metal ion or $N(R^3)_4^+$, wherein the residues $R^3$ are the same or different and stand for H or alkyl or the group —CO$_2$R is replaced by the acid amide group —CONR$^1$R$^2$, as defined above
wherein
a) optionally a CA of the formula (2)

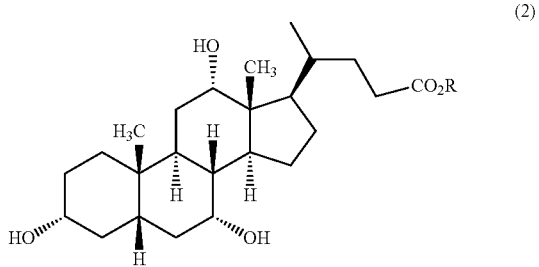

(2)

wherein R has the meanings stated above, or the group —CO$_2$R is replaced by the acid amide group —CONR$^1$R$^2$, as defined above, is oxidized, such as for example chemically or enzymatically, especially chemically, to the DHCA of the formula (3)

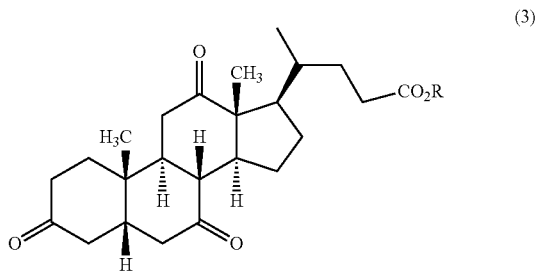

(3)

wherein R has the meanings stated above, or the group —CO$_2$R is replaced by the acid amide group —CONR$^1$R$^2$ as defined above;
b) DHCA in the presence of at least one 7β-HSDH and in the presence of at least one 3α-HSDH is reduced, in particular in the presence and with consumption of NADH and/or NADPH, to the corresponding 12-keto-UDCA of the formula (5)

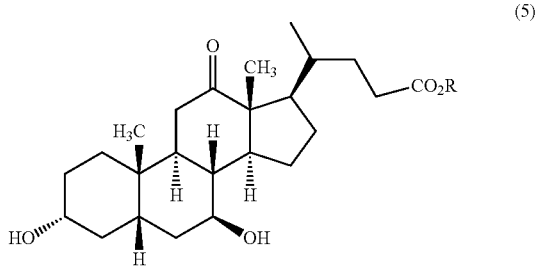

(5)

wherein R has the meanings stated above, or the group —CO$_2$R is replaced by the acid amide group —CONR$^1$R$^2$ as defined above, and then
c) 12-keto-UDCA of the formula (5) is chemically reduced to UDCA; and
d) the reaction product is optionally further purified;
wherein the conversions of step b) take place in the presence of a recombinant microorganism as described in one of the embodiments 28 to 32.

The present invention is not limited to the specific embodiments described here. Rather, through the teaching of the present invention, those skilled in the art are rendered capable of providing further configurations of the invention without unacceptable effort. Thus for example they can also deliberately generate further enzyme mutants and screen and optimize these for the desired property profile (improved cofactor dependence and/or stability, decreased substrate inhibition); or isolate and use according to the invention further suitable wild type enzymes (7β- and 3α-HSDHs, FDHs, GDHs ADHs etc.). Furthermore, for example depending on the property profile (in particular cofactor dependence) of the HSDHs used, such as in particular 7β-HSDH and 3α-HSDH or mutants thereof, they can select usable dehydrogenases (GDH, FHD, ADH etc.) and mutants thereof suitable for cofactor regeneration, and distribute the selected enzymes onto one or more expression constructs or vectors and therewith if necessary create one or more recombinant microorganisms, which then enable an optimized whole cell-based production method.

Further Configurations of the Invention
1. General Definitions and Abbreviations Used A "whole cell catalyst" comprises both viable (able to proliferate, in any growth stage) and also no longer viable microorganisms, in particular recombinant microorganisms, which contain the enzyme activities necessary for performing a method according to the invention completely, or at least partly, in expressed form. Here, the whole cell catalyst can additionally have a cell wall perforated by chemical, mechanical or other action (temperature, storage), in order further to promote the exchange of substances (in particular substrate, product, cofactors) with the surrounding reaction medium.

Unless otherwise stated, the term "7β-HSDH" designates a dehydrogenase enzyme, which catalyzes at least the stereospecific and/or regiospecific reduction of DHCA or 7,12-diketo-UDCA (7,12-diketo-LCA) to 3,12-diketo-UDCA or 12-keto-UDCA in particular with stoichiometric consumption of NADPH, and optionally the corresponding reverse reaction. Here the enzyme can be a natural or recombinantly produced enzyme. The enzyme can in principle be present mixed with cellular, such as for example protein impurities, but preferably in pure form. Suitable detection methods are described for example in the following experimental section or known from the literature (e.g. *Characterization of NADP-dependent 7 beta-hydroxysteroid dehydrogenases from Peptostreptococcus productus and Eubacterium aerofaciens*. S Hirano and N Masuda. Appl Environ Microbiol. 1982). Enzymes with this activity are classified under the EC number 1.1.1.201.

Unless otherwise stated, the term "3α-HSDH" designates a dehydrogenase enzyme, which catalyzes at least the stereospecific and/or regiospecific reduction of 3,12-diketo-UDCA or DHCA to 12-keto-UDCA or 7,12-diketo-UDCA (7,12-diketo-LCA), in particular with stoichiometric consumption of NADH and/or NADPH, and optionally the corresponding reverse reaction. Suitable detection methods are for example described in the following experimental section or known from the literature. Suitable enzymes are obtainable for example from *Comanomonas testosteroni* (e.g. ATCC11996). An NADPH-dependent 3α-HSDH is for example known from rodents and is also usable. (Cloning and sequencing of the cDNA for rat liver 3 alpha-hydroxysteroid/dihydrodiol dehydrogenase, Pawlowski, M Huizinga and T M Penning, May 15, 1991 The Journal of Biological Chemistry, 266, 8820-8825). Enzymes with this activity are classified under the EC number 1.1.1.50.

Unless otherwise stated, the term "GDH" designates a dehydrogenase enzyme, which catalyzes at least the oxidation of β-D-glucose to D-glucono-1,5-lactone with stoichiometric consumption of NAD$^+$ and/or NADP$^+$ and optionally the corresponding reverse reaction. Suitable enzymes are obtainable for example from *Bacillus subtilis* or *Bacillus megaterium*. Enzymes with this activity are classified under the EC number 1.1.1.47.

Unless otherwise stated, the term "FDH" designates a dehydrogenase enzyme, which catalyzes at least the oxidation of formic acid (or corresponding formate salts) to carbon dioxide with stoichiometric consumption of NAD$^+$ and/or NADP$^+$, and optionally the corresponding reverse reaction. Suitable detection methods are for example described in the following experimental section or known from the literature. Suitable enzymes are obtainable for example from *Candida boidinii, Pseudomonas* sp, or *Mycobacterium vaccae*. Enzymes with this activity are classified under the EC number 1.2.1.2.

A "pure form" or a "pure" or "essentially pure" enzyme is understood according to the invention to mean an enzyme with a purity of more than more than 80, preferably more than 90, in particular more than 95, and above all more than 99 wt. %, based on the total protein content determined by normal protein determination methods, such as for example the biuret method or the protein determination according to Lowry et al. (see description in R. K. Scopes, Protein Purification, Springer Verlag, New York, Heidelberg, Berlin (1982)).

A "redox equivalent" is understood to mean a low molecular weight organic compound usable as an electron donor or electron acceptor, such as for example nicotinamide derivatives such as NAD$^+$ and NADH$^+$ or their reduced forms NADH and NADPH respectively. "Redox equivalent" and "cofactor" are used as synonyms in the context of the present invention. Thus a "cofactor" in the sense of the invention can also be described as a "redox-capable factor", i.e. as a cofactor, which can be present in reduced and an oxidized form.

A "consumed" cofactor is understood to mean that reduced or oxidized form of the cofactor which is converted into the corresponding oxidized or reduced form respectively in the course of a predefined reduction or oxidation reaction of a substrate. By regeneration, the oxidized or reduced cofactor form produced in the reaction is converted back into the reduced or oxidized starting form respectively, so that this is again available for the conversion of the substrate.

A "modified cofactor usage" is understood in the context of the present invention to mean a qualitative or quantitative change in comparison to a reference. In particular, modified cofactor usage through the implementation of amino acid sequence mutations is to be observed. This modification is then observable in comparison to the non-mutated starting enzyme. Here, the activity with regard to a certain cofactor can be increased or decreased or completely interdicted by implementing a mutation. However, a modified cofactor usage also includes changes of the type such that instead of a specificity for a single cofactor, now at least one further, second cofactor, different from the first cofactor, is utilizable (i.e. an extended cofactor usage is present). Conversely, however, an originally present capability for utilization of two different cofactors can also be changed such that specificity is increased for only one of these cofactors or decreased or completely eliminated for one of the cofactors. Thus for example, an enzyme which is dependent on the cofactor NAD (NADH), owing to a change in the cofactor usage can now be dependent both on NAD (NADH) and also on the cofactor NADP (NADPH) or the original dependence on NAD (NADH) can be completely converted to a dependence on NADP (NADPH) and vice versa.

According to the invention, unless otherwise defined, the terms "NAD$^+$/NADH dependence" and "NADP$^+$/NADPH dependence" are to be interpreted broadly. These terms include both "specific" dependences, i.e. exclusively dependence on NAD$^+$/NADH or NADP$^+$/NADPH respectively, and also the dependence of the enzymes used according to the invention on both cofactors, i.e. dependence on NAD$^+$/NADH and NADP$^+$/NADPH.

The same applies for the terms used "NAD$^+$/NADH-accepting" and "NADP$^+$/NADPH-accepting" respectively.

According to the invention, unless otherwise defined, the terms "NAD$^+$/NADH-regenerating" and "NADP$^+$/NADPH-regenerating" are to be interpreted broadly. These terms include both "specific", i.e. exclusive capability to regenerate consumed cofactor NAD$^+$/NADH or NADP$^+$/NADPH, and also the capability to regenerate both cofactors, i.e. NAD$^+$/NADH and NADP$^+$/NADPH.

"Proteinogenic" amino acids comprise in particular (single letter code): G, A, V, L, I, F, P, M, W, S, T, C, Y, N, Q, D, E, K, R and H.

An "immobilization" is understood according to the invention to mean the covalent or non-covalent binding of a biocatalyst used according to the invention, such as for example a 7β-HSDH on a solid, i.e. essentially insoluble in the surrounding liquid medium, support material. Accordingly, according to the invention whole cells, such as the recombinant microorganisms used according to the invention, can also be immobilized by means of such supports.

A "substrate inhibition decreased in comparison to the non-mutated enzyme" means that the substrate inhibition observed for a certain substrate with the non-mutated enzyme is no longer to be observed, i.e. is essentially no longer measureable, or only sets in at higher substrate concentration, i.e. the $K_i$ value is increased.

A "cholic acid compound" is understood according to the invention to mean compounds with the basic carbon skeleton, in particular the steroid structure, of cholic acid and the presence of keto and/or hydroxy or acyloxy groups in ring position 7 and optionally ring positions 3 and/or 12.

A compound of a specific type, such as for example a "cholic acid compound" or an "ursodesoxycholic acid compound" is understood in particular also to mean derivatives of the underlying starting compound (such as for example cholic acid or ursodesoxycholic acid).

Such derivatives include "salts", such as for example alkali metal salts such as lithium, sodium and potassium salts of compounds, and ammonium salts, wherein an ammonium salt includes the NH$_4^+$ salt and those ammonium salts wherein at least one hydrogen atom can be replaced by a $C_1$-$C_5$ alkyl residue. Typical alkyl residues are in particular $C_1$-$C_4$ alkyl residues, such as methyl, ethyl, n- or i-propyl, n-, sec- or tert-butyl, and n-pentyl and n-hexyl and the singly or multiply branched analogs thereof "Alkyl esters" of compounds according to the invention are in particular low alkyl esters, such as for example $C_1$-$C_6$ alkyl esters. As non-limiting examples, methyl, ethyl, n- or i-propyl, n-, sec- or tert-butyl esters, or longer-chain esters, such as for example n-pentyl and n-hexyl esters and the singly or multiply branched analogs thereof, are to be mentioned.

"Amides" are in particular conversion products of acids according to the invention with ammonia or primary or secondary monoamines. Such amines are for example mono- or di-$C_1$-$C_6$ alkyl monoamines, wherein the alkyl residues mutually independently can optionally be further substituted, such as for example by carboxy, hydroxy, halogen (such as F, Cl, Br, I), nitro and sulfonate groups.

"Acyl groups" according to the invention are in particular non-aromatic groups with 2 to 4 carbon atoms, such as for example acetyl, propionyl and butyryl, and aromatic groups with an optionally substituted mononuclear aromatic ring, wherein suitable substituents are for example selected from hydroxy, halogen (such as F, Cl, Br, I), nitro and $C_1$-$C_6$ alkyl groups, such as for example benzoyl or toluoyl.

The hydroxysteroid compounds used or produced according to the invention, such as for example cholic acid, ursodesoxycholic acid, 12-keto-chenodesoxycholic acid, chenodesoxycholic acid and 7-keto-lithocholic acid can be used in the method according to the invention in stereoisomerically pure pure form or mixed with other stereoisomers or obtained therefrom. Preferably, however, the compounds used or the compounds produced are used or isolated in essentially stereoisomerically pure form.

Synonyms used here are CDCS and CDCA; UDCS and UDCA; DHCS and DHCA; NAD and $NAD^+$; and NADP and $NADP^+$.

"BDM" stands for bacterial dry mass.

In the following table 1, the structural formulae, their chemical names and the abbreviations of essential chemical compounds are summarized in table form:

TABLE 1

| Formula | Abbreviation | Chemical Name |
|---|---|---|
| Cholic acid | CA | cholic acid |
| Dehydrocholic acid | DHCA | dehydrocholic acid |
| 3,12-diketo-7β-cholanic acid | 3,12-diketo-7β-CA | 3,12-diketo-7β-cholanic acid |

TABLE 1-continued

| Formula | Abbreviation | Chemical Name |
|---|---|---|
| 12-keto-ursodeoxycholic acid | 12-keto-UDCA | 12-keto-ursodeoxycholic acid |
| Ursodeoxycholic acid | UDCA | ursodeoxycholic acid |
| Cholic acid methyl ester | CA methyl ester | cholic acid methyl ester |
| 3,7-diacetyl-cholic acid methyl ester | 3,7-diacetyl-CA methyl ester | 3,7-diacetyl-cholic acid methyl ester* |

TABLE 1-continued

| Formula | Abbreviation | Chemical Name |
|---|---|---|
| 12-keto-3,7-diacetyl-cholanic acid methyl ester | 12-keto-diacetyl-CA methyl ester | 12-keto-3,7-diacetyl-cholanic acid methyl ester* |
| Chenodeoxycholic acid | CDCA | chenodeoxycholic acid |
| 7-keto-lithocholic acid | 7-keto-LCA | 7-keto-lithocholic acid |
| 7,12-diketo-lithocholic acid | 7,12-diketo-LCA | 7,12-diketo-lithocholic acid |

TABLE 1-continued

| Formula | Abbreviation | Chemical Name |
|---|---|---|
| 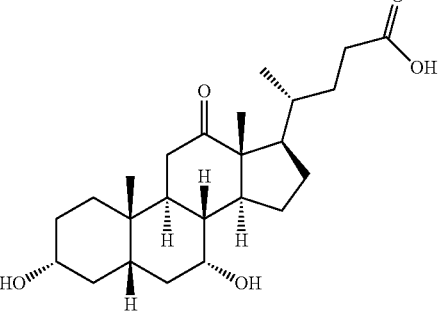 12-keto-chenodeoxycholic acid | 12-keto-CDCA | 12-keto-chenodeoxycholic acid |

3,12-diketo-7-beta-cholanic acid is a synonym for 3,12-diketo-ursodesoxycholic acid (3,12-diketo-UDCA) 7,12-diketo-lithocholic acid is a synonym for 7,12-diketo-ursodesoxycholic acid (7,12-diketo-UDCA).

2. Proteins

The present invention is not limited to the proteins and enzymes specifically disclosed herein in particular with 7β-HSDH, FDH, GDH or 3α-HSDH activity and mutants thereof, but rather extends also to functional equivalents thereof.

In the context of the present invention, "functional equivalents" or analogs of the enzymes specifically disclosed are various polypeptides which furthermore possess the desired biological activity, such as for example 7β HSDH activity.

Thus for example "functional equivalents" are understood to be enzymes which in the test used for 7β-HSDH, FDH, GDH or 3α-HSDH activity display an activity higher or lower than a starting enzyme comprising an amino acid sequence defined herein by at least 1%, such as for example at least 10% or 20%, such as for example at least 50% or 75% or 90%.

Moreover, functional equivalents are preferably stable between pH 4 to 11 and advantageously possess a pH optimum in a range from pH 6 to 10, such as in particular 8.5 to 9.5, and a temperature optimum in the range from 15° C. to 80° C. or 20° C. to 70° C., such as for example about 45 to 60° C. or about 50 to 55° C.

The 7β-HSDH activity can be determined by means of various known tests. Without being limited thereto, a test using a reference substrate, such as for example CA or DHCA, under standardized conditions as described in the experimental section, may be mentioned.

Tests for determining the FDH, GDH or 3α-HSDH activity are also known per se.

"Functional equivalents" is understood according to the invention also to mean in particular "mutants" which in at least one sequence position of the aforesaid amino acid sequences have an amino acid other than that specifically mentioned but nonetheless possess one of the aforesaid biological activities. Thus "functional equivalents" include the mutants obtainable by one or more, such as for example 1, 2, 3, 4, 5, 6, 7, 8, 9, 10, 11, 12, 13, 14 or 15, amino acid additions, substitutions, deletions and/or inversions, wherein the said modifications can occur at any sequence position, as long as they lead to a mutant with the property profile according to the invention. Functional equivalence is in particular also present when the reactivity patterns between mutant and unmodified polypeptide qualitatively coincide, i.e. for example the same substrates are converted at a different rate. Examples of suitable amino acid substitutions are summarized in the following table 2:

TABLE 2

| Original Residue | Examples of Substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described and "functional derivatives" and "salts" of the polypeptides.

"Precursors" here are natural or synthetic precursors of the polypeptides with or without the desired biological activity.

The expression "salts" is understood to mean both salts of carboxyl groups and also acid addition salts of amino groups of the protein molecules according to the invention. Salts of carboxyl groups can be produced in a manner known per se and comprise inorganic salts such as for example sodium, calcium, ammonium, iron and zinc salts, and salts with organic bases, such as for example amines, such as triethanolamine, arginine, lysine, piperidine and the like. Acid addition salts, such as for example salts with mineral acids, such as hydrochloric acid or sulfuric acid and salts with organic acids, such as acetic acid and oxalic acid, are also a subject of the invention.

"Functional derivatives" of polypeptides according to the invention can also be produced on functional amino acid side groups or on their N- or C-terminal end by means of known techniques. Such derivatives for example include aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also include polypeptides which are accessible from other organisms, and naturally occurring variants. For example, ranges of homologous sequence regions can be identified by sequence comparison and equivalent enzymes defined on the basis of the specific provisions of the invention.

"Functional equivalents" also include fragments, preferably individual domains or sequence motifs of the polypeptides according to the invention, which for example have the desired biological function.

Apart from this, "functional equivalents" are fusion proteins which have one of the aforesaid polypeptide sequences or functional equivalents derived therefrom and at least one further heterologous sequence functionally different therefrom in functional N- or C-terminal linkage (i.e. without significant mutual functional impairment of the fusion protein parts). Non-limiting examples of such heterologous sequences are for example signal peptides, histidine anchors or enzymes.

"Functional equivalents" also comprised according to the invention are homologs to the specifically disclosed proteins. These possess at least 60%, preferably at least 75% in particular at least 85%, such as for example 90, 91, 92, 93, 94, 95, 96, 97, 98 or 99%, homology (or identity) to one of the specifically disclosed amino acid sequences, calculated according to the algorithm of Pearson and Lipman, Proc. Natl. Acad, Sci. (USA) 85(8), 1988, 2444-2448. A percentage homology or identity of a homologous polypeptide according to the invention means in particular percentage identity of the amino acid residues based on the overall length of one of the amino acid sequences specifically described herein.

The percentage identity values can also be determined on the basis of BLAST alignments, algorithm blastp (protein-protein BLAST), or by use of the clustal settings stated below.

In the case of a possible protein glycosylation "functional equivalents" according to the invention include proteins of the type described above in deglycosylated or glycosylated form and modified forms obtainable by modification of the glycosylation pattern.

Homologs of the proteins or polypeptides according to the invention can be created by mutagenesis, e.g. by point mutation, extension or truncation of the protein.

Homologs of the proteins according to the invention can be identified by screening of combinatorial banks of mutants, such as for example truncation mutants. For example, a variegated bank of protein variants can be created by combinatorial mutagenesis at the nucleic acid level, such as for example by enzymatic ligation of a mixture of synthetic oligonucleotides. There are a large number of methods which can be used for the production of banks of potential homologs from a degenerate oligonucleotide sequence. The chemical synthesis of a degenerate gene sequence can be performed in a DNA synthesizer, and the synthetic gene can then be ligated into a suitable expression vector. The use of a degenerate gene set enables the provision of all sequences in one mixture, which code for the desired set of potential protein sequences. Methods for the synthesis of degenerate oligonucleotides are known to those skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, several techniques are known for the screening of gene products of combinatorial banks which have been produced by point mutations or truncation, and for the screening of cDNA banks for gene products with a selected property. These techniques can be adapted to the rapid screening of the gene banks which have been created by combinatorial mutagenesis of homologs according to the invention. The most frequently used techniques for the screening of large gene banks which are subject to analysis with high throughput comprise the cloning of the gene bank in replicable expression vectors, transformation of the suitable cells with the resulting vector bank and expression of the combinatorial genes under conditions under which the detection of the desired activity facilitates the isolation of the vector which encodes the gene the product whereof was detected. Recursive ensemble mutagenesis (REM), a technique which magnifies the frequency of functional mutants in the banks, can be used in combination with the screening tests in order to identify homologs (Arkin and Yourvan (1992) PNAS 89:7811-7815; Delgrave et al. (1993) Protein Engineering 6(3):327-331).

The invention further comprises the use of the 7β-HSDH wild type from *Collinsella aerofaciens* ATCC 25986, as described in the applicant's older international patent application WO2011/064404 (PCT/EP2010/068576), to which reference is hereby expressly made.

3. Nucleic Acids and Constructs 3.1 Nucleic Acids

Also a subject of the invention are nucleic acid sequences which code for an enzyme with 7β-HSDH, FDH, GDH and/or 3α-HSDH activity described herein and mutants thereof.

The present invention also relates to nucleic acids with a defined degree of identity to the specific sequences described herein.

"Identity" between two nucleic acids is understood to mean the identity of the nucleotides over the respective whole nucleic acid length, in particular the identity which is calculated by comparison by means of the Vector NTI Suite 7.1 Software from Informax (USA) with use of the clustal method (Higgins D G, Sharp P M. Fast and sensitive multiple sequence alignments on a microcomputer. Comput Appl. Biosci. 1989 April; 5(2):151-1) with setting of the following parameters:

Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |

| | |
|---|---|
| Window size | 5 |
| Number of best diagonals | 5 |

Alternatively to this, the identity can also be determined after Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13)3497-500, with the following parameters:

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single and double-strand DNA and RNA sequences, such as for example cDNA and mRNA) are producible in a manner known per se by chemical synthesis from the nucleotide building blocks, such as for example by fragment condensation of individual, overlapping, complementary nucleic acid building blocks of the double helix. The chemical synthesis of oligonucleotides can for example be effected in known manner according to the phosphoamidite method (Voet, Voet, $2^{nd}$ Edition, Wiley Press New York, pages 896-897). The attachment of synthetic oligonucleotides and filling of gaps by means of the Klenow fragment of DNA polymerase and ligation reactions and general cloning methods are described in Sambrook et al. (1989), Molecular Cloning: A laboratory manual, Cold Spring Harbor Laboratory Press.

Also a subject of the invention are nucleic acid sequences (single and double-strand DNA and RNA sequences, such as for example cDNA and mRNA) coding for one of the above polypeptides and functional equivalents thereof, which are for example accessible using artificial nucleotide analogs.

The invention relates both to isolated nucleic acid molecules which code for polypeptides or proteins according to the invention or biologically active segments thereof, and also nucleic acid fragments which can for example be used as hybridization probes or primers for the identification or amplification of coding nucleic acids according to the invention.

The nucleic acid molecules according to the invention can further contain untranslated sequences from the 3' and/or 5' end of the coding gene region.

The invention furthermore comprises the nucleic acid molecules complementary to the nucleic acid sequences specifically described or a segment thereof.

The nucleotide sequences according to the invention enable the creation of probes and primers which are usable for the identification and/or cloning of homologous sequences in other cell types and organisms. Such probes and primers usually include a nucleotide sequence region which under "stringent" conditions (see below) hybridizes to at least about 12, preferably at least about 25, such as for example about 40, 50 or 75 consecutive nucleotides of a sense strand of a nucleic acid sequence according to the invention or of a corresponding antisense strand.

An "isolated" nucleic acid molecule is separated from other nucleic acid molecules which are present in the natural source of the nucleic acid and can moreover be essentially free from other cellular material or culture medium, if it is produced by recombinant techniques or be free from chemical precursors or other chemicals, if it is chemically synthesized.

A nucleic acid molecule according to the invention can be isolated by standard molecular biological techniques and the sequence information provided according to the invention. For example, cDNA can be isolated from a suitable cDNA bank by using one of the specifically disclosed complete sequences or a segment thereof as a hybridization probe and standard hybridization techniques (such as for example described in Sambrook, J., Fritsch, E. F. and Maniatis, T. Molecular Cloning: A Laboratory Manual. $2^{nd}$ Edn., Cold Spring Harbor Laboratory, Cold Spring Harbor Laboratory Press, Cold Spring Harbor, N.Y., 1989). Moreover, a nucleic acid molecule comprising one of the disclosed sequences or a segment thereof can be isolated by a polymerase chain reaction wherein the oligonucleotide primers which were established on the basis of this sequence are used. The nucleic acid thus amplified can be cloned into a suitable vector and characterized by DNA sequence analysis. Further, the oligonucleotides according to the invention can be produced by standard synthetic methods, e.g. with an automatic DNA synthesizer.

Nucleic acid sequences according to the invention or derivatives thereof, homologs or parts of these sequences, can for example be isolated with normal hybridization methods or the PCR technique from other bacteria, e.g. via genomic or cDNA banks. These DNA sequences hybridize under standard conditions with the sequences according to the invention.

"Hybridize" is understood to mean the ability of a poly- or oligonucleotide to bind to a nearly complementary sequence under standard conditions, while under these conditions nonspecific bindings between non-complementary partners do not occur. For this, the sequences can be 90-100% complementary. The property of complementary sequences of being able to bind specifically to one another is for example exploited in the Northern or Southern Blot technique or in the primer binding in PCR or RT-PCR.

For the hybridization, short oligonucleotides of the conserved regions are advantageously used. However, longer fragments of the nucleic acids according to the invention or the complete sequences can be used for the hybridization. Depending on the nucleic acid used (oligonucleotide, longer fragment or complete sequence) or depending on which nucleic acid species DNA or RNA are used for the hybridization, these standard conditions vary. Thus for example the melting temperatures for DNA:DNA hybrids lie ca. 10° C. lower than those of DNA:RNA hybrids of the same length.

Standard conditions should be understood to mean, for example depending on the nucleic acid, temperatures between 42 and 58° C. are in an aqueous buffer solution with a concentration between 0.1 to 5×SSC (1×SSC=0.15 M NaCl, 15 mM sodium citrate, pH 7.2) or additionally in the presence of 50% formamide such as for example 42° C. in 5×SSC, 50% formamide. Advantageously, the hybridization conditions for DNA:DNA hybrids lie at 0.1×SSC and temperatures between about 20° C. to 45° C., preferably between about 30° C. to 45° C. For DNA:RNA hybrids, the hybridization conditions advantageously lie at 0.1×SSC and temperatures between about 30° C. to 55° C., preferably between about 45° C. to 55° C. These stated temperatures for the hybridization are melting temperatures calculated by way of example for a nucleic acid with a length of ca. 100 nucleotides and a G+C content of 50% in the absence of formamide. The experimental conditions for the DNA hybridization are described in relevant textbooks of genetics, such as for example Sambrook et al., "Molecular Cloning", Cold Spring Harbor Laboratory, 1989, and can be calculated according to formulae known to those skilled in the art for example depending on the length of the nucleic acids, the nature of the hybrids or the G+C content. Those skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The "hybridization" can in particular take place under stringent conditions. Such hybridization conditions are for example described in Sambrook, J., Fritsch, E. F., Maniatis, T., in: Molecular Cloning (A Laboratory Manual), $2^{nd}$ Edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are in particular understood to be: incubation at 42° C. overnight in a solution consisting of 50% formamide, 5×SSC (750 mM NaCl, 75 mM trisodium citrate), 50 mM sodium phosphate (pH 7.6), 5×Denhardt solution, 10% dextran sulfate and 20 g/ml denatured, sheared salmon sperm DNA, following by a washing step of the filter with 0.1×SSC at 65° C.

Also a subject of the invention are derivatives of the specifically disclosed or derivable nucleic acid sequences.

Thus, further nucleic acid sequences according to the invention can be derived for example from SEQ ID No.1, 3 or 7, and differ therefrom by addition, substitution, insertion or deletion of single or several nucleotides, but furthermore code for polypeptides with the desired property profile.

Also included according to the invention are those nucleic acid sequences which contain so-called silent mutations or are modified in accordance with the codon utilization of a specific source or host organism in comparison to a specifically mentioned sequence, just like naturally occurring variants, such as for example splice variants or allele variants thereof.

Also a subject are sequences obtainable by conservative nucleotide substitutions (i.e. the amino acid concerned is replaced by an amino acid of the same charge, size, polarity and/or solubility).

Also a subject of the invention are molecules derived from the specifically disclosed nucleic acids by sequence polymorphisms. These genetic polymorphisms can exist between individuals within a population because of natural variation. These natural variations usually cause a variance of 1 to 5% in the nucleotide sequence of a gene.

Derivatives of the nucleic acid sequences according to the invention should for example be understood to mean allele variants which display at least 60% homology at the derived amino acid level, preferably at least 80% homology, quite especially preferably at least 90% homology over the whole sequence region (concerning homology at the amino acid level reference may be made to the above explanations on the polypeptides). Over part regions of the sequences, the homologies can advantageously lie higher.

Furthermore, derivatives should also be understood to mean homologs of the nucleic acid sequences according to the invention, for example fungal or bacterial homologs, truncated sequences, or single-strand DNA or RNA of the coding and non-coding DNA sequence. Thus for example homologs at the DNA level possess a homology of at least 40%, preferably of at least 60%, particularly preferably of at least 70%, quite especially preferably of at least 80% over the whole stated DNA region.

Further, derivatives should also be understood to mean for example fusions with promoters. The promoters which are connected upstream of the stated nucleotide sequences can be modified by at least one nucleotide replacement, at least one insertion, inversion and/or deletion, without however the functionality or effectiveness of the promoters being impaired. Furthermore, the effectiveness of the promoters can be increased by modification in their sequence or they can also be completely replaced by more effective promoters of organisms of other species.

Furthermore, methods for creating functional mutants are known to those skilled in the art.

Depending on the technique used, those skilled in the art can introduce entirely random or also more targeted mutations into genes or else non-coding nucleic acid regions (which are for example important for the regulation of expression) and then generate gene banks. The molecular biological methods necessary for this are known to those skilled in the art and are for example described in Sambrook and Russell, Molecular Cloning. $3^{rd}$ Edition, Cold Spring Harbor Laboratory Press 2001.

Methods for the modification of genes and thus for modification of the protein encoded by these have long been familiar to those skilled in the art, such as for example site-specific mutagenesis, in which single or several nucleotides of a gene are exchanged (Trower M K (Publ.) 1996; In vitro mutagenesis protocols. Humana Press, New Jersey), saturation mutagenesis, in which at any site of a gene a codon for any amino acid can be exchanged or added (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Barik S (1995) Mol Biotechnol 3:1), error-prone polymerase chain reaction (error-prone PCR), in which nucleotide sequences are mutated by incorrectly operating DNA polymerases (Eckert K A, Kunkel T A (1990) Nucleic Acids Res 18:3739);

passaging of genes in mutator strains, in which for example because of defective DNA repair mechanisms an increased mutation rate of nucleotide sequences occurs (Greener A, Callahan M, Jerpseth B (1996) An efficient random mutagenesis technique using an E. coli mutator strain. In: Trower M K (Publ.) In vitro mutagenesis protocols. Humana Press, New Jersey), or DNA shuffling, in which a pool of closely related genes is formed and digested and the fragments are used as templates for a polymerase chain reaction, in which by repeated strand separation and reapproach, full-length mosaic genes in the end are created (Stemmer W P C (1994) Nature 370:389; Stemmer W P C (1994) Proc Natl Acad Sci USA 91:10747).

Using so-called directed evolution (described inter alia in Reetz M T and Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (Publ.) Manual of industrial microbiology and biotechnology. American Society for Microbiology), those skilled in the art can also create functional mutants in a targeted manner and also on a large scale. In this, in a first step gene banks of the relevant proteins are created, wherein for example the methods stated above can be used. The gene banks are expressed in a suitable manner, for example by bacteria or by phage display systems.

The relevant genes of host organisms which express functional mutants with properties which largely correspond to the desired properties, can be subjected to a further mutation round. The steps of the mutation and the selection or the screening can be repeated iteratively until the functional mutants present have the desired properties to a sufficient extent. Through this iterative mode of operation, a limited number of mutations, such as for example 1 to 5 mutations, can be performed stepwise and assessed and selected for their influence on the relevant enzyme property. The selected mutant can then be subjected to a further mutation step in the same manner. In this way, the number of individual mutants to be tested can be significantly decreased.

The results according to the invention yield important information with regard to the structure and sequence of the relevant enzymes which is necessary in order to generate deliberately further enzymes with desired modified properties. In particular, so-called "hot spots" can be defined, i.e. sequence segments which are potentially suitable for modifying an enzyme property through the introduction of targeted mutations.

3.2 Constructs

Also a subject of the invention are expression constructs containing a nucleic acid sequence coding for at least one polypeptide according to the invention under the genetic control of regulatory nucleic acid sequences, and vectors comprising at least one of these expression constructs.

According to the invention, an "expression unit" is understood to mean a nucleic acid with expression activity which includes a promoter, as defined herein, and after functional linkage with a nucleic acid or a gene to be expressed, regulates expression, namely the transcription and the translation of this nucleic acid or this gene. In this context, therefore, this is also described as a "regulatory nucleic acid sequence". In addition to the promoter, further regulatory elements, such as for example enhancers, can also be contained.

According to the invention, an "expression cassette" or "expression construct" is understood to mean an expression unit which is functionally linked with the nucleic acid to be expressed or the gene to be expressed. In contrast to an expression unit, an expression cassette thus comprises not only nucleic acid sequences which regulate transcription and translation, but also the nucleic acid sequences which are to be expressed as protein as a result of the transcription and translation.

In the context of the invention, the terms "expression" or "overexpression" describe the production or increasing of the intracellular activity of one or more enzymes in a microorganism which are encoded by the corresponding DNA. For this, for example a gene can be introduced into an organism, an existing gene be replaced by a different gene, the copy number of the gene or the genes be increased, a strong promoter be used, or a gene used which codes for a corresponding enzyme with a high activity, and these measures can optionally be combined.

Preferably, such constructs according to the invention comprise a promoter 5' upstream from the particular coding sequence and a terminator sequence 3' downstream, and optionally further normal regulatory elements, these each being operatively linked with the coding sequence.

According to the invention, a "promoter", a "nucleic acid with promoter activity" or a "promotor sequence" is understood to mean a nucleic acid which in functional linkage with a nucleic acid to be transcribed regulates the transcription of this nucleic acid.

In this connection, a "functional" or "operative" linkage is understood to mean for example the sequential arrangement of one of the nucleic acids with promoter activity and a nucleic acid sequence to be transcribed and optionally further regulatory elements, such as for example nucleic acid sequences which ensure the transcription of nucleic acids, and for example a terminator, in such a manner that each of the regulatory elements can fulfil its function in the transcription of the nucleic acid sequence. For this, a direct linkage in the chemical sense is not absolutely necessary. Genetic control sequences, such as for example enhancer sequences, can also exert their function on the target sequence from more distant positions or even from other DNA molecules. Arrangements in which the nucleic acid sequence to be transcribed is positioned behind (i.e. at the 3' end) of the promoter sequence, so that the two sequences are covalently bound to one another, are preferable. Here, the distance between the promoter sequence and the nucleic acid sequence to be transgenically expressed can be less than 200 base pairs, or smaller than 100 base pairs or smaller than 50 base pairs.

As well as promoters and terminator, as examples of further regulatory elements targeting sequences, enhancers, polyadenylation signals, selectable markers, amplification signals, replication origins and the like are to be mentioned. Suitable regulatory sequences are for example described in Goeddel, Gene Expression Technology: Methods in Enzymology 185, Academic Press, San Diego, Calif. (1990).

Nucleic acid constructs according to the invention comprise in particular sequence SEQ ID No.1, 3 or 7 or derivatives and homologs thereof, and the nucleic acid sequences derivable therefrom, which are advantageously operatively or functionally linked with one or more regulatory signals for controlling, e.g. increasing, the gene expression.

In addition to these regulatory sequence, the natural regulation of these sequences can still be present before the actual structural genes, and optionally have been genetically modified, so that the natural regulation has been silenced and the expression of the genes increased. The nucleic acid construct can however also be more simply incorporated, that is to say no additional regulatory signals were inserted before the coding sequence and the natural promoter with its regulation was not removed. Instead of this, the natural regulatory sequence is mutated so that regulation no longer takes place and the gene expression is increased.

A preferred nucleic acid construct advantageously also contains one or more of the already mentioned "enhancer" sequences, functionally linked with the promoter, which enable increased expression of the nucleic acid sequence. Also at the 3' end of the DNA sequences, additional advantageous sequences can be inserted, such as further regulatory elements or terminators. The nucleic acids according to the invention can be contained in one or more copies in the construct. Still further markers, such as genes complementing antibiotic resistances or auxotrophies can be contained in the construct, optionally for selection for the construct.

Examples of suitable regulatory sequences are contained in promoters such as cos-, tac-, trp-, tet-, trp-tet-, lpp-, lac-, lpp-lac-, lacI$^{q-}$, T7-, T5-, T3-, gal-, trc-, ara-, rhaP (rhaP$_{BAD}$) SP6-, lambda-P$_R$- or in the lambda-P$_L$ promoter, which are advantageously used in gram-negative bacteria. Further advantageous regulatory sequences are for example contained in the gram-positive promoters amy and SPO2, and in the yeast or fungal promotors ADC1, MFalpha, AC, P-60, CYC1, GAPDH, TEF, rp28 and ADH. Artificial promoters can also be used for the regulation.

For expression in a host organism, the nucleic acid construct is advantageously inserted into a vector, such as for example a plasmid or a phage which enables optimal expression of the genes in the host. Apart from plasmids and vectors, vectors should also be understood to mean all other vectors known to those skilled in the art, such as for example viruses, such as SV40, CMV, Baculovirus and Adenovirus, transposons, IS elements, phasmids, cosmids, and linear or circular DNA. These vectors can be autonomously replicated in the host organism or chromosomally replicated. These vectors represent a further configuration of the invention.

Suitable plasmids are for example in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The said plasmids are a small selection of the possible plasmids. Further plasmids are well known to those skilled in the art and can for example be taken from the book Cloning Vectors (Eds. Pouwels P. H. et al. Elsevier, Amsterdam-New York-Oxford, 1985, ISBN 0 444 904018).

In a further configuration of the vector, the nucleic acid construct according to the invention or the vector containing nucleic acid according to the invention can also advantageously be introduced into the microorganisms in the form of a linear DNA and be integrated into the genome of the host organism via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences in accordance with the specific "codon usage" used in the organism. The "codon usage" can easily be determined on the basis of computer evaluations of other, known genes of the relevant organism.

The production of an expression cassette according to the invention is effected by fusion of a suitable promoter with a suitable coding nucleotide sequence and a terminator or polyadenylation signal. Standard recombination and cloning techniques are used for this, such as are for example described in T. Maniatis, E. F. Fritsch and J. Sambrook, Molecular Cloning: A Laboratory Manual, Cold Spring Harbor Laboratory: Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which enables optimal expression of the genes in the host. Vectors are well known to those skilled in the art and can for example be taken from "Cloning Vectors" (Pouwels P. H. et al., Eds., Elsevier, Amsterdam-New York-Oxford, 1985).

4. Microorganisms

Depending on the context, the term "microorganism" can be understood to mean the starting microorganism (wild type) or a genetically modified, recombinant microorganism or both.

By means of the vectors according to the invention, recombinant microorganisms are producible which are for example transformed with at least one vector according to the invention and can be used for the production of the polypeptides according to the invention. Advantageously, the recombinant constructs described above are introduced into a suitable host system and expressed. In this, standard cloning and transfection methods known to those skilled in the art, such as for example coprecipitation, protoplast fusion, electroporation, retroviral transfection and the like, are preferably used to bring the said nucleic acids to expression in the particular expression system. Suitable systems are for example described in Current Protocols in Molecular Biology, F. Ausubel et al., Publ., Wiley Interscience, New York 1997, or Sambrook et al. Molecular Cloning: A Laboratory Manual. $2^{nd}$ Edn., Cold Spring Harbor Laboratory, Cold Spring Harbor Laboratory Press, Cold Spring Harbor, N.Y., 1989. An overview of bacterial expression systems for the heterologous expression of proteins has for example also been provided by Terpe, K. Appl. Microbiol. Biotechnol. (2006) 72: 211-222.

As recombinant host organisms for the nucleic acid according to the invention or the nucleic acid construct, in principle all prokaryotic or eukaryotic organisms are possible. Advantageously, microorganisms such as bacteria, fungi or yeasts are used as host organisms. Advantageously, gram-positive or gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia*, *Pseudomonas*, *Streptomyces*, *Nocardia*, *Burkholderia*, *Salmonella*, *Agrobacterium*, *Clostridium* or *Rhodococcus* are used. The genus and species *Escherichia coli* is quite especially preferable. Further advantageous bacteria are moreover to be found in the group of the alpha proteobacteria, beta proteobacteria or gamma proteobacteria.

The host organism or the host organisms according to the invention here preferably contain at least one of the nucleic acid sequences, nucleic acid constructs or vectors described in this invention, which code for an enzyme with 7β-HSDH activity according to the above definition.

The organisms used in the method according to the invention are grown or cultured depending on the host organism in a manner known to those skilled in the art. Microorganisms are as a rule grown in a liquid medium, which contains a carbon source mostly in the form of sugars, a nitrogen source mostly in the form of organic nitrogen sources such as yeast extract or salts such as ammonium sulfate, trace elements such as iron, manganese and magnesium salts and optionally vitamins. at temperatures between 0° C. and 100° C., preferably between 10° C. to 60° C. with oxygen aeration. During this, the pH of the nutrient liquid can be held to a fixed value, in other words be or not be regulated during the culturing. The culturing can be effected "batchwise", "semi-batchwise" or continuously. Nutrients can be provided at the start of the fermentation or be further supplied semicontinuously or continuously.

Until their use, the organisms according to the invention can be suitably stored, e.g. in the frozen state at −20° C.; or else also as lyophylizate. For use, frozen cultures are brought to room temperature; optionally, one or more freeze/thaw cycles can also be performed. Lyophilized preparations can for further use be dissolved/suspended in a suitable liquid medium, such as buffer solutions.

5. Production of UDCA $1^{st}$ Step: Chemical Conversion of CA to DHCA

The hydroxy groups of CA are oxidized for example with chromic acid or chromates in acid solution (e.g. $H_2SO_4$) to carbonyl groups in a manner known per se by the classical chemical route. As a result, DHCA is formed.

$2^{nd}$ Step: Enzymatic or Microbial Conversion of DHCA to 12-Keto-UDCA

In aqueous solution, DHCA is specifically reduced to 12-keto-UDCA by 3α-HSDH and 7β-HSDH or mutants thereof in the presence of NADPH or NADH respectively. The cofactor NADPH or NADH can be regenerated from isopropanol or sodium formate or glucose by an ADH or FDH or GDH or mutants thereof. The reaction proceeds under mild conditions. For example, the reaction can be performed at pH=6 to 9, in particular about pH=8 and at about 10 to 30, 15 to 25 or about 23° C.

In the case of a microbial conversion step, recombinant microorganisms which express the necessary enzyme activity(ies) can be cultured anaerobically or aerobically in suitable liquid media in the presence of the substrate to be converted (DHCA). Suitable culturing conditions are known per se to those skilled in the art. They comprise conversions in the pH range of for example 5 to 10 or 6 to 9, at temperatures in the range from 10 to 60 or 15 to 45 or 25 to 40 or 37° C. Suitable media comprise for example the LB and TB media described below. The conversion period here can for example take place batchwise or continuously or in other normal process variants (as described above). The conversion period here can for example lie in the range from minutes to several hours or days, and be for example 1 hr to 48 hrs. Optionally, if enzyme activity is not continuously expressed, this can be initiated by addition of a suitable inducer, after attainment of a target cell density, e.g. of about $OD_{600}$=0.5 to 1.0.

Further possible suitable modifications of the microbial production method as regards the operation of the fermentation, additions to the medium, enzyme immobilization and isolation of the valuable substances can also be taken from the following section concerning "Production of the enzymes and mutants".

$3^{rd}$ Step: Chemical Conversion of 12-Keto-UDCA to UDCA

The 12-carbonyl group of 12-keto-UDCA is removed by Wolff-Kishner reduction in a manner known per se, and as a result UDCA is formed from 12-keto-UDCA. In the reaction, the carbonyl group is first converted with hydrazine to the hydrazone. Next, the hydrazone is heated to 200° C. in the presence of a base (e.g. KOH), whereby nitrogen is eliminated and UDCA is formed.

6. Recombinant Production of the Enzymes and Mutants

Also a subject of the invention are methods for the recombinant production of polypeptides according to the invention or functional, biologically active fragments thereof, wherein a polypeptide-producing microorganism is cultured, optionally the expression of the polypeptides is induced, and these are isolated from the culture. The polypeptides can also be thus produced on a large industrial scale, if this is desired.

The microorganisms produced according to the invention can be cultured continuously or discontinuously in the batch process or in the fed batch process or repeated fed batch process. A summary of known culturing methods can be found in the textbook by Chmiel (Bioprozeβtechnik 1. Einführung in die Bioverfahrenstechnik [Bioprocess Technology 1. Introduction to Bioprocess Technology] (Gustav Fischer Verlag, Stuttgart, 1991)) or in the text book by Storhas (Bioreaktoren and periphere Einrichtungen [Bioreactors and Peripheral Equipment] (Vieweg Verlag, Braunschweig/Wiesbaden, 1994)).

The culture medium to be used has to appropriately satisfy the requirements of the particular strains. Descriptions of culture media for various microorganisms are contained in the American Society for Bacteriology manual "Manual of Methods for General Bacteriology" (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, saccharose, raffinose, starch or cellulose. Sugars can also be added to the media via complex compounds, such as molasses, or other by-products of sugar refining. It can also be advantageous to add mixtures of different carbon sources. Other possible carbon sources are oils and fats such as for example soya oil, sunflower oil, peanut oil and coconut fat, fatty acids such as for example palmitic acid, stearic acid or linolic acid, alcohols such as for example glycerin, methanol or ethanol and organic acids such as for example acetic acid or lactic acid.

Nitrogen sources are usually organic or inorganic nitrogen compounds or materials which contain these compounds. Example of nitrogen sources include ammonia gas or ammonium salts, such as ammonium sulfate, ammonium chloride, ammonium phosphate, ammonium carbonate or ammonium nitrate, nitrates, urea, amino acids or complex nitrogen sources, such as corn steep liquor, soya flour, soya protein, yeast extract, meat extract and others. The nitrogen sources can be used singly or as a mixture.

Inorganic salt compounds which can be contained in the media include the chloride, phosphate or sulfate salts of calcium, magnesium, sodium, cobalt, molybdenum, potassium, manganese, zinc, copper and iron.

As the sulfur source, inorganic sulfur-containing compounds such as for example sulfates, sulfites, dithionites, tetrathionates, thiosulfates, sulfides but also organic sulfur compounds, such as mercaptans and thiols, can be used.

As the phosphorus source, phosphoric acid, potassium dihydrogen phosphate or dipotassium hydrogen phosphate or the corresponding sodium-containing salts can be used.

Chelating agents can be added to the medium in order to keep the metal ions in solution. Particularly suitable chelating agents include dihydroxyphenols such as catechol or protocatechuate, or organic acids such as citric acid.

The fermentation media used according to the invention usually also contain other growth factors such as vitamins or growth promoters, which for example include biotin, riboflavin, thiamine, folic acid, nicotinic acid, panthothenate and pyridoxine. Growth factors and salts often derive from complex media components such as yeast extract, molasses, corn steep liquor and the like. Moreover, suitable precursors can be added to the culture medium. The exact composition of the media compounds depends strongly on the particular experiment and is individually decided for each specific case. Information on the media optimization is obtainable from the textbook "Applied Microbiol. Physiology, A Practical Approach" (Publ. P. M. Rhodes, P. F. Stanbury, IRL Press (1997) pp. 53-73, ISBN 0 19 963577 3). Growth media can also be obtained from commercial suppliers, such as Standard 1 (Merck) or BHI (Brain heart infusion, DIFCO) and the like.

All media components are sterilized, either by heat (20 mins at 1.5 bar and 121° C.) or by sterile filtration. The components can either be sterilized together or if necessary separately. All media components can be present at the start of the culturing or optionally be added continuously or batchwise.

The temperature of the culture normally lies between 15° C. and 45° C., preferably at 25° C. to 40° C. and can be kept constant or changed during the experiment. The pH of the medium should lie in the range from 5 to 8.5, preferably around 7.0. The pH for the culturing can be controlled during the culturing by addition of basic compounds such as sodium hydroxide, potassium hydroxide, ammonia or ammonia water or acidic compounds such as phosphoric acid or sulfuric acid. To control foaming, antifoaming agents, such as for example fatty acid polyglycol esters, can be used. To maintain the stability of plasmids, selectively acting substances, such as for example antibiotics, can be added to the medium. In order to maintain aerobic conditions, oxygen or oxygen-containing gas mixtures, such as for example ambient air, are introduced into the culture. The temperature of the culture normally lies at 20° C. to 45° C. The culturing is continued until a maximum of the desired product has formed. This target is normally reached within 10 hours to 160 hours.

The fermentation broth is then further processed. Depending on the requirement, the biomass can be entirely or partially removed from the fermentation broth by separation methods, such as for example centrifugation, filtration, decantation or a combination of these methods or entirely left in it.

The cells can also, if the polypeptides are not secreted into the culture medium, be disintegrated and the product obtained from the lysate by known protein isolation methods. The cells can be disintegrated optionally by high frequency ultrasound, by high pressure, such as for example in a French pressure cell, by osmolysis, by the action of detergents, lytic enzymes or organic solvents, by homogenizers or by combination of several of the stated methods.

Purification of the polypeptides can be achieved with known chromatographic methods, such as molecular sieve chromatography (gel filtration), such as Q sepharose chromatography, ion exchange chromatography and hydrophobic chromatography, and with other normal methods such as ultrafiltration, crystallization, salting out, dialysis and native gel electrophoresis. Suitable methods are for example described in Cooper, F. G., Biochemische Arbeitsmethoden [Biochemical Work Methods], Verlag Walter de Gruyter, Berlin, New York or in Scopes, R., Protein Purification, Springer Verlag, New York, Heidelberg, Berlin.

For the isolation of the recombinant protein, it can be advantageous to use vector systems or oligonucleotides, which elongate the cDNA by defined nucleotide sequences and thus code for modified polypeptides or fusion proteins, which for example serve for simpler purification. Suitable such modifications are for example so-called "tags" functioning as anchors, such as for example the modification known as hexa-histidine (SEQ ID NO: 22) anchors or epitopes which can be recognized as antigens by antibodies (described for example in Harlow, E. and Lane, D., 1988, Antibodies: A Laboratory Manual. Cold Spring Harbor (N.Y.) Press). These anchors can serve for attachment of the proteins onto a solid support, such as for example a polymer matrix, which for example can be packed in a chromatography column, or can be used on a microtiter plate or on another support.

At the same time, these anchors can also be used for the recognition of the proteins. For the recognition of the proteins, apart from this, normal markers, such as fluorescent dyes, enzyme markers, which after reaction with a substrate form a detectable reaction product, or radioactive markers, alone or in combination with the anchors, can be used for derivatization of the proteins.

7. Enzyme Immobilization

The enzymes according to the invention can be used free or immobilized in the methods described herein. An immobilized enzyme is understood to mean an enzyme which is fixed onto an inert support. Suitable support materials and the enzymes immobilized thereon are known from EP-A-1149849, EP-A-1 069 183 and DE-OS 100193773 and from the literature references cited therein. Reference is made in this respect to the disclosure of these texts in its entirety. Suitable support materials include for example clays, clay minerals, such as kaolinite, diatomaceous earth, perlite, silicon dioxide, aluminum oxide, sodium carbonate, calcium carbonate, cellulose powder, anion exchange materials, and synthetic polymers such as polystyrene, acrylic resins, phenol formaldehyde resins, polyurethanes and polyolefins, such as polyethylene and polypropylene. The support materials are normally used for production of the supported enzymes in a finely divided, particulate form, with porous forms being preferable. The particle size of the support material is usually not more than 5 mm, in particular not more than 2 mm (grading curve). Analogously, with use of the dehydrogenase as whole cell catalyst, a free or immobilized form can be selected. Support materials are for example Ca alginate, and carrageenan. Enzymes, and also cells, can also be directly crosslinked with glutaraldehyde (crosslinking to give CLEAs). Similar and further immobilization methods are for example described in J. Lalonde and A. Margolin "Immobilization of enzymes" in K. Drauz and H. Waldmann, Enzyme Catalysis in Organic Synthesis 2002, Vol.III, 991-1032, Wiley-VCH, Weinheim.

EXPERIMENTAL SECTION

A. General Information
1. Materials:

The genomic DNA of *Collinsella aerofaciens* DSM 3979 (ATCC 25986, former name *Eubacterium aerofaciens*) was obtained from the German Collection of Micro-organisms and Cell Cultures (DSMZ). UDCA and 7-keto-LCA are starting compounds known per se and described in the literature. All other chemicals and enzymes were commercially obtainable trade products of different manufacturers.

2. Microorganisms and Vectors:

| 2.1 Microorganisms | |
|---|---|
| *E. coli* BL21 (DE3) | F$^-$ ompT gal dcm lon hsdS$_B$ (r$_B^-$m$_B^-$)_(DE3 [lacI lacUV5-T7 gene 1 ind1 sam7 nin5]) |
| *E. coli* BL49 | F$^-$ ompT gal dcm lon hsdS$_B$ (r$_B^-$m$_B^-$)_(DE3 [lacI lacUV5-T7 gene 1 ind1 sam7 nin5]) hdhA::KanR |
| *E. coli* BLLiu (=*E. coli* BL21ΔhdhA) | F$^-$ ompT gal dcm lon hsdS$_B$ (r$_B^-$m$_B^-$) _(DE3 [lacI lacUV5-T7 gene 1 ind1 sam7 nin5]) _hdhA |
| *E. coli* NovaBlue (DE3) | endA1 hsdR17 (r$_{K12}^-$ m$_{K12}^+$) supE44 thi$^-$1 recA1 gyrA96 relA1lac [F' proA+B+ lacIqZ M15::Tn10 (Tc$^R$)] |

-continued

| 2.1 Microorganisms | |
|---|---|
| E. coli NB13 | endA1 hsdR17 ($r_{K12}^-$ $m_{K12}^+$) supE44 thi$^-$1 recA1 gyrA96 relA1lac [F' proA$^+$B$^+$ lacIqZ M15::Tn10 (Tc$^R$)] hdhA::KanR |

2.2 Expression Vectors and Vector Constructs

The expression plasmids (see FIG. 3)
p7(A)T3rG (=p7(A)T3rG-A) (see WO2012/080504)
p7(A)T3rG-K and
p7(A)T3TG (=p7(A)T3TG-A)
each have expression cassettes in which the genes 7β-HSDH, 3α-HSDH and GDH are encoded, but with different expression cassette structure and with different antibiotic resistances. These plasmids were used optionally in the host strain *E. coli* BL49 or *E. coli* BL21 ΔhdhA (both known from the applicant's WO 2012/080504 or WO 2011/147957).

The following strains thus modified were used:
*E. coli* BL49 p7(A)T3rG,
*E. coli* BL21 ΔhdhA p7(A)T3rG-K
*E. coli* BL49 p7(A)T3TG 3. Microbiological Methods Unless otherwise stated, molecular biological operations are performed on the basis of established methods, for example described in: Sambrook, J., Fritsch, E. F. and Maniatis, T. Molecular Cloning: A Laboratory Manual. 2$^{nd}$ Edn., Cold Spring Harbor Laboratory, Cold Spring Harbor Laboratory Press, Cold Spring Harbor, N.Y., 1989; Ausubel et al. (eds.), Current Protocols in Molecular Biology, John Wiley & Sons, N Y (1993); Kriegler, Gene Transfer and Expression, A Laboratory Manual, Stockton Press, NY (1990).

3.1 Culturing of *Escherichia coli* in Shaker Flask

For expression of recombinant proteins, firstly 5 mL LB medium with addition of the appropriate antibiotic was inoculated with a bacterial colony or a cryoculture and then incubated overnight at 30° C. and 200 rpm. On the next day, 100-200 mL TB medium with appropriate antibiotic were inoculated with 1-5 mL of the overnight culture and incubated at 37° C. and 250 rpm. On attainment of an OD600 of 0.6-0.8, expression of the recombinant protein was induced by addition of 1 mM IPTG and the culture incubated at 25° C. and 160 rpm for a further 21 hrs.

3.2 Culturing of *Escherichia coli* in the 7.5 L Stirred Vessel Reactor

The culturing of whole cell biocatalysts on the liter scale was effected in a stirred vessel reactor (V=7.5 L) from Infors AG (Infors 3, Bottmingen, Switzerland). The reactor was equipped with probes for temperature, pH and pO2, so that these parameters could be read off and optionally regulated by a control unit online. The reactor was temperature-controlled via a double jacket connected to the control unit. Aeration was effected via a dip tube and thorough mixing was effected by three six-blade impellers, which were driven by a motor on the reactor cover. In addition, substrate and base (ammonium hydroxide solution, 25% (w/v)) could be fed into the reactor via feed pumps.

Preculture

For the culturing in the 7.5 L stirred vessel reactor, a total of two preculture stages were applied. The first preculturing took place in a test-tube with 5 mL LB medium with the appropriate antibiotic. In the morning, this was inoculated with 100 μL of a cryoculture and incubated for 6-10 hrs at 30° C. and 200 rpm, until a visible turbidity appeared. Next, 500-1000 μL of the first preculture were transferred into a 1 L narrow-neck conical flask filled with 200 mL minimal medium after Wilms et al. (2001) which was incubated overnight at 37° C., 250 rpm (eccentricity 5 cm).

Batch Phase

For the stirred vessel culturing, a sterilized stirred vessel reactor filled with 2.8-3.8 L minimal medium and 1.5 mL antifoaming agent (Antifoam 204, Sigma-Aldrich, Munich) was used, whose probes were calibrated by standard methods before the start of culturing. This was treated with batch glucose (end concentration 2 g L$^{-1}$) and appropriate antibiotic and then inoculated with 200 mL of the second preculture stage. Aeration was performed at the start with 2 L min$^{-1}$ compressed air and the stirrer revolution rate at the start of the culturing was 200 rpm. On the pO2 falling below a threshold value of 30%, the stirrer revolution rate was increased incrementally by 5 rpm up to a theoretical maximum value of 1100 rpm. The pH was regulated to 7.0 unilaterally by addition of base (25% ammonium hydroxide, w/v), while the temperature was kept at 37° C. After consumption of the batch glucose, which could be identified by a sudden rise in the pO$_2$, the transition to the substrate-limited fed phase took place.

Substrate-Limited Growth Phase

At the start of the fed phase, the aeration with compressed air was increased to 5 L min$^{-1}$, the temperature reduced to 30° C. and the threshold value for the incremental stirrer revolution rate increase lowered to 20% pO2. The metering in of the substrate feed was effected on the basis of a specified growth rate of μ=0.15 hrs$^{-1}$. The feed medium contained 500 g L$^{-1}$ glucose and 99 g L$^{-1}$ diammonium hydrogen phosphate. The biomass yield was assumed to be 0.45 $g_{BDM}$ $g_{Glc}^{-1}$.

The duration of the substrate-limited growth phase was hrs. One hour before the end of this phase, the temperature was reduced to 20° C., further, 3 mL L$^{-1}$ trace element solution and 2 mL L$^{-1}$ magnesium sulfate solution (1 M) were added, each based on V0. If ampicillin was used as the selection antibiotic, 50 mg L$^{-1}$ ampicillin was also added at the start and also 1 hr before the end of the substrate-limited growth phase.

Expression Phase

After the end of the substrate-limited growth phase, at the start of the expression phase, addition of 0.5 mM IPTG (based on V0) took place. The temperature was held at 20° C. and the preset growth rate reduced to μ=0.06 hrs$^{-1}$. After 18 hrs, the feed volume flow was kept constant at the last adjusted value, since otherwise an oxygen saturation of pO2≥20% could not be ensure. A further addition of 3 mL L$^{-1}$ trace element solution, 2 mL L$^{-1}$ magnesium sulfate solution (1 M) and optionally 50 mg L$^{-1}$ ampicillin was effected 8 hrs after the start of the expression phase. The cells were harvested 24 hrs after the start of the expression phase, optionally treated with 30% glycerin (v/v) and stored at −20° C.

3.3 Culturing of *Escherichia coli* Libraries in Deep Well Plates

For the culturing of *E. coli* libraries in deep well plates, firstly a preculture was prepared in sterile microtiter plates with 96 wells. For this, 150 μL of preculture medium (TB medium treated with 5% (v/v) DMSO) were placed in each of the wells. Next, the wells were inoculated with colonies from agar plates by means of sterile toothpicks. The microtiter plates were then sealed with sterile, breathable sealing films (Breathe-Easy, Diversified Biotech, USA) and incubated overnight at 37° C. overnight at 200-250 rpm. After the incubation, the microtiter plates were stored sterile at −80° C. as stock plates. The protein expression was effected in sterile deep well plates with 96 wells at 2.2 mL well volume and square well apertures. For this, 600 µL sterile TB medium with the appropriate antibiotic were transferred into each well, then the wells were each inoculated with 10 µL preculture from the stock plate. The deep well plates were sealed with sterile, breathable sealing films and incubated at 37° C. for 9 hrs at 200-250 rpm. After 9 hrs incubation, the cultures were each treated with 100 µL induction solution. Next, the deep well plates were sealed with sterile, breathable sealing films and incubated at 30° C. for a further 21 hrs at 200-250 rpm. The cells were harvested by centrifugation (30 min, 3000 g). The cell pellets were stored at −80° C. until further use.

3.4 Strain Maintenance

The short and medium-term strain maintenance of *E. coli* was effected on LB agar plates with the appropriate selection antibiotics at 4° C. For long-term strain maintenance, cryo-cultures were prepared by growing *E. coli* cultures in LB medium and treating them in the exponential growth phase (OD≤0.8) with 20% sterile glycerin (v/v), and stored in sterile 1.5 mL reaction vessels at −80° C.

3.5 Cell Disintegration of *Escherichia coli* in the Vibration Mill

The cell disintegration of *E. coli* in the vibration mill was effected in 2 mL reaction vessels. For this, 1 mL of glass beads (diameter 0.25-0.5 mm, Carl Roth, Karlsruhe) and 1 mL of the bacterial suspension to be disintegrated were placed in each reaction vessel, which was then mounted in a vibration mill (MM 200, Retsch, Haan) and shaken for 6 mins at 30 Hz. Next, the vessels were centrifuged for 10 mins at 4° C. and 17880 g in a bench centrifuge (Biofuge Stratos, Thermo Fischer Scientific, Waltham, USA). The supernatant could be used for further applications.

3.6 Cell Disintegration of *Escherichia coli* in the High Pressure Homogenizer

Cells from cultures in the bioreactor were disintegrated with a high pressure homogenizer (Ariete, GEA Niro Soavi, Lubeck). For this, the cell suspension was firstly transferred into a 200 L stainless steel tank filled with 50 L potassium phosphate buffer (20 mM, pH 7.4) and cooled to 4° C. The disintegration was effected at a pressure of 950 bar and a volume flow of 300-350 L hr$^{-1}$, which after 15-20 mins was throttled to 150 L hr$^{-1}$. After the first passage, the cell broth was collected in a second 200 L stainless steel tank cooled to 4° C., cooled to below 20° C. and transferred into a third 200 L stainless steel tank filled with 50 L potassium phosphate buffer and cooled to 4° C. Next, a second passage through the high pressure homogenizer was performed as described above.

This procedure should ensure that the temperature of the cell broth during the disintegration does not exceed 35° C., since one passage through the high pressure homogenizer resulted in heating of the medium by 10-15° C. Following the cell disintegration, in a first step cell debris was separated with a disk separator (CAA 08, GEA Westphalia, Oelde). This was operated at a volume flow of 100 L hr$^{-1}$, a back-pressure of 0-3 bar and partial emptying interval of the solid ejectate of 999 secs. The clarified cell broth was aliquoted into 10 L plastic canisters and stored at −20° C. until further use.

3.7 Cell Disintegration of *Escherichia coli* with Lysozyme

For the enzymatic cell disintegration with lysozyme, pelleted cells were resuspended in deep well plates in 600 µL disintegration buffer (50 mM KPi, 10 mM MgCl$_2$, 70000 U mL$^{-1}$ lysozyme, 50 U mL$^{-1}$ DNAseI) and incubated for 1 hr at 37° C. Next, the cell debris was separated by centrifugation (30 mins, 3000 g, 4° C.) in a floor-standing centrifuge (Rotixa 50 RS, Hettich, Tuttlingen). The supernatant was used for further tests.

4. Molecular Biological Methods 4.1 Isolation of Plasmid DNA

The isolation of plasmid DNA was performed with the GenElute™ Plasmid Miniprep Kit (Sigma-Aldrich, Munich). For this, 5 mL of an LB overnight culture of *E. coli* was processed according to the manufacturer's instructions. For the elution of the isolated plasmid DNA, 100 µL of sterile, double-distilled water temperature-controlled to 70° C. were used.

4.2 Polymerase Chain Reaction

Polymerase chain reactions (PCR) for preparative amplification of DNA fragments were performed by the method of Saiki R. K. et al. Science, 239:487-491, 1988. The reaction mixture consisted of 1-2.5 µL template DNA, 0.5 µM of each oligonucleotide, 0.2 mM of each desoxyribonucleotide triphosphate (dNTPs) and 0.02 U µL$^{-1}$ Phusion DNA polymerase. The temperature program for the DNA amplification was based on the data from the polymerase manufacturer and the melting temperatures of the oligonucleotides.

4.3 Analytical and Preparative Agarose Gel Electrophoresis

For the separation of DNA molecules, agarose gels with a concentration of 1% agarose (w/v) were used. In this, 1 g of agarose was dissolved by boiling in 100 mL 1× TAE buffer, treated with 5 µL ethidium bromide (≥98%) or alternatively 5 µL Roti® GelStain (Carl Roth, Karlsruhe) and then poured into a gel chamber (C.B.S. Scientific, San Diego, USA). Before application, the DNA to be separated was treated with 5× agarose gel loading buffer according to Sambrook & Russell (2001) and applied onto the gel. A 100 bp DNA ladder extended (Carl Roth, Karlsruhe) was used as the length standard. The electrophoresis was effected in 1×TAE buffer at a constant voltage of 120 V.

4.4 Purification of DNA Fragments by Gel Extraction

For the purification of DNA fragments from agarose gels, the GenElute™ Gel Extraction Kit (Sigma-Aldrich, Munich) was used. This was performed according to the manufacturer's instructions. For the elution of the isolated DNA fragments, 50 µL of sterile, double-distilled water temperature-controlled to 70° C. were used.

4.5 Purification of DNA Fragments Using PCR Clean-Up Kit

The purification of DNA fragments with the GenElute™ PCR Clean-Up Kit (Sigma-Aldrich, Munich) was performed according to the manufacturer's instructions. For the elution of the purified DNA fragments 50 µL of sterile, double-distilled water temperature-controlled to 70° C. were used.

4.6 Restriction with Endonucleases

For the restriction of DNA, 40-45 µL of the DNA to be cleaved were treated with 10-20 U of the relevant restriction enzyme and incubated for 2 hrs at 37° C. in the reaction buffer with appropriate additives recommended by the manufacturer. Next, the fragments were purified either by agarose gel electrophoresis followed by gel extraction or using the PCR Clean-Up Kit.

4.7 Ligation of DNA Fragments

For the ligation of DNA fragments, previously already restricted and purified DNA fragments were used. The ligation was effected using 12 µL cleaved vector DNA, 4 µL cleaved insert DNA, and 20 U mL$^{-1}$ T4 DNA ligase (New England Biolabs, Frankfurt) with addition of 0.5 mM ATP in the buffer provided for this by the manufacturer at 16° C. Alternatively, the ligation was performed with the Quick Ligation™ Kit (New England Biolabs, Frankfurt) according to the manufacturer's instructions. In this, 6 µL of cleaved vector DNA and 3 µL of cleaved insert DNA were used.

4.8 Site-Directed Mutagenesis

Site-directed mutageneses on plasmid DNA were electively performed with a method according to Sanchis et al., *Appl. Microbiol. Biotechnol.*, 81(2):387-97, 2008 or Liu, H. & Naismith, J. H., *BMC Biotechnol.*, 8:91, 2008. If a saturation mutagenesis was to be performed, primers with degenerate codons were used. In the case of the method according to Sanchis et al., *Appl. Microbiol. Biotechnol.*, 81(2):387-97, 2008, the reaction mixture consisted of 0.4 µL template DNA, 0.1 µM of each oligonucleotide, 0.2 mM of each of the dNTPs and 0.02 U µL−1 of Phusion Hot Start DNA polymerase. The temperature program for the DNA amplification was based on the published methods and was merely adapted according to the information from the polymerase manufacturer and the melting temperatures of the oligonucleotides.

In the method according to Liu & Naismith (2008), the reaction mixture consisted of 0.2 µL template DNA, 1 µM of each oligonucleotide, 0.2 mM of each of the dNTPs and 0.02 U µL$^{-1}$ of Phusion Hot Start DNA polymerase. The temperature program for the DNA amplification was based on the published method and was merely adapted according to the information from the polymerase manufacturer and the melting temperatures of the oligonucleotides. Following the mutagenesis PCR, the parental DNA was restricted by twice consecutively adding DpnI, 0.5 U µL$^{-1}$ each time, and then incubating for 1 hr at 37° C.

4.9 Production and Transformation of Chemically Competent Cells

For the production of chemically competent *E. coli* cells, a 100 mL LB liquid culture in the exponential growth stage (OD 0.5) was transferred into 50 mL reaction vessels and pelleted by centrifugation (3220 g, 4° C., 10 mins). The supernatant was then discarded, the cell pellet resuspended in 40 mL of ice-cooled TFB1 medium and incubated for 15 mins on ice. After this, the cells were again pelleted by centrifugation (3220 g, 4° C., 10 min), the supernatant discarded, the cells resuspended with 4 mL of ice-cooled TFB2 medium and incubated for a further 15 mins on ice. Next, 200 µL aliquots were placed in sterile 1.5 mL reaction vessels and frozen at −80° C. For the transformation, in each case an aliquot was thawed, treated with 1-10 µL DNA solution and incubated for 45 mins on ice. After a heat shock (42° C., 1:30 mins) in the Thermomixer (RiO, QUANTIFOIL Instruments, Jena) the cells were again kept on ice for 1-2 mins. Next, 600 µL of sterile LB medium were added, and the mixture incubated in the Thermomixer for a further 45 mins at 37° C. and 600 rpm. After mild centrifugation (3000 rpm, 1 min), the supernatant was discarded apart from 50-100 µL, and the pellet resuspended in the remaining supernatant, and plated out onto appropriate agar plates. This was then incubated in the incubator overnight at 37° C.

4.10 Production and Transformation of Electrocompetent Cells

For the production of electrocompetent *E. coli* cells, a 200 mL LB liquid culture in the exponential growth phase (OD 0.5) was transferred into ice-cooled 50 mL reaction vessels, incubated for 20 mins on ice and pelleted by centrifugation (4000 g, 4° C., 15 mins). The cells were then washed three times by successively resuspending the pellet in 200 mL, 100 mL and 8 mL of ice-cooled 10% glycerin solution (v/v) and again pelleting by centrifugation (6000 g, 4° C., 15 mins). Next, the cells were resuspended to a total volume of 0.4-0.8 mL with ice-cooled 10% (v/v) glycerin and filled in aliquots of 20 µL in ice-cooled, sterile 1.5 mL reaction vessels and frozen at −80° C.

For the transformation, the cells were treated with 2-10 µL of deionized DNA solution and electroporated in electroporation cuvettes with a 1-2 mm electrode gap according to the electroporator manufacturer's protocol (Gene Pulser Xcell™, Bio-Rad, Munich.) Next, 1 mL of LB medium was immediately added to the cells, and the suspension transferred into sterile 1.5 mL reaction vessels and incubated for 60 mins at 37° C. and 600 rpm in the Thermomixer (RiO, QUANTIFOIL Instruments, Jena). After a mild centrifugation (3000 rpm, 1 min) the supernatant was discarded except for 50-100 µL, and the pellet resuspended in the remaining supernatant and plated out onto appropriate agar plates. These were then incubated overnight at 37° C. in the incubator.

4.11 Colony Polymerase Chain Reaction

Preparative colony polymerase chain reactions (colony PCR) were performed in order to isolate the gene for the glucose dehydrogenase from *Bacillus subtilis*. The procedure corresponds to that stated in Section 4.2, with the modification that instead of template DNA a bacterial swab from a single colony cultured on agar plates was added to the reaction mixture. Analytical colony PCR were used to check for correct ligation. Here also, a swab of a single bacterial colony was used as the template. Primers for the colony PCR were selected such that these hybridize to the target DNA with regions flanking the insertion site, so that on the basis of the length of the amplification product it is possible to estimate whether the insertion was successful. The reaction mixture consisted of 0.5 µM of each oligonucleotide, 0.2 mM of each of the dNTPs and 0.05 U µL$^{-1}$ Taq DNA polymerase. The temperature program for the DNA amplification was based on the polymerase manufacturer's instructions and the melting temperatures of the oligonucleotides.

4.12 Specific Silencing of Chromosomal Genes

The specific silencing of the chromosomal 7α-HSDH in *E. coli* was effected by means of the kit TargeTron™ Gene Knockout System from Sigma Aldrich (Munich). The plasmid pMB13 needed for the silencing is described in Braun, M., PhD thesis, Technische Universität Munich, 2011. This plasmid was transformed into chemically competent *E. coli* and the silencing of the target gene performed according to the manufacturer's instructions. By selection on LB agar plates with kanamycin and colony PCR, the successful silencing could be detected. In order to remove the plasmid remaining in the bacterium, the cells were cultured overnight at 37° C. in LB medium with kanamycin (50 mg L$^{-1}$) and novobiocin (62 mg L$^{-1}$). Next, the culture was plated out onto LB agar plates with kanamycin and incubated overnight at 37° C. The presence of the plasmid to be removed was tested for by testing individual colonies for chloramphenicol sensitivity. This was effected in parallel overnight culturing at 37° C. in LB medium, once with addition of 33 mg L$^{-1}$ chloramphenicol, and once without addition thereof.

5. Protein Chemical Methods

5.1 Purification of Proteins on the mL Scale

The purification of the proteins on the mL scale was effected according to the principle of immobilized metal affinity chromatography (IMAC). The separation principle is based on the specific interaction of matrix-bound metal ligands with histidine residues on the target protein to be purified. For this purpose, a His6 (SEQ ID NO: 22) anchor is fused either N— or C-terminally during the expression of the target protein. For the purification on the Fast Protein Liquid Chromatography (FPLC) unit, HisTrap columns (1 mL or 5 mL column volume) the agarose matrix whereof was loaded with Ni2+ ions were used. The flow rates of the mobile phase were in each case set at one column volume (CV) per minute. During this, the protein concentration in the eluate stream could be monitored through the UV extinction at 280 nm. Firstly, the columns were equilibrated with at last 5 CV of binding buffer, and the samples were then applied. After this, the column was washed with binding buffer to remove nonspecifically-binding foreign proteins. The washing was performed until a base line of the UV signal was again attained. The elution of the target protein was achieved by a linearly rising elution buffer gradient from 0% to 100% over 20 mins, during which eluate fractions each of 2 CV were collected. The fractions which contain the target protein can be identified via the UV signal. Next, the column was again washed with 10 CV of elution buffer. The fractions containing the target protein were then concentrated via Vivaspin centrifugal concentrators (exclusion size 10 kDa) the buffer changed by filling with the target buffer and concentrating three times. As a rule, the target buffer corresponded to the reaction buffer needed for the further use of the protein.

For the purification with centrifugal units, HisPur™Ni-NTA Resin Spin Columns (Thermo Fischer Scientific, Waltham, USA) with a bed volume of 3 mL were used. The procedure for this corresponded to the manufacturer's instructions. The concentration and buffer change corresponded to the procedure previously described.

5.2 Purification of Proteins on the L Scale

The purification of proteins on the L scale was also effected on the basis of IMAC. For this, a chromatography column of 600 mL volume and diameter 50 mm, which was filled with Ni Sepharose 6 Fast Flow (GE Healthcare Life Science, Uppsala, Sweden) was used. Before packing, the column material stored in 20% ethanol was washed by threefold decantation, refilling with water, slurrying and sedimentation. Next, the slurried medium was fed into the empty column and the column packed at a maximum flow rate of 150 mL min$^{-1}$ and a maximum pressure of 1.5 bar. The finished packed column was then equilibrated with 5 CV of binding buffer at a maximum pressure of 1.2 bar. After thawing, the sample to be applied was firstly treated with 500 mM NaCl and adjusted to pH 7.4 with 1 M NaOH. Next, a cross-flow filtration was performed with two Sartocon® Slice Hydrosart® filter cassettes (0.2 µm exclusion size, 0.1 m2 filter area each, Sartorius Stedim Biotech, Göttingen) with sterile filters connected in series (0.2 µm exclusion size), in order to clarify the sample. The samples were then applied onto the column with a maximum pressure of 1.2 bar against the direction of elution. Next, the column was washed with binding buffer in the direction of elution, until the UV signal of the eluate stream again showed a baseline. The elution of the protein was effected via a elution buffer gradient linearly rising from 0% to 100% over 180 mins, during which fractions of 2 L each were collected. The fractions which contain the target protein could be identified through the UV signal of the detector. These fractions were then firstly concentrated by cross-flow filtration with two Sartocon® Slice Hydrosart® filter cassettes (10 kDa exclusion size, 0.1 m2 filter area each, Sartorius Stedim Biotech, Göttingen), and then rebuffered by diafiltration with a 5-10-fold exchange volume of target buffer.

5.3 Sodium Dodecylsulfate Polyacrylamide Gel Electrophoresis (SDS-PAGE)

The analytical separation of protein mixtures was effected by discontinuous sodium dodecylsulfate polyacrylamide gel electrophoresis (SDS-PAGE) with 12.5% separation and 3% collection gel (Laemmli, U. K., Nature, 227 (5259); 680-5, 1970; Fling, S. P. & Gregerson, D. S., Anal. Biochem., 155(1):83-8, 1986. For the separation gel, 17.5 mL distilled water was mixed with 10 mL separation gel buffer (4×) and 12.5 mL acrylamide (40%) and the polymerization started with 100 µL ammonium persulfate (APS, 10%) and 10 µL tetra-methylethylenediamine (TEMED). The composition of the collection gel consists of 15 mL distilled water, 20 mL collection gel buffer (2×), 5 mL acrylamide (40%), 100 µL APS and 10 µL TEMED. Before application, protein samples were treated with Laemmli buffer and incubated for 5 mins at 95° C. in order to denature the proteins. Next, these were applied onto the gel, Roti®-Mark standard (14-212 kDa, Carl Roth, Karlsruhe) was used as the size standard. The electrophoresis was effected in an electrophoresis chamber (PEQLAB, Erlangen) with Rotiphorese® SDS-PAGE (Carl Roth, Karlsruhe) as mobile phase at a constant current of 30 mA per gel. For staining the protein bands, Roti®-Blue dye solution (Carl Roth, Karlsruhe) was used according to the manufacturer's instructions.

5.4 Protein Concentration Determination by Bicinchoninic Acid Assay (BCA Assay)

Total protein concentrations were measured with the Pierce™ BCA Protein Assay Kit (Thermo Scientific, Rockford, USA) according to the manufacturer's instructions. As the protein standard, a standard of bovine serum albumin (BSA) contained in the kit was used.

5.5 Determination of Enzyme Activities in the Microtiter Plate Photometer

Enzyme activity determinations were performed at 30° C. in the microtiter plate photometer with a sample volume of 250 µL, in which the change in the NAD(P)H concentration ($\varepsilon$ 340=6.22 mL µmol$^{-1}$ cm$^{-1}$) was monitored at a wavelength of $\lambda$=340 nm. Here, the activities were determined by linear regression in the part of the reaction proceeding linearly. For this, the sample to be tested was appropriately diluted with potassium phosphate buffer (50 mM, pH 8.0) and treated with substrate and cofactor. The final concentrations of substrate and cofactor were 10 mM DHCA and 100 µM NADPH for 7β-HSDH, 10 mM DHCA and 100 µM NADH for 3α-HSDH, and 200 mM glucose and 1000 µM NAD(P) for GDH.

All substrates and cofactors were dissolved in potassium phosphate buffer (50 mM, pH 8.0). All measurements were performed in triplicate, then the mean value was determined. In the determination of the artificial units (AU) for the mechanistic modeling of the multi-enzymatic reduction of DHCA to 12-keto-UDCA, the protocol for the enzyme activity determination was modified. In this, as the reaction buffer a potassium phosphate buffer (100 mM, pH 7.0), into which 20% (v/v) glycerin, 0.6% (w/v) BSA and 0.006% (v/v) Antifoam 204 (Sigma-Aldrich, Munich) had been mixed, was used. The concentrations of substrate and cofactor were 500 µM DHCA and 200 µM NADH for 3α-HSDH, 500 µM DHCA and 200 µM NADPH for 7β-HSDH and 200 mM glucose and 1000 µM NAD for GDH. The enzymes were used in dilutions at which the measured initial extinction change was in the range 0.0005-0.0020 s$^{-1}$ with GDH and 0.00025-0.00100 s$^{-1}$ with HSDH. All measurements were performed in octuplicate, then the 25% truncated mean value determined. Here an AU is defined as the quantity of active enzyme which under these stated reaction conditions catalyzes the conversion of 1 µmol substrate or cofactor within 1 min.

6. Analytical Methods

6.1 Determination of the Optical Density of Bacterial Suspensions

The optical density of E. coli suspensions was measured in a cuvette photometer in cuvettes of 1 cm layer thickness at a wavelength of λ=600 nm. The bacterial suspension was optionally diluted with appropriate medium or buffer, so that the measured extinction did not exceed 0.5.

6.2 Determination of the Dry Biomass Concentration of Bacterial Suspensions

Unless otherwise stated, the dry biomass concentration was determined gravimetrically. For this, 1 mL of the relevant bacterial suspension was placed in predried and preweighed 1.5 mL reaction vessels, then the cells were pelleted in a bench centrifuge at 13000 rpm for 10 mins at room temperature and the supernatant discarded. After this, the vessels were dried to constant weight and again weighed. The dry biomass concentration could then be calculated by means of the following equation.

$$c_X = (m_{full} - m_{empty})/V$$

with:
$c_X$=dry biomass concentration, gBDM $L^{-1}$
$m_{full}$=mass of the reaction vessel filled with sample material after the drying, g
$m_{empty}$=mass of the empty reaction vessel after the drying, g
V=volume of the cell suspension before the sedimentation, L

6.3 Photometric Determination of Cofactor Concentrations

Concentrations of NAD(P) and NADP(H) were determined photometrically in a cuvette photometer according to the Lambert-Beer law. For this, a quartz cuvette (Hellma Analytics, Mülheim) with a layer thickness of 1 cm was used, which was filled with 1 mL sample. The determination of the NAD(P) concentration was performed at a wavelength of λ=259 nm, wherein the molar extinction coefficient was $\varepsilon_{259\,nm}$=16.9 mL $\mu mol^{-1}$ $cm^{-1}$. The concentrations of NAD(P)H were determined at a wavelength of λ=340 nm, and here the molar extinction coefficient was $\varepsilon_{340\,nm}$=6.22 mL $\mu mol^{-1}$ $cm^{-1}$.

6.4 High Performance Liquid Chromatography (HPLC)

The qualitative and quantitative analysis of bile salts was effected by separation of the substances by HPLC. For this, the HPLC system Finnigan Surveyor Plus (Thermo Fischer Scientific, Waltham, USA) with a reverse phase chromatography column of the type Hibar® 125-4 RP-18e (5 μm) (Merck, Darmstadt) was used. As the mobile phase, a mobile phase mixture of aqueous phosphoric acid (pH 2.6) and acetonitrile was used, and for the separation a mobile phase gradient was used. The flow rate of the mobile phase is 1 mL $min^{-1}$ and in each case 20 μL of sample was injected. The bile salts were detected by UV extinction at λ=200 nm. The method was calibrated with reference substances by standard methods.

The gradient profile was as follows:
0-3 mins: constant acetonitrile content of 35% (v/v), 3-7 mins: linear increase in the acetonitrile content to 39% (v/v), 7-8 mins: linear increase in the acetonitrile content to 70% (v/v), 8-9.5 mins: constant acetonitrile content of 70% (v/v), 9.5-10.5 mins: linear decrease in the acetonitrile content to 35% (v/v), 10.5-14 mins: constant acetonitrile content of 35% (v/v).

6.5 Flow Cytometry (FACS)

Flow cytometry (fluorescence-activated cell sorting, FACS) was used to investigate the cell integrity of whole cell biocatalysts. For this, the cells were diluted with PBS to a particle density of ca. 109 $mL^{-1}$, which at a flow rate of 1 mL $s^{-1}$ corresponds to 1000 signals $s^{-1}$. These cells were treated with 0.75 mM of the dye bis-(1,3-dibutylbarbituric acid)-trimethin-oxonol (Dibac4[3]), which overcomes depolarized cell membranes and creates an increased fluorescence by binding to intracellular proteins and membranes. By plotting the Dibac4[3]-mediated fluorescence against the light scattering of the particles, which is an indicator of the particle size, inferences could be drawn concerning the cell integrity (Suller, M. T.& Lloyd D., Cytometry, 35(3):235-41, 1999; Langemann et al., Bioeng. Bugs, 1(5):326-36, 2010).

6.6 Standardized Test Method for Determination of the Enzymatic Conversion of DHCA to 12-Keto-UDCA (IPC Method)

a. Equipment

Apparatus: HPLC with UV detector and autosampler (Merck Hitachi, LaChrom Elite (high pressure gradient system) or comparable);

Column: Merck, Purospher® STAR RP-18e, 125 mm×4.0 mm, 5 μm, Art. #5I0 036; or comparable b. Reagents Suitable for Gradient Creation

| Acetonitrile | Merck LiChroSolv ® |
| Water | ultrapure water |
| $H_3PO_4$ | orthophosphoric acid 85.0%; Merck |
| Methanol | Merck LiChroSolv ® | c. HPLC Parameters

| Flow rate | 1.0 ml/min |
| Column temperature | 25° C. |
| Injection volume | 20 μl |

Gradient

| Time (mins) | Eluent A (%) | Eluent B (%) | Curve |
| --- | --- | --- | --- |
| 0.0 | 80.0 | 20.0 | — |
| 15.0 | 65.0 | 35.0 | linear |
| 20.0 | 65.0 | 35.0 | linear |
| 21.0 | 15.0 | 85.0 | linear |
| 30.0 | 15.0 | 85.0 | linear |
| 31.0 | 80.0 | 20.0 | linear |
| 36.0 | 80.0 | 20.0 | linear |

| Detection | UV 200 nm |
| Run time | 36.0 mins |
| Washing | methanol/water: 9/1 (v/v) | d. Preparation of the Solutions and Samples

Mobile Phase A $H_2O$ (adjusted to pH 2.6 with $H_2PO_4$ (85%))

Mobile Phase B acetonitrile

| Blank | diluent: methanol/water: 9/1 (v/v) |

System Suitability Solution (SST) 5.00 mg DHCA, 5.00 mg 12-keto-UDCA, 5.00 mg 3,12-diketo-UDCA and 5.00 mg 7,12-diketo-CA (each precisely weighed out) in 10.0 ml diluent Test solution 1 ml reaction solution, diluted with 9 ml diluent; ultrasonicated at room temperature and centrifuged for 10 mins.

e. Procedure
Analytical Sequence:

| Blank | 1 x injection |
|---|---|
| System Suitability Solution (SST) | 1 x injection |
| Test solution | 2 x injection |
| Blank | 1 x injection |

Regeneration:

After each sequence, the column is regenerated with methanol/water (4/6 to 9/1 (v/v)).

The column is then rinsed with acetonitrile/water (4/6 (v/v)).

f. Evaluation

Determination of the retention times (Rt) of the compounds from analysis of the SST sample.

% area analysis of
DHCA (educt)
12-keto-UDCA (product)
3,12-diketo-UDCA (intermediate)
7,12-diketo-CA (intermediate)
Retention Times:

| Analyte | ca. RT (min) | RRT |
|---|---|---|
| 12-keto-UDCA | 13.9 | 1.00 |
| 3,12-diketo-UDCA | 14.5 | 1.04 |
| 7,12-diketo-CA | 16.5 | 1.18 |
| DHCA | 17.9 | 1.28 |

RT: Retention time
RRT: Relative Retention time

7. Stereoselective Reduction of Dehydrocholic Acid 7.1 Batch Reduction on the 2 mL Scale Batch reductions on the 2 mL scale were performed as validation experiments for the mechanistic modeling of the multienzymatic reduction of DHCA to 12-keto-UDCA. For this, deep well plates with square well apertures and V-shaped bottoms with a nominal volume of 2.0 mL per well were used. For thorough mixing, the deep well plates were shaken on a laboratory shaker at 500 rpm. To ensure constant temperature, the whole apparatus was located in an incubation cabinet temperature-controlled at 30° C. The reaction mixtures, consisting of DHCA, NAD, NADP, 3α-HSDH, 7β-HSDH and GDH were present in potassium phosphate buffer (100 mM, pH 7.0) with addition of 0.6% ((w)/v) BSA and were placed directly in the wells. The reaction was started by addition of glucose solution, followed by threefold inversion of the deep well plate. Enzymes which had been purified according to Section 5.2 were used. Sampling took place half-hourly by withdrawal of 100 μL of reaction mixture, which was treated directly with 900 μL methanol (77%, v/v). The methanol-treated samples were then mixed by vortexing and centrifuged for 10 mins at 13000 rpm in a bench centrifuge at room temperature. The supernatant was then analyzed by HPLC. All reactions were performed in triplicate.

7.2 Batch Reduction on the 20 mL Scale

Stereoselective reductions of DHCA on the 20 mL scale were effected in narrow neck screw-cap bottles (DURAN Group, Wertheim/Main) with a nominal volume of 50 mL, an internal diameter of 41 mm and a GL32 screw-cap thread. Thorough mixing was provided by a cross-shaped magnetic stirrer at 450 rpm, which was driven by a multiple stirrer plate (Variomag Multipoint, Thermo Scientific, Waltham, USA). To ensure constant temperature, the whole apparatus was located in an incubation cabinet temperature-controlled. For the reaction mixtures, the substrate DHCA was firstly predissolved with an equimolar quantity of NaOH. The reaction mixture, consisting of DHCA, cosubstrate (glucose or formate), and optionally further additives such as NAD (P), glycerin and $MgCl_2$ was mixed together before the start of the reaction. Potassium phosphate (50 mM) was used as the buffer and the pH was adjusted to the desired value as necessary with sodium hydroxide solution, phosphoric acid or formic acid (each 5 M). The reaction was started by the addition of whole cell biocatalysts. During the reaction, the pH was measured at 30 minute intervals with a manual pH-meter (pH-Tester Checker®, Carl Roth, Karlsruhe) and adjusted to the starting value as necessary with sodium hydroxide solution, phosphoric acid or formic acid (each 5 M). Sampling was performed at intervals of 30 or 60 minutes, by withdrawal of 300 μL of reaction mixture and mixing with 700 μL methanol (≥99.9%). Next, the sample-methanol mixture was diluted 3:10 with 70% methanol (v/v) and centrifuged for 10 mins at 13000 rpm in a bench centrifuge at room temperature. A sample was taken from the supernatant and diluted 1:10 with methanol (70%, v/v), placed in test-tubes and analyzed by HPLC. All reactions were performed in triplicate.

7.3 Batch Reduction on the 1 L Scale

Stereoselective reductions of DHCA on the 1 L scale were performed in a 1.5 L stirred vessel reactor from Infors AG (Infors 3, Bottmingen, Schweiz) without baffles. The reactor was equipped with sensors for temperature and pH, so that these parameters could be read off from a control unit online and optionally regulated. The reactor was temperature-controlled via a double jacket connected to the control unit and thorough mixing was effected by two six-blade impellers at 500-1000 rpm, which were driven by a motor on the reactor cover. In addition, acid (phosphoric acid, 5 M) or base (sodium hydroxide solution, 5 M) for pH regulation could be fed into the reactor via feed pumps. The substrate DHCA was either predissolved in equimolar sodium hydroxide solution or added directly as free acid in powder form. All other components were also added either as solid or as stock solution. After filling to the appropriate volume and setting of the desired pH, the reaction was started by addition of whole cell biocatalysts. Samples were taken at intervals of 30 or 60 mins as described in Section 7.2.

7.4 Isolation of Bile Salts by Acid Precipitation

The isolation of bile salts is based on the low solubility of bile salts in their protonated form at acidic pH. For this, a mixture with dissolved bile salts in the stirred state is titrated dropwise with hydrochloric acid (6 M) to pH≤2.0. During this, the dissolved bile salts almost completely precipitate out as solid. This was then separated from the residual solution by means of a Buchner funnel with inserted filter paper (diameter 150 mm, retention range ≥4 μm). If necessary, the bile salt could be washed by placing it in ultrapure water and dissolving it by titration with sodium hydroxide solution (5 M) to pH 8-9, filtering with the Buchner funnel and then again isolating by acid precipitation. For the preparation of 7,12-diketo-UDCA and 12-keto-UDCA, a twofold washing procedure was effected, and for the preparation of 3,12-diketo-UDCA the washing procedure was effected once. Next, the isolated bile salt was dried to constant weight at 60° C.

8. Standardized Test Procedure for the Conversion of Dehydrocholic Acid (DHCA) to 12-Keto-Ursodeoxycholic Acid (12-Keto-UDCA) with Whole Cell Catalyst (with 3α-HSDH, 7β-HSDH and GDH Activity)

8.1 Reagents $K_2HPO_4$*3 $H_2O$ (≥99%, p.a.); Roth
$KH_2PO_4$ (crystalline, puriss.); Merck $C_6H_{12}O_6 \cdot H_2O$ (≥99.5%, Ph. Eur.); Roth
$MgCl_2 \cdot 6H_2O$ (≥99%, p.a.); Roth
DHCA: PharmaZell
β-NAD: Roth
β-NADP-Na$_2$: Merck,
Whole cell catalyst (with 3α-HSDH, 7β-HSDH and GDH activity) stored at −20° C.)
HCl (37%)
NaOH (10%)

8.2 Production of the Buffer Solution (Stock Solution)

For the production of the buffer stock solution, 2.54 g of dipotassium hydrogen phosphate trihydrate and 0.18 g of potassium dihydrogen phosphate are successively weighed out and dissolved in 1000 ml deionized water; pH of the solution: 7.8 at 25° C.

8.3 Production of the NAD/NADP Solution (Stock Solution)

For the production of the NAD/NADP stock solution, 158 mg β-NADP-Na$_2$ and 663 mg β-NAD are successively weighed out into a 1000 ml volumetric flask, made up to volume with deionized water and dissolved.

8.4 Whole Cell Catalyst Sample Preparation (Cell Suspension)

Before withdrawal of the cell suspension, the sample must be warmed to room temperature (RT). Duration of the warming ca. 30 mins to ca. 3 hours.

8.5 Reaction Mixture (Whole Cell Conversion and DHCA to 12-Keto-UDCA)

180 ml of the aforesaid buffer stock solution are prewarmed to 26-28° C. in the conical flask. Next, 13.87 g (0.07 mol) of α-D(+)-glucose monohydrate in the 250 ml three-necked flask are dissolved with ca. ⅔ of the volume of the prewarmed buffer. 5.64 g (0.014 mol) of dehydrocholic acid (DHCA) together with the remaining buffer suspended in the glucose buffer solution and warmed to 26-28° C. on the water-bath, during which the pH already decreases and is adjusted to 6.8. Without delay, 36 mg (0.18 mmol) of magnesium chloride hexahydrate, 10 ml of the NAD/NADP stock solution and 5 ml of thawed cell suspension are successively added to the suspension.

The reaction suspension is stirred on the water-bath for 8 hrs (at 26-28° C.) With use of a pH-meter and manual pH control (titration with 10% NaOH solution), the pH of the suspension should always lie between 6.70 and 6.90. With the alternative use of a pH-stat, the pH should always lie at 6.8.

8.6 HPLC Analysis

After 0.5 hrs, 1 hr, 1.5 hrs, 2 hrs, 2.5 hrs, 3 hrs, 4 hrs, 5 hrs, 6 hrs, 7 hrs and 8 hrs reaction time, samples (1 ml volume) for monitoring the reaction are withdrawn from the reaction suspension with a pipette and analyzed by HPLC (see IPC method above):

For this, 1 ml sample volume is diluted with 9 ml of a solvent mix of methanol/H$_2$O (9:1; v/v) in a 20 ml snap-lid vial and mixed well. The snap-lid vial is sealed. Before injection onto the HPLC column, the turbid, diluted solution must be centrifuged. The clear supernatant is then taken off, and the injection volume withdrawn therefrom.

The reaction is ended after a suitable time, for example 7 to 10 hrs, such as for example after 8 hrs reaction time. For this, the turbid reaction solution is acidified (pH≤1.5) with ca. 4-5 ml conc. HCl and stirred for a further 30 mins.

8.7 Evaluation

Determination of the Reaction Kinetics:

The reaction monitoring/reaction kinetics is made up of the (not analyzed) start point "0 hrs" (for DHCA: 100% area, for all other analytes: 0% area) and for example 11 further measurement points/HPLC analyses (e.g. after 0.5 hrs, 1 hr, 1.5 hrs, 2 hrs, 2.5 hrs, 3 hrs, 4 hrs, 5 hrs, 6 hrs, 7 hrs and 8 hrs reaction time).

The composition of the analytes in the current sampling (at time point: x hrs reaction time) is to be determined. For this the % area data in the HPLC-UV chromatogram for the analytes DHCA (educt), 12-keto-UDCA (end product), 3,12-diketo-ursodeoxycholic acid (3,12-diketo-UDCA; intermediate) and 7,12-diketo-cholic acid (7,12-diketo-CA; intermediate) are evaluated and reported.

B. Whole Cell Reduction

Example B.1

Two-Stage Whole Cell Reduction of DHCA with Three Different Whole Cell Biocatalysts (X=67)

Figure 2:
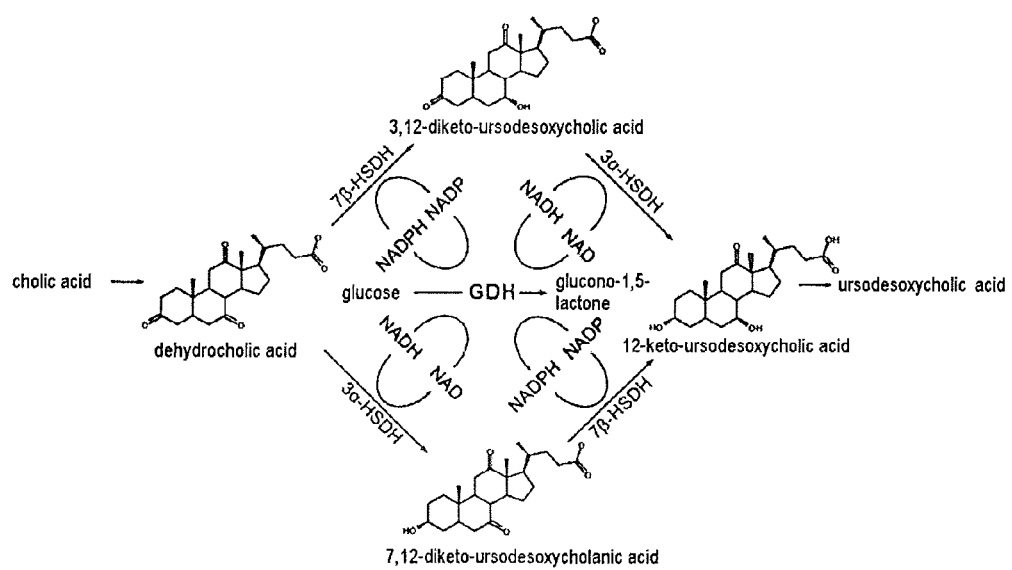
Figure 3:
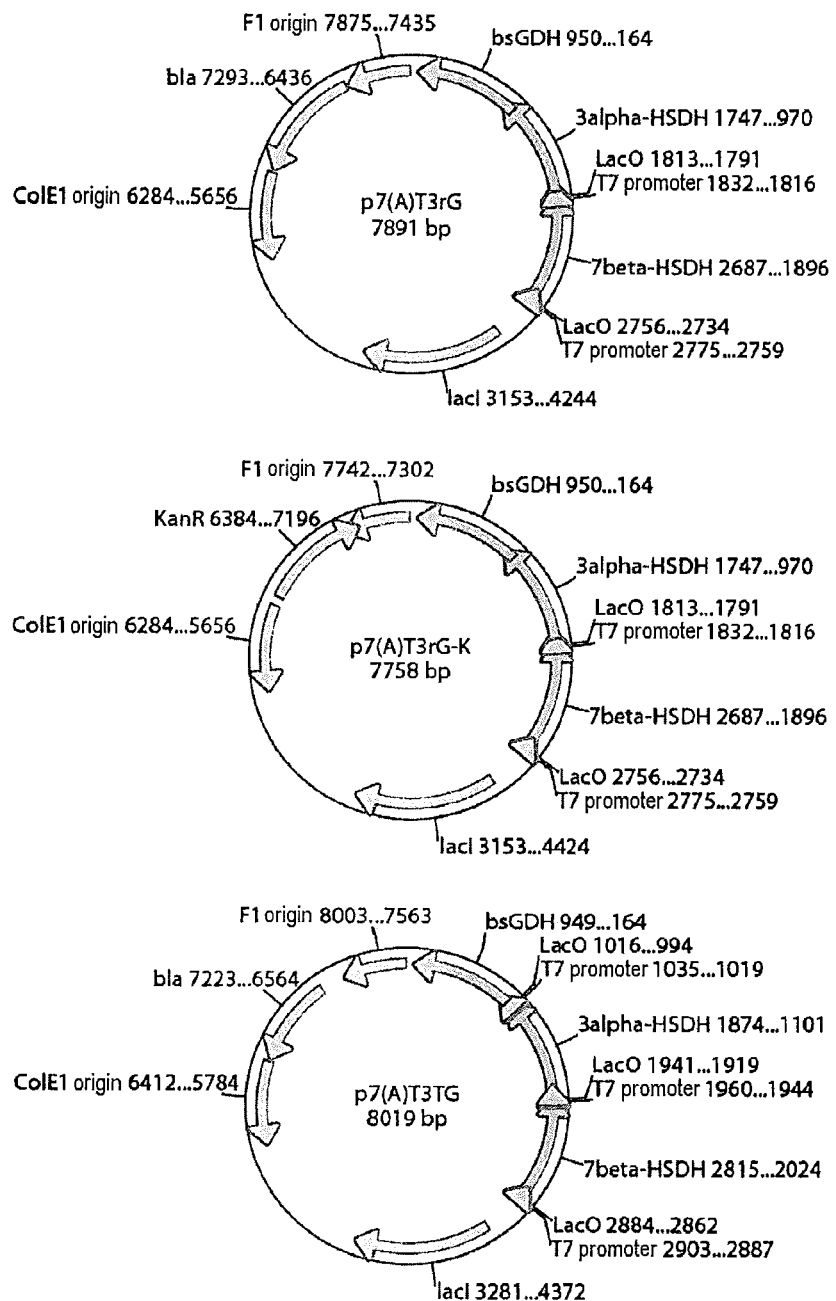
FIG. 3 shows the vector maps of the expression plasmids p7(A)T3rG (SEQ ID No. 18), p7(A)T3rG-K (SEQ ID No. 19) and p7(A)T3TG (SEQ ID No. 20).

For the conversions, the biocatalyst strains *E. coli* BL49 p7(A)T3rG, *E. coli* BL21 ΔhdhA p7(A)T3rG-K and *E. coli* BL49 p7(A)T3TG were used. The plasmids p7(A)T3rG, p7(A)T3rG-K and p7(A)T3TG each have expression cassettes in which the genes 7β-HSDH, 3α-HSDH and GDH are encoded, but with different expression cassette structure and with different antibiotic resistances. These plasmids were transformed as desired into the host strain *E. coli* BL49 or *E. coli* BL21 ΔhdhA (both known from WO 2012/080504 and the applicant's WO 2011/147957), these being different knockout strains, in each of which the genomic 7α-HSDH had been knocked out. The expression plasmids are shown in FIG. 3.

With the said biocatalysts, conversions were performed on the 1 L scale. In this, in each case 1 $g_{BDM} L^{-1}$ biocatalyst, 0.05 mM NAD and 0.01 mM NADP were used, thus for all three preparations X=67. Further conversion conditions were: 70 mM DHCA, 350 mM glucose, 10 mM MgCl$_2$, 50 mM potassium phosphate buffer, pH 7 and 30° C. Essential for the assessment of the conversion is the quantity of the product formed (12-keto-UDCA) in the reaction mixture. The concentrations of the substrate DHCA, the intermediate 3,12-diketo-UDCA and 7,12-diketo-UDCA and of the product 12-keto-UDCA in the reaction mixture can be determined by high performance liquid chromatography (HPLC).

Figure 4:
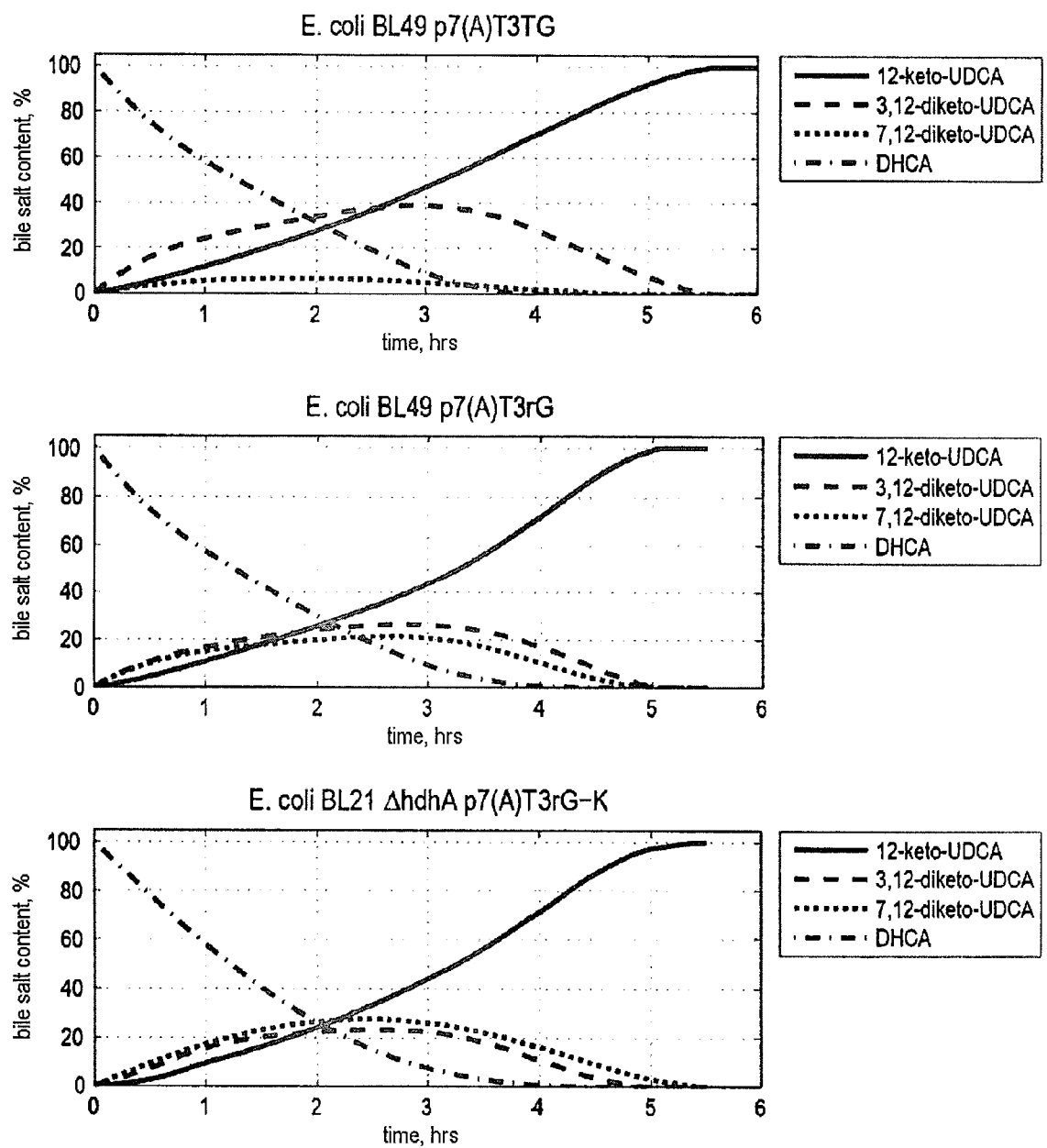
FIG. 4 shows the course of the biocatalysis reactions with the whole cell biocatalysts *E. coli* BL49 p7(A)T3rG, *E. coli* BL21 ΔhdhA p7(A)T3rG-K and *E. coli* BL49 p7(A)T3TG with use of 1 $g_{BDM}$ L$^{-1}$ biocatalyst, 0.05 mM NAD and 0.01 mM NADP (X=67).

The courses of the reactions are shown in FIG. 4. With all the preparations, after 5-6 hrs a conversion of >99% could be achieved. Thus it is clear that the formula is valid for various whole cell biocatalyst strains, as long as all three enzymes 7β-HSDH, 3α-HSDH and GDH are expressed.

Example B.2

Two-Stage Whole Cell Reduction of DHCA with 3.5 $g_{BDM} L^{-1}$ Biocatalyst and 0.025 mM NAD (X=147.5)

For the conversion, the biocatalyst strain *E. coli* BL49 p7(A)T3rG was used. In this, 3.5 $g_{BDM} L^{-1}$ biocatalyst, 0.025 mM NAD and no NADP were used, thus for this preparation X=147.5. Further conversion conditions were: 70 mM DHCA, 350 mM glucose, 10 mM MgCl$_2$, 50 mM potassium phosphate buffer, pH 7, 30° C. and 20 mL reaction volume.

Figure 5:
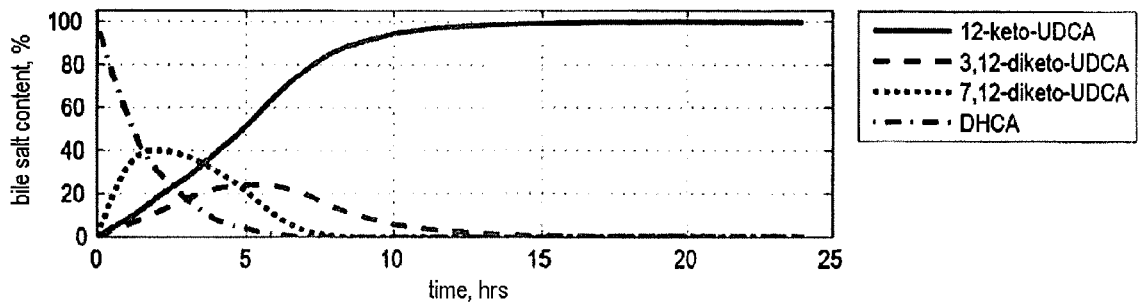
FIG. 5 shows the course of the biocatalysis reaction with the whole cell biocatalyst *E. coli* BL49 p7(A)T3rG with use of 3.5 $g_{BDM}$ L$^{-1}$ biocatalyst and 0.025 mM NAD (X=147.5).

The course of the reaction is shown in FIG. 5. With this preparation, after 24 hrs a conversion of >99% can be achieved. Thus the formula is valid for this approach. Furthermore, it is shown that NAD and NADP do not absolutely necessarily have to be added, but also the addition of one of the substances can be sufficient.

Example B.3

Two-Stage Whole Cell Reduction of DHCA with 1.75 $g_{BDM}$ $L^{-1}$ Biocatalyst, 0.025 mM NAD and 0.01 mM NADP (X=89.5)

For the conversion, the biocatalyst strain E. coli BL49 p7(A)T3rG was used. In this, 1.75 $g_{BDM}$ $L^{-1}$ biocatalyst, 0.025 mM NAD and 0.01 mM NADP were used, thus for this approach X=89.5. Further conversion conditions were: 70 mM DHCA, 350 mM glucose, 10 mM $MgCl_2$, 50 mM potassium phosphate buffer, pH 7, 30° C. and 20 mL reaction volume.

Figure 6:
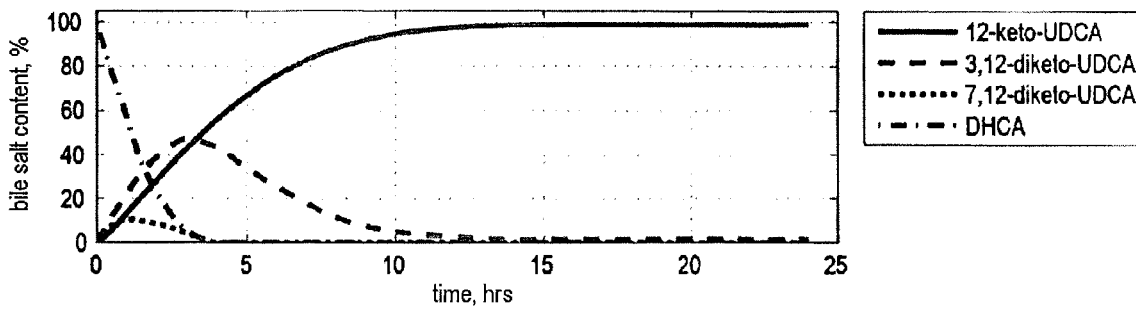
FIG. 6 shows the course of the biocatalysis reaction with the whole cell biocatalyst *E. coli* BL49 p7(A)T3rG with use of 1.75 $g_{BDM}$ L$^{-1}$ biocatalyst, 0.025 mM NAD and 0.01 mM NADP (X=89.5).

The course of the reaction is shown in FIG. 6. With this approach, after 24 hrs a conversion of >98% can be achieved. Thus the formula is valid for this approach.

Example B.4

Two-Stage Whole Cell Reduction of DHCA with 1 $g_{BDM}$ $L^{-1}$ Biocatalyst, 0.04 mM NAD and 0.0075 mM NADP (X=61)

For the conversion, the biocatalyst strain E. coli BL21 ΔhdhA p7(A)T3rG-K was used. In this, 1 $g_{BDM}$ $L^{-1}$ biocatalyst, 0.04 mM NAD and 0.0075 mM NADP were used, thus for this approach X=61. Further conversion conditions were: 70 mM DHCA, 200 mM glucose, 5 mM $MgCl_2$, 4% (v/v) glycerin, 50 mM potassium phosphate buffer, pH 7, 30° C. and 20 mL reaction volume.

Figure 7:
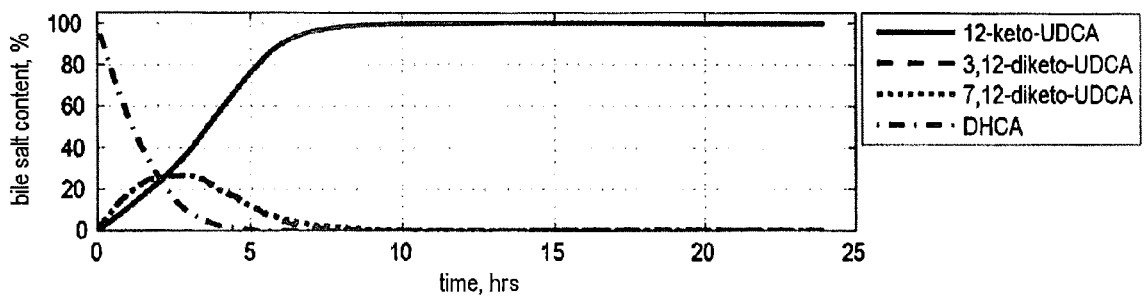
FIG. 7 shows the course of the biocatalysis reaction with the whole cell biocatalyst *E. coli* BL21 ΔhdhA p7(A) T3rG-K with use of 1 $g_{BDM}$ L$^{-1}$ biocatalyst, 0.04 mM NAD and 0.0075 mM NADP (X=61).

The course of the reaction is shown in FIG. 7. With this approach, after 24 hrs a conversion of >99% can be achieved. Thus the formula is valid for this approach.

Example B.5

Two-Stage Whole Cell Reduction of DHCA with the Whole Cell Biocatalyst E. coli BLLiu p7(A)T3TG-K

A kanamycin-resistant whole cell biocatalyst strain with increased GDH expression was produced. In this, the plasmid p7(A)T3rG-K has been modified to the extent that an additional T7 promoter has been inserted into the expression cassette before the GDH. The resulting plasmid bears the name p7(A)T3TG-K and was transformed into the host strain E. coli BLLiu. The resulting whole cell biocatalyst bears the name E. coli BLLiu p7(A)T3TG-K.

a) Culturing of the Whole Cell Biocatalyst E. coli BLLiu p7(A)T3TG-K

The strain E. coli BLLiu p7(A)T3TG-K was cultured in the stirred vessel reactor according to the standard protocol and compared with related strains as regards growth and expression behavior.

For this, the strain E. coli BLLiu p7(A)T3TG-K was cultured according to the standard protocol in the stirred vessel reactor at an expression temperature of 25° C. The cell concentrations and enzyme activities present at the time of harvesting are stated in the following Table 3. Contrasted with this are the data for the original kanamycin-resistant strain E. coli BLLiu p7(A)T3rG-K and the data for the ampicillin-resistant strain BL49 p7(A)T3TG also with increased GDH activity From the table, it can be seen that the novel strain E. coli BLLiu p7(A)T3TG-K has markedly higher 7β-HSDH activities than the respectively comparison strains (factor of 2.4-2.7). The 3α-HSDH activity is at the level of the highest value among the comparison strains. On the other hand, the GDH activity is higher by the factor of 4-10 than that of the kanamycin-resistant strain E. coli BLLiu p7(A)T3rG-K, but is only 70% of the GDH activity of the ampicillin-resistant strain BL49 p7(A)T3TG. The cell concentration attained at the time of harvesting was consistently higher than with the comparison strains.

TABLE 3

Comparison of the growth and expression data of the strain E. coli BLLiu p7(A)T3TG-K with the strains E. coli BLLiu p7(A)T3rG-K and E. coli BL49 p7(A)T3TG

| Strain | BLLiu p7(A)T3rG-K | | BL49 p7(A)T3TG | BLLiu p7(A)T3TG-K |
|---|---|---|---|---|
| $T_{Expression}$,° C. | 20 | 25 | 30 | 20 | 25 |
| OD, — | 69 | 64 | 66 | 62 | 78 |
| BDM, g $L^{-1}$ | 33 | 34 | 37 | 37 | 40 |
| 7β-HSDH, U $g_{BDM}^{-1}$ | 565 | 509 | 556 | 490 | 1360 |
| 3α-HSDH, U $g_{BDM}^{-1}$ | 111 | 135 | 74 | 70 | 135 |
| GDH, U $g_{BDM}^{-1}$ | 343 | 184 | 127 | 1900 | 1300 | b) Biotransformation of the Whole Cell Biocatalyst E. coli BLLiu p7(A)T3TG-K

The new strain E. coli BLLiu p7(A)T3TG-K cultured in the stirred vessel bioreactor was investigated as regards the whole cell biocatalysis performance.

For the evaluation of the whole cell biocatalysis performance, both cells stored at −20° C. and also those stored at room temperature and 4° C. were used. In contrast to previous strains, with this strain a storage duration of 1 day at room temperature was not sufficient to obtain the full activity of the cells. Because of this, after 1 day storage at room temperature and 3 days storage at 4° C., the strain was again stored for 3 days at room temperature and then used for the biotransformation.

The reaction conditions for the whole cell biotransformations were: 70 mM DHCA, 350 mM glucose, OD 2 cells, 50 μM NAD, 10 μM NADP, 1 mM $MgCl_2$, 50 mM KPi buffer (pH 7.0) and 30° C. Additionally, with the cells stored at room temperature cells, an experiment was performed with the doubled NAD concentration of 100 μM. The pH was manually adjusted half-hourly to the starting value with NaOH solution (5 M). The courses of the biotransformations are shown in FIG. 11.

On comparison of the biotransformations with standard NAD concentrations (50 μM), the reactions were complete after 4 hrs (with cells stored at −20° C.) and 4.5 hrs (with cells stored at RT/4° C.). The duration of the biotransformations thus lies in the range or slightly below the times which were achieved with other biocatalyst strains (4.5 hrs-6 hrs). However, the uneven by-product formation is discernible. In both preparations, the intermediate product of the 7β-HSDH (3,12-diketo-UDCA) accumulates more strongly than the intermediate product of the 3α-HSDH. This is attributable to the markedly increased 7β-HSDH activity of this strain in comparison to other whole cell biocatalyst strains. If the NAD concentration—and thus the cofactor concentration for the 3α-HSDH conversion—is increased, then this results in an equalization of the reaction rates of the two HSDH, which is to be discerned in equal formation of the two intermediate products. Further, the duration of the biotransformation decreases from 4.5 hrs to 4.0 hrs.

C. 7β-HSDH Mutants

Example C.1

Production of 7β-HSDH Mutants with NADH Specificity

Herein, enzyme mutants of the 7β-HSDH from *Collinsella aerofaciens*, which were produced by protein engineering, and which accept NADH instead of NADPH as cofactor are described.

The 7β-HSDH mutants according to the invention differ from the published sequence of the native enzyme in their amino acid sequence at the positions 39, 40, 41 and/or 44, and from the known 7β-HSDH mutants at the positions 40, 41 and 44.

The mutant 7β-HSDH DF contains the amino acid substitutions G39D R40F compared to the wild type sequence, the mutant 7β-HSDH DFK contains the amino acid substitutions G39D R40F R41K compared to the wild type sequence and the mutant 7β-HSDH DFKG contains the amino acid substitutions G39D R40F R41K K44G compared to the wild type sequence (see FIG. 8)).

C.1.2 Production of the NADH-Dependent Single Mutant G39D

The G39D mutant of the 7β-HSDH was produced as described in WO 2012/080504. The protein was expressed with an N-terminal His tag and purified by IMAC. A first activity assay showed only very slight NADPH activity (0.040±0.005 U mg$^{-1}$ with 10 mM DHCA, 0.5 mM NADPH and pH 8.0). On the other hand, marked NADH activity could be observed.

C.1.3 Directed Evolution of the NADH-Dependent 7β-HSDH a) Production of the Host Strain for the Mutant Library The further mutagenesis is to be effected according to the principle of iterative saturation mutagenesis (Reetz et al., *Mol. Biosyst.*, 5(2):115-22, 2009). For this, for the production of a mutant library an *E. coli* host strain is needed which has a high transformation efficiency and is at the same time well suited for screening with cell lysate. Since *E. coli* has a genomically encoded 7β-HSDH which catalyzes a side-reaction in the screening and thus can falsify measurement data, recourse must be had to a host strain in which this gene is silenced. However, the two existing knockout strains BL49 and BLLiu are both *E. coli*-BL21(DE3) derivatives which have a low transformation efficiency. Thus it was necessary firstly to produce a suitable host strain in which the genomic 7α-HSDH is silenced.

As the starting strain for the knockout, *E. coli* NovaBlue (DE3) was selected, a K-12 derivative with high transformation efficiency. At the same time, the DE3 cassette enables expression of foreign protein with the T7 expression system, through which this differs from *E. coli* DH5α. The successful silencing of the gene for the 7α-HSDH and the subsequent secretion of the knockout plasmid were confirmed by culturing on appropriate selection antibiotics, PCR and sequencing. This strain bears the name *E. coli* NB13.

b) Selection of the Positions to be Mutated

The conserved regions in NADPH-binding SDR (short chain dehydrogenase reductase) mainly include basic amino acid residues in the cofactor-binding pocket, which stabilize the NADP(H) binding by acid-base interaction with the 2'-phosphate group on the adenosine ribose of the NADP(H) (Carugo, O. & Argos, P., *Proteins*, 28(1):10-28, 1997a+ *Proteins*, 28(1): 29-40, 1997b; Woodyer et al., *Biochemistry*, 42(40):11604-14, 2003). Above all, the position 40 adjacent to position 39 is to be considered, at which as a rule an arginine or a lysine is situated in NADPH-binding SDR (Bellamacina, C. R., *FASEB J.*, 10(11):1257-69, 1996; Kallberg et al., *Eur. J. Biochem.*, 269(18):4409-4417, 2002; Persson, B., *Chem. Biol. Interact.*, 143-144:271-278, 2003).

In the 7β-HSDH, with R40 a basic amino acid is also present at the position adjacent to the G39. Additionally, with R41 and K44 two further basic amino acids were identified in direct proximity to the binding pocket. These three positions were defined as target positions for the iterative saturation mutagenesis.

c) Implementation of the Directed Evolution

Primers Used:

7β-HSDH G39D R40F (DF).

7beta mut G39D R40F fwd:

```
                                         (SEQ ID No. 14)
CGTCGTCATGGTCGACTTTCGCGAGG

AntiMid rev:
                                         (SEQ ID No. 15)
CCGCCGCATCCATACCGCCAGTTGTTTACCC
```

7β-HSDH G39D R40F R41K (DFK)

7beta DF mut R41K fwd:

```
                                         (SEQ ID No. 16)
CGTCGTCATGGTCGACTTTAAAGAGGAGAAGCTG

AntiMid rev:
                                         (SEQ ID No. 15)
CCGCCGCATCCATACCGCCAGTTGTTTACCC
```

7β-HSDH G39D R40F R41K K44G (DFKG)

7beta DFK mut K44NDT fwd:

```
                                         (SEQ ID No. 17)
GTCGACTTTAAAGAGGAGNDTCTGAACGTGCTC
```

This primer contains a degenerate codon, so that other amino acids than G can also occur at position 44.

AntiMid Rev:

```
                                         (SEQ ID No. 15)
CCGCCGCATCCATACCGCCAGTTGTTTACCC
```

The directed evolution was performed in three rounds of mutagenesis, in each of which one position was mutated. The mutant of each round which showed the highest NADH activity in the screening was sequenced to identify the mutation, and served as the starting mutant in the next round. The mutagenesis was effected starting from 7β-HSDH G39D (D) firstly at position R40. The best mutant in this was 7β-HSDH G39D R40F (DF). Next, the mutagenesis at the position R41 was effected, with 7β-HSDH G39D R40F R41K (DFK) as best mutant and finally at the position K44, with 7β-HSDH G39D R40F R41K K44G (DFKG) as best mutant.

Example C.2

Enzyme Kinetic Study of the 7β-HSDH Mutants with NADH Specificity

The mutants created were assessed by means of enzyme kinetic studies. For the study of the DHCA kinetics, 0.5 mM NADH was used as the cofactor (FIG. 9), while for the study of the NADH kinetics, 10 mM DHCA was used as the substrate (FIG. 10). From the plots of the DHCA kinetics, the characteristic curve shapes of the Michaelis-Menten kinetics can be discerned for the 7β-HSDH mutants, and no substrate inhibition was observed. Accordingly, the classical Michaelis-Menten model (equation 1) was used for the evaluation of the kinetic parameters. On the other hand, the NADH kinetics showed a linear course and indicate no saturation in the cofactor concentration, hence no kinetic parameters could be determined for this.

Equation 1: Michaelis-Menten Equation.

$$EA_X = v_{max} \cdot \frac{c_s}{K_m + c_s}$$

$EA_X$: specific enzyme activity, U mg$^{-1}$=μmol min$^{-1}$ mg$^{-1}$
$v_{max}$: maximal specific enzyme activity, U mg$^{-1}$=μmol min$^{-1}$ mg$^{-1}$
$c_s$: substrate or cofactor concentration, mol L$^{-1}$
$K_m$: half-saturation concentration, mol L$^{-1}$ The kinetic parameters determined for the new 7β-HSDH mutants are shown in Table 4, and the table additionally contains comparison values for the previously reported mutants G39D and G39D R40I. It can be seen therein that the novel mutants 7β-HSDH DFK and 7β-HSDH DFKG with 5.91±0.23 U mg$^{-1}$ and 5.72±0.19 U mg$^{-1}$ respectively show a maximum specific enzyme activity higher by 23-27% than the previously most active mutant G39D R40I.

TABLE 4

Enzyme kinetic parameters of the new 7β-HSDH mutants DF, DFK and DFKG with NADH as cofactor. As a reference, the previously produced mutants G39D and G39D R40I are shown.

|  | $K_{m, DHCA}$, μM | $v_{max}$, U mg$^{-1}$ |
|---|---|---|
| G39D | 660 ± 120 | 2.90 ± 0.16 |
| G39D R40I | 920 ± 170 | 4.64 ± 0.27 |
| DF | 420 ± 60 | 3.70 ± 0.13 |
| DFK | 290 ± 50 | 5.91 ± 0.23 |
| DFKG | 380 ± 50 | 5.72 ± 0.19 |

Example C.3

Single-Stage Biotransformation with NADH-Dependent 7β-HSDH Mutants

For comparison of the NADH-dependent 7β-HSDHs, single-stage biotransformations of 50 mM DHCA to 3,12-diketo-UDCA on the 2 mL scale were performed in triplicate.

Here, purified enzymes were used, and only NAD added as cofactor. For the cofactor regeneration, a GDH was used. Of the 7β-HSDH studied (wild type (WT) and mutants: D, DF, DFK and DKFG), in each case 0.2 mg mL$^{-1}$ of enzyme were used. The other reaction conditions were: 10 U mL$^{-1}$ GDH, 0.5 mM NAD, 50 mM DHCA, 200 mM glucose, 500 mM potassium phosphate and pH 8.0. The reactions were performed in triplicate in shaken deep well plates at 30° C. as batch processes with no pH control in the strongly buffered system.

The results of the biotransformation are shown in FIG. 12. With all NADH-dependent mutants, more 3,12-diketo-UDCA could be formed than with the wild type enzyme.

With the mutant DFKG, after 16 hrs a complete conversion of DHCA to 3,12-diketo-UDCA could be achieved.

Example C.4

Two-Stage Biotransformation with NADH-Dependent 7β-HSDH Mutants

Furthermore, with the NADH-dependent 7β-HSDH mutants DFK and DFKG, two-stage biotransformations of 50 mM DHCA to 12-keto-UDCA on the 2 mL scale were performed in triplicate.

In this, purified enzymes were used and only NAD added as cofactor. As well as the 7β-HSDH, a 3α-HSDH from *Comomonas testosteroni* and a GDH for cofactor regeneration were used. Of the 7β-HSDH mutants studied, 0.2 mg mL$^{-1}$ enzyme were used in each case. The other reaction conditions were: 1 U mL$^{-1}$ 3α-HSDH, 10 U mL$^{-1}$ GDH, 0.5 mM NAD, 50 mM DHCA, 200 mM glucose, 500 mM potassium phosphate and pH 8.0. The reactions were performed in triplicate in shaken deep well plates at 30° C. as batch processes with no pH control in the strongly buffered system.

The reaction curves of the respective preparations are shown in FIG. 13. With both 7β-HSDH mutants complete conversions of DHCA to 12-keto-UDCA could be achieved without addition of NADP.

TABLE 5

Assignment of SEQ ID Nos:

| SEQ ID No. | Description | Type |
|---|---|---|
| 1 | 7β-HSDH (*C. aerofaciens*) | NS |
| 2 | 7β-HSDH (*C. aerofaciens*) | AS |
| 3 | 3α-HSDH (*C. testosteroni*) | NS |
| 4 | 3α-HSDH (*C. testosteroni*) | AS |
| 5 | 7α-HSDH | NS |
| 6 | 7α-HSDH | AS |
| 7 | GDH, (*B. subtilis*) | NS |
| 8 | GDH (*B. subtilis*) | AS |
| 9 | 7β-HSDH G39D | AS |
| 10 | 7β-HSDH G39D R40I | AS |
| 11 | 7β-HSDH G39D R40F | AS |
| 12 | 7β-HSDH G39D R40F R41K | AS |
| 13 | 7β-HSDH G39D R40F R41K K44G | AS |
| 14 | PCR primer | NS |
| 15 | PCR primer | NS |
| 16 | PCR primer | NS |
| 17 | PCR primer | NS |
| 18 | Plasmid p7(A)T3rG-A | NS |
| 19 | Plasmid p7(A)T3rG-K | NS |
| 20 | Plasmid p7(A)T3TG-A | NS |
| 21 | Plasmid p7(A)T3TG-K | NS |

AS = amino acid sequence
NS = nucleic acid sequence

Reference is expressly made to the disclosure of the publications mentioned herein.

The invention claimed is:

1. A 7β-hydroxysteroid dehydrogenase (7β-HSDH) that catalyzes at least the stereospecific enzymatic reduction of a 7-ketosteroid to the corresponding 7-hydroxysteroid, wherein the enzyme has an amino acid sequence having at least 90% sequence identity to SEQ ID NO: 2 and comprises:
   a) the double mutation G39D/R40F, wherein the amino acid numbering of said mutation corresponds to positions 39 and 40 of SEQ ID NO: 2:
   b) the triple mutation G39D/R40F/R41$X_1$, wherein $X_1$ represents any other amino acid residue: or
   c) the quadruple mutation G39D/R40F/R41$X_1$/K44$X_2$, wherein $X_1$ represents any other amino acid residue, wherein the amino acid numbering of said triple and quadruple mutations corresponds to positions 39, 40, 41 and 44 respectively of SEQ D NO: 2.

2. The 7β-HSDH of claim 1, comprising the double mutation G39D/R40F.

3. The 7β-HSDH of claim 1, comprising the triple mutation G39D/R40F/R41K.

4. The 7β-HSDH of claim 1, comprising the quadruple mutation G39D/R40F/R41K/K44G.

5. A nucleic acid molecule comprising a nucleotide sequence that encodes a 7β-HSDH of claim 1.

6. An expression cassette comprising at least one nucleotide sequence encoding the 7β-HSDH of claim 1, wherein the expression of said nucleotide sequence is under the control of at least one regulatory sequence.

7. An expression vector comprising at least one expression cassette of claim 6.

8. A recombinant microorganism comprising at least one nucleic acid molecule of claim 5.

9. The recombinant microorganism of claim 8 further comprising a nucleic acid molecule comprising a nucleotide sequence encoding an additional enzyme selected from the group consisting of hydroxysteroid dehydrogenases (HSDH) and cofactor regenerating dehydrogenases.

10. The recombinant microorganism of claim 9, wherein:
   the additional HSDH is selected from the group consisting of 3α-HSDHs; and
   the additional cofactor regenerating dehydrogenase is selected from the group consisting of NADH-regenerating enzymes.

11. The recombinant microorganism of claim 8 which is a 7α-HSDH knock-out strain.

12. A method for producing an ursodesoxycholic acid (UDCA) of formula (1)

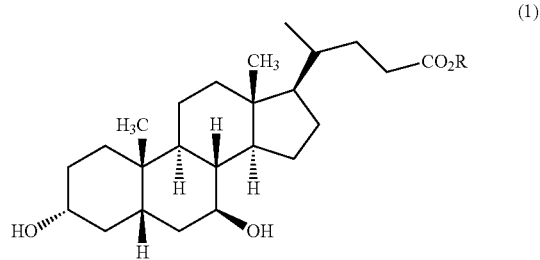

(1)

wherein

R represents alkyl, H, an alkali metal ion or $N(R^3)_4{}^+$, wherein each of the $R^3$ residues is the same or different and represents H or alkyl, or the group —$CO_2R$ is replaced by the acid amide group —$CONR^1R^2$, wherein $R^1$ and $R^2$ independently of one another represent an alkyl residue;

wherein the method comprises:

a) reducing dehydrocholic acid (DHCA) of formula (2)

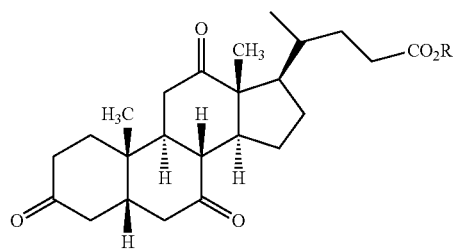

(2)

to the corresponding 12-keto-ursodesoxycholic acid (12-keto UDCA) of formula (3)

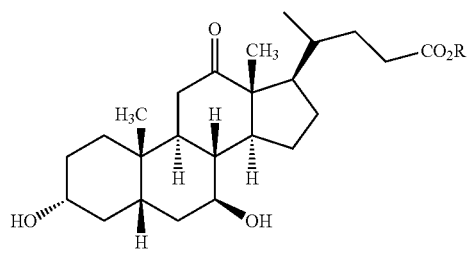

(3)

in the presence of:
  at least one 7β-HSDH of claim 1; and
  at least one 3α-HSDH;

wherein in formulas (2) and (3), R has the meanings stated above, or the group —$CO_2R$ is replaced by the acid amide group —$CONR^1R^2$, as defined above; and b) chemically reducing the 12-keto-UDCA of formula (3) to UDCA; thereby producing an ursodesoxycholic acid (UDCA) of formula (1).

13. The method of claim 12, wherein the reduction of step a) takes place in the presence of a recombinant microorganism having a nucleic acid molecule comprising a nucleotide sequence encoding the 7β-HSDH.

14. The method of claim 12, further comprising, prior to step a), chemically oxidizing a cholic acid (CA) of formula (4)

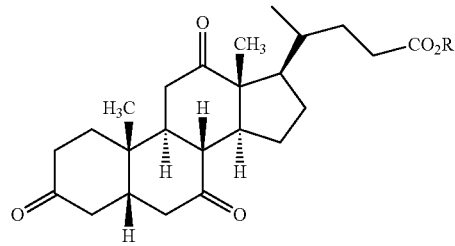

(4)

to a dehydrocholic acid (DHCA) of formula (2)

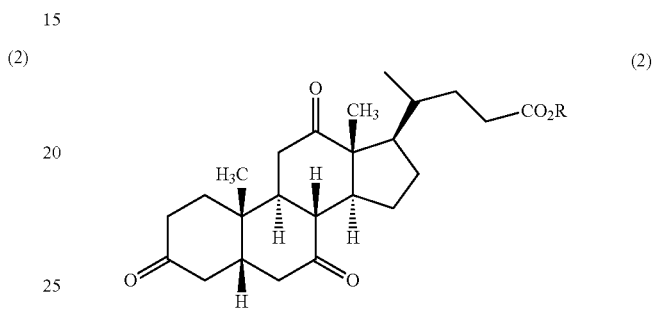

(2)

wherein in formulas (2) and (4), R has the meanings as defined in claim 12, or the group —$CO_2R$ is replaced by the acid amide group —$CONR^1R^2$ as defined in claim 12.

15. The method of claim 12, wherein step a) is carried out in the presence of and with consumption of NADH and/or NADPH.

16. The method of claim 12, further comprising purifying the ursodesoxycholic acid (UDCA) obtained in step b).

17. The 7β-HSDH of claim 1, wherein the enzyme comprises a triple mutation G39D/R40F/R41$X_1$, wherein $X_1$ represents K, Q, S or R.

18. The 7β-HSDH of claim 1, wherein the enzyme comprises
  a quadruple mutation G39D/R40F/R41$X_1$/K44$X_2$, wherein $X_1$ represents K, Q, S or R and $X_2$ represents G, N or Q.

19. The 7β-HSDH of claim 1, wherein the enzyme comprises an amino acid sequence having at least 95% sequence identity to SEQ ID NO: 2.

20. The recombinant organism of claim 8 comprising at least one expression cassette comprising at least one nucleotide sequence encoding a 7β-hydroxysteroid dehydrogenase (7β-HSDH) that catalyzes at least the stereospecific enzymatic reduction of a 7-ketosteroid to the corresponding 7-hydroxysteroid, wherein the enzyme has an amino acid sequence having at least 90% sequence identity to SEQ D NO: 2 and comprises:
  a) the double mutation G39D/R40F. wherein the amino acid numbering of said mutation corresponds to positions 39 and 40 of SEQ ID NO: 2:
  b) the triple mutation G39D/R40F/R41$X_1$, wherein $X_1$ represents any other amino acid residue; or
  c) the quadruple mutation G39D/R40F/R41$X_1$/K44$X_2$, wherein $X_1$ represents any other amino acid residue:
wherein the amino acid numbering of said triple and quadruple mutations corresponds to positions 39, 40, 41 and 44, respectively, of SEQ ID NO: 2, and wherein the expression of said nucleotide sequence is under the control of at least one regulatory sequence.

21. The recombinant organism of claim 8 comprising at least one expression vector comprising at least one expression cassette comprising at least one nucleotide sequence encoding a 7β-hydroxysteroid dehydrogenase (7β-HSDH) that catalyzes at least the stereospecific enzymatic reduction of a 7-ketosteroid to the corresponding 7-hydroxysteroid, wherein the enzyme has an amino acid sequence having at least 90% sequence identity to SEQ ID NO: 2 and comprises:
a) the double mutation G39D/R40F, wherein the amino acid numbering of said mutation corresponds to positions 39 and 40 of SEQ ID NO: 2;
b) the quadruple mutation G39D/R40F/R41$X_1$, wherein $X_1$ represents any other amino acid residue; or
c) the quadruple mutation G39D/R40F/R41$X_1$/K44$X_2$, wherein $X_1$, represents any other amino acid residue:
wherein the amino acid numbering of said triple and quadruple mutations corresponds to positions 39, 40, 41 and 44 respectively, of SEQ ID NO: 2, and wherein the expression of said nucleotide sequence is under the control of at least one regulatory sequence.

22. The recombinant organism of claim 10, wherein the NADH regenerating enzymes are selected from the group consisting of NADH dehydrogenases NADH-regenerating alcohol dehydrogenases (ADH), NADH-regenerating formate dehydrogenases (FDH), NADH-regenerating glucose-6-phosphate dehydrogenase (G-6-PDH), NADH-regenerating phosphite dehydrogenases (PtDH) and NADH-regenerating glucose dehydrogenases (GDH).

23. A method for biocatalytic reduction of a dehydrocholic acid (DHCA) of formula (2)

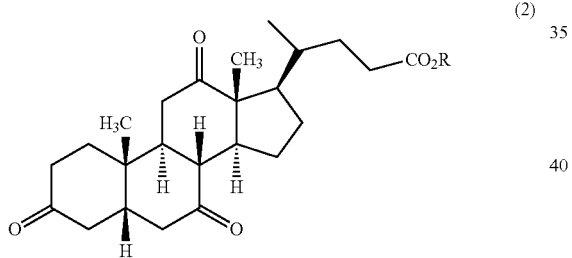

(2)

to a corresponding 12-keto-ursodesoxycholic acid (12-keto UDCA) of formula (3)

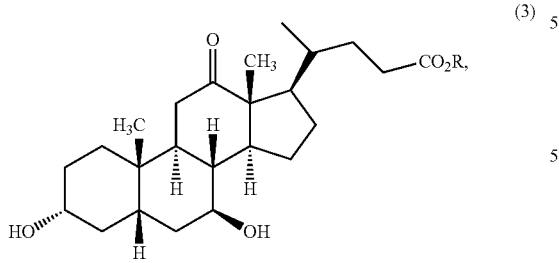

(3)

wherein:
in formulas (2) and (3), R represents alkyl, H, an alkali metal ion or $N(R^3)_4^+$, wherein each of the $R^3$ residues is the same or different and represents H or alkyl, or the group —$CO_2R$ is replaced by the acid amide group —$CONR^1R^2$, wherein $R^1$ and $R^2$ independently of one another represent an alkyl residue;

the method comprising bringing into contact one or more compounds of formula (2) with one or more whole cell biocatalysts expressing the enzyme activity of a 7β-hydroxysteroid dehydrogenase (7β-HSDH) of claim 1 and the enzyme activity of a3α-hydroxysteroid dehydrogenase (3α-HSDH) in a liquid reaction medium comprising NAD(H) and/or NADP(H) and glucose, wherein:
the one whole cell biocatalyst expresses or the more than one whole cell biocatalysts together simultaneously express the enzyme activities of the 7β-hydroxysteroid dehydrogenase (7β-HSDH) according to claim 1 and the enzyme activity of the3α-hydroxysteroid dehydrogenase (3α-HSDH); and
wherein:
the concentration of the one or more whole cell biocatalysts, the NAD(H) and/or NADP(H), and the compound of formula (2) in the reaction mixture are in the following mathematical relationship:

$X < Y \cdot 200$ with $Y = c_{DHCA}/70$ and $X = C_{Cat} \cdot 40 + c_{NAD(H)} \cdot 300 + c_{NADP(H)} \cdot 1200;$ wherein the parameters are defined as follows:
cDHCA =initial substrate concentration [mM] of a compound of formula (3);
$C_{Cat}$=whole cell biocatalyst concentration [gBDM $L^{-1}$];
$c_{NAD(H)}$=NAD(H) concentration [mM]; and
$c_{NADP(H)}$=NADP(H) concentration [mM]; and
wherein the one or more whole cell catalysts are selected from the group consisting of bacteria, fungi and yeasts;
thereby biocatalytically reducing a dehydrocholic acid compound (DHCA) of formula (2) to a corresponding 12-keto-ursodesoxycholic acid compound (12-keto UDCA) of formula (3).

24. The method of claim 23, further comprising adding GDH to the liquid reaction medium.

25. The method of claim 23, wherein, if GDH is not added to the liquid reaction medium, the one or more whole cell biocatalysts express the enzyme activity of GDH.

26. The method of claim 23, wherein the whole cell biocatalyst is a recombinant microorganism.

27. The method of claim 23, wherein the 3α-HSDH has an amino acid sequence according to SEQ ID NO: 4 or an amino acid sequence derived therefrom with at least 90% sequence identity to SEQ ID NO: 4.

28. The method of claim 24, wherein the GDH has an amino acid sequence according to SEQ ID NO: 6 or an amino acid sequence derived therefrom with at least 90% sequence identity to SEQ ID NO: 6.

29. The method of claim 23, wherein the biocatalyst is a recombinant strain of microorganisms of the genus Escherichia.

30. The method of claim 23, wherein the biocatalyst is a recombinant strain of E. coli.

31. The method as claimed claim 23, wherein the 7β-HSDH and the 3α-HSDH use the same or different cofactors selected from the group consisting of NAD(H) and NADP(H).

32. The method of claim 24, wherein the 7β-HSDH, 3α-HSDH and GDH use the same or different cofactors selected from the group consisting of NAD(H) and NADP(H).

33. The method of claim 25, wherein the 7β-HSDH, 3α-HSDH and GDH use the same or different cofactors selected from the group consisting of NAD(H) and NADP(H).

34. The method of claim 23, wherein the reaction is performed in a buffered aqueous reaction medium, at pH =6-8.

35. The method of claim 23, wherein glucose is used at an initial concentration of 10 mM to 3000 mM.

36. A method for producing an ursodesoxycholic acid compound (UDCA) of formula (1),

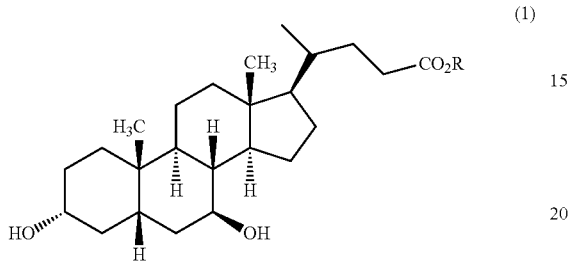

(1)

the method comprising:
a) biocatalytically reducing a dehydrocholic acid compound (DHCA) of formula (2)

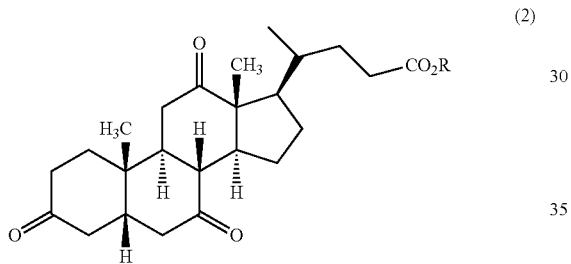

(2)

by the method of claim 23 to the corresponding 12-keto-ursodesoxycholic acid compound (12-keto UDCA) of formula (3)

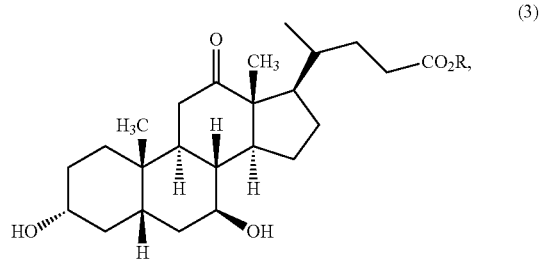

(3)

wherein in formulas (1), (2) and (3), R represents alkyl, H, a alkali metal ion or $N(R^3)_4^+$, wherein each of the $R^3$ residues is the same or different and represents H or alkyl, or the group —$CO_2R$ is replaced by the acid amide group —$CONR^1R^2$, wherein $R^1$ and $R^2$ each independently of one another represents an alkyl residue; and b) chemically reducing the 12-keto-UDCA of formula (3) to the UDCA compound of formula (1);

thereby producing an ursodesoxycholic acid compound (UDCA) of formula (1).

37. The method of claim 23, wherein the enzyme activity of the 7β-HSDH has a concentration of 100 to 1500 U/gBDM and the 3α-HSDH has a concentration of 50 to 500 U/gBDM.

* * * * *

SEQUENCE LISTING

<160> NUMBER OF SEQ ID NOS: 23

<210> SEQ ID NO 1
<211> LENGTH: 792
<212> TYPE: DNA
<213> ORGANISM: Collinsella aerofaciens
<220> FEATURE:
<221> NAME/KEY: CDS
<222> LOCATION: (1)..(789)

<400> SEQUENCE: 1

| | | | | | | | | | | | | | | | | |
|---|---|---|---|---|---|---|---|---|---|---|---|---|---|---|---|---|
| atg | aac | ctg | agg | gag | aag | tac | ggt | gag | tgg | ggc | ctg | atc | ctg | ggc | gcg | 48 |
| Met | Asn | Leu | Arg | Glu | Lys | Tyr | Gly | Glu | Trp | Gly | Leu | Ile | Leu | Gly | Ala | |
| 1 | | | | 5 | | | | | 10 | | | | | 15 | | |

| acc | gag | ggc | gtc | ggc | aag | gcg | ttc | tgc | gag | aag | atc | gcc | gcc | ggc | ggc | 96 |
|---|---|---|---|---|---|---|---|---|---|---|---|---|---|---|---|---|
| Thr | Glu | Gly | Val | Gly | Lys | Ala | Phe | Cys | Glu | Lys | Ile | Ala | Ala | Gly | Gly | |
| | | | 20 | | | | | 25 | | | | | 30 | | | |

| atg | aac | gtc | gtc | atg | gtc | ggc | cgt | cgc | gag | gag | aag | ctg | aac | gtg | ctc | 144 |
|---|---|---|---|---|---|---|---|---|---|---|---|---|---|---|---|---|
| Met | Asn | Val | Val | Met | Val | Gly | Arg | Arg | Glu | Glu | Lys | Leu | Asn | Val | Leu | |
| | | | 35 | | | | | 40 | | | | | 45 | | | |

| gca | ggc | gag | atc | cgc | gag | acc | tac | ggc | gtg | gag | acc | aag | gtc | gtg | cgc | 192 |
|---|---|---|---|---|---|---|---|---|---|---|---|---|---|---|---|---|
| Ala | Gly | Glu | Ile | Arg | Glu | Thr | Tyr | Gly | Val | Glu | Thr | Lys | Val | Val | Arg | |
| 50 | | | | | 55 | | | | | 60 | | | | | | |

| gcc | gac | ttt | agc | cag | ccc | ggc | gct | gcc | gag | acc | gtc | ttc | gcc | gcg | acc | 240 |
|---|---|---|---|---|---|---|---|---|---|---|---|---|---|---|---|---|
| Ala | Asp | Phe | Ser | Gln | Pro | Gly | Ala | Ala | Glu | Thr | Val | Phe | Ala | Ala | Thr | |
| 65 | | | | | 70 | | | | | 75 | | | | | 80 | |

| gag | ggc | ctg | gac | atg | ggc | ttc | atg | agc | tac | gtg | gcc | tgc | ctg | cac | agc | 288 |
|---|---|---|---|---|---|---|---|---|---|---|---|---|---|---|---|---|
| Glu | Gly | Leu | Asp | Met | Gly | Phe | Met | Ser | Tyr | Val | Ala | Cys | Leu | His | Ser | |
| | | | | 85 | | | | | 90 | | | | | 95 | | |

| ttc | ggt | aag | atc | cag | gac | acc | ccc | tgg | gag | aag | cac | gag | gcc | atg | atc | 336 |
|---|---|---|---|---|---|---|---|---|---|---|---|---|---|---|---|---|
| Phe | Gly | Lys | Ile | Gln | Asp | Thr | Pro | Trp | Glu | Lys | His | Glu | Ala | Met | Ile | |
| | | | 100 | | | | | 105 | | | | | 110 | | | |

| aac | gtc | aac | gtc | gtg | acc | ttc | ctc | aag | tgc | ttc | cac | cac | tac | atg | cgg | 384 |
|---|---|---|---|---|---|---|---|---|---|---|---|---|---|---|---|---|
| Asn | Val | Asn | Val | Val | Thr | Phe | Leu | Lys | Cys | Phe | His | His | Tyr | Met | Arg | |
| | | | 115 | | | | | 120 | | | | | 125 | | | |

| atc | ttt | gcc | gcc | cag | gac | cgc | ggc | gcc | gtg | atc | aac | gtc | tcg | tcg | atg | 432 |
|---|---|---|---|---|---|---|---|---|---|---|---|---|---|---|---|---|
| Ile | Phe | Ala | Ala | Gln | Asp | Arg | Gly | Ala | Val | Ile | Asn | Val | Ser | Ser | Met | |
| | 130 | | | | | 135 | | | | | 140 | | | | | |

| acc | ggc | atc | agc | tcc | agc | ccc | tgg | aac | ggc | cag | tac | ggc | gcg | ggc | aag | 480 |
|---|---|---|---|---|---|---|---|---|---|---|---|---|---|---|---|---|
| Thr | Gly | Ile | Ser | Ser | Ser | Pro | Trp | Asn | Gly | Gln | Tyr | Gly | Ala | Gly | Lys | |
| 145 | | | | | 150 | | | | | 155 | | | | | 160 | |

| gcc | ttc | atc | ctc | aag | atg | acc | gag | gcc | gtg | gcc | tgc | gag | tgc | gag | ggc | 528 |
|---|---|---|---|---|---|---|---|---|---|---|---|---|---|---|---|---|
| Ala | Phe | Ile | Leu | Lys | Met | Thr | Glu | Ala | Val | Ala | Cys | Glu | Cys | Glu | Gly | |
| | | | | 165 | | | | | 170 | | | | | 175 | | |

| acc | ggc | gtc | gac | gtc | gag | gtc | atc | acc | ctc | ggc | acc | acc | cta | acc | ccc | 576 |
|---|---|---|---|---|---|---|---|---|---|---|---|---|---|---|---|---|
| Thr | Gly | Val | Asp | Val | Glu | Val | Ile | Thr | Leu | Gly | Thr | Thr | Leu | Thr | Pro | |
| | | | 180 | | | | | 185 | | | | | 190 | | | |

| agc | ctg | ctg | tcc | aac | ctc | ccc | ggc | ggc | ccg | cag | ggc | gag | gcc | gtc | atg | 624 |
|---|---|---|---|---|---|---|---|---|---|---|---|---|---|---|---|---|
| Ser | Leu | Leu | Ser | Asn | Leu | Pro | Gly | Gly | Pro | Gln | Gly | Glu | Ala | Val | Met | |
| | | | 195 | | | | | 200 | | | | | 205 | | | |

| aag | atc | gcc | ctc | acc | ccc | gag | gag | tgc | gtt | gac | gag | gcc | ttt | gag | aag | 672 |
|---|---|---|---|---|---|---|---|---|---|---|---|---|---|---|---|---|
| Lys | Ile | Ala | Leu | Thr | Pro | Glu | Glu | Cys | Val | Asp | Glu | Ala | Phe | Glu | Lys | |
| 210 | | | | | 215 | | | | | 220 | | | | | | |

| ctg | ggt | aag | gag | ctc | tcc | gtc | atc | gcc | ggc | cag | cgc | aac | aag | gac | tcc | 720 |
|---|---|---|---|---|---|---|---|---|---|---|---|---|---|---|---|---|
| Leu | Gly | Lys | Glu | Leu | Ser | Val | Ile | Ala | Gly | Gln | Arg | Asn | Lys | Asp | Ser | |
| 225 | | | | | 230 | | | | | 235 | | | | | 240 | |

| gtc | cac | gac | tgg | aag | gca | aac | cac | acc | gag | gac | gag | tac | atc | cgc | tac | 768 |
|---|---|---|---|---|---|---|---|---|---|---|---|---|---|---|---|---|
| Val | His | Asp | Trp | Lys | Ala | Asn | His | Thr | Glu | Asp | Glu | Tyr | Ile | Arg | Tyr | |
| | | | | 245 | | | | | 250 | | | | | 255 | | |

| atg | ggg | tcg | ttc | tac | cgc | gac | tag | | | | | | | | | 792 |
|---|---|---|---|---|---|---|---|---|---|---|---|---|---|---|---|---|
| Met | Gly | Ser | Phe | Tyr | Arg | Asp | | | | | | | | | | |

<210> SEQ ID NO 2
<211> LENGTH: 263
<212> TYPE: PRT
<213> ORGANISM: Collinsella aerofaciens

<400> SEQUENCE: 2

```
Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Gly Arg Arg Glu Glu Lys Leu Asn Val Leu
        35                  40                  45

Ala Gly Glu Ile Arg Glu Thr Tyr Gly Val Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260
```

<210> SEQ ID NO 3
<211> LENGTH: 774
<212> TYPE: DNA
<213> ORGANISM: Comamonas testosteroni
<220> FEATURE:
<221> NAME/KEY: CDS
<222> LOCATION: (1)..(771)

<400> SEQUENCE: 3

```
atg tcc atc atc gtg ata agc ggc tgc gcc acc ggc att ggt gcc gct    48
Met Ser Ile Ile Val Ile Ser Gly Cys Ala Thr Gly Ile Gly Ala Ala
1               5                   10                  15 acg cgc aag gtc ctg gag gcg gcc ggt cac cag atc gta ggc atc gat    96
Thr Arg Lys Val Leu Glu Ala Ala Gly His Gln Ile Val Gly Ile Asp
            20                  25                  30
```

```
ata cgc gat gcg gaa gtg att gcc gat ctc tcg acg gcc gaa ggt cga    144
Ile Arg Asp Ala Glu Val Ile Ala Asp Leu Ser Thr Ala Glu Gly Arg
         35                  40                  45 aag cag gcg att gcc gat gta ctg gcg aag tgc agc aag ggc atg gac    192
Lys Gln Ala Ile Ala Asp Val Leu Ala Lys Cys Ser Lys Gly Met Asp
 50                  55                  60 ggc ctg gtg ctg tgc gcc ggc ctg gga ccg cag acc aag gtg ctt ggc    240
Gly Leu Val Leu Cys Ala Gly Leu Gly Pro Gln Thr Lys Val Leu Gly
 65                  70                  75                  80 aat gtg gtt tcg gtc aat tat ttt ggc gcg acc gag ctg atg gat gcc    288
Asn Val Val Ser Val Asn Tyr Phe Gly Ala Thr Glu Leu Met Asp Ala
                 85                  90                  95 ttt ttg cca gcg ctg aaa aaa ggc cat cag ccc gca gcc gtc gtc atc    336
Phe Leu Pro Ala Leu Lys Lys Gly His Gln Pro Ala Ala Val Val Ile
            100                 105                 110 tcg tcc gtg gct tcc gcg cat ctg gct ttt gac aag aac cca ctg gcg    384
Ser Ser Val Ala Ser Ala His Leu Ala Phe Asp Lys Asn Pro Leu Ala
        115                 120                 125 ctg gca ctg gaa gcc ggc gag gaa gcc aag gcc cgc gcc att gtc gaa    432
Leu Ala Leu Glu Ala Gly Glu Glu Ala Lys Ala Arg Ala Ile Val Glu
130                 135                 140 cat gcg gga gag cag ggc gga aat ctg gcc tat gcg ggc agc aag aat    480
His Ala Gly Glu Gln Gly Gly Asn Leu Ala Tyr Ala Gly Ser Lys Asn
145                 150                 155                 160 gct ttg acg gtg gct gtg cgc aaa cgc gcc gcc gcc tgg ggc gag gct    528
Ala Leu Thr Val Ala Val Arg Lys Arg Ala Ala Ala Trp Gly Glu Ala
                165                 170                 175 ggc gtg cgc ctg aac acc atc gcc ccc ggt gca acc gag act ccc ttg    576
Gly Val Arg Leu Asn Thr Ile Ala Pro Gly Ala Thr Glu Thr Pro Leu
            180                 185                 190 ctg cag gcg ggc ctg cag gac ccg cgc tat ggc gaa tcc att gcc aag    624
Leu Gln Ala Gly Leu Gln Asp Pro Arg Tyr Gly Glu Ser Ile Ala Lys
        195                 200                 205 ttc gtt cct ccc atg ggc cgc cgt gcc gag ccg tcc gag atg gcg tcg    672
Phe Val Pro Pro Met Gly Arg Arg Ala Glu Pro Ser Glu Met Ala Ser
210                 215                 220 gtc atc gcc ttt ttg atg agc ccg gcc gca agc tat gtg cat ggc gcg    720
Val Ile Ala Phe Leu Met Ser Pro Ala Ala Ser Tyr Val His Gly Ala
225                 230                 235                 240 cag atc gtc att gat ggc ggc att gat gcg gtg atg cgc ccg aca cag    768
Gln Ile Val Ile Asp Gly Gly Ile Asp Ala Val Met Arg Pro Thr Gln
                245                 250                 255 ttc tga                                                            774
Phe

<210> SEQ ID NO 4
<211> LENGTH: 257
<212> TYPE: PRT
<213> ORGANISM: Comamonas testosteroni

<400> SEQUENCE: 4

Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Arg Asp Ala Glu Val Ile Ala Asp Leu Ser Thr Ala Glu Gly Arg
        35                  40                  45

Lys Gln Ala Ile Ala Asp Val Leu Ala Lys Cys Ser Lys Gly Met Asp
    50                  55                  60
```

Gly Leu Val Leu Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
                85                  90                  95

Phe Leu Pro Ala Leu Lys Lys Gly His Gln Pro Ala Ala Val Val Ile
            100                 105                 110

Ser Ser Val Ala Ser Ala His Leu Ala Phe Asp Lys Asn Pro Leu Ala
        115                 120                 125

Leu Ala Leu Glu Ala Gly Glu Glu Ala Lys Ala Arg Ala Ile Val Glu
    130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Trp Gly Glu Ala
                165                 170                 175

Gly Val Arg Leu Asn Thr Ile Ala Pro Gly Ala Thr Glu Thr Pro Leu
                180                 185                 190

Leu Gln Ala Gly Leu Gln Asp Pro Arg Tyr Gly Glu Ser Ile Ala Lys
    195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe

<210> SEQ ID NO 5
<211> LENGTH: 768
<212> TYPE: DNA
<213> ORGANISM: Escherichia coli
<220> FEATURE:
<221> NAME/KEY: CDS
<222> LOCATION: (1)..(765)

<400> SEQUENCE: 5

```
gtg ttt aat tct gac aac ctg aga ctc gac gga aaa tgc gcc atc atc    48
Val Phe Asn Ser Asp Asn Leu Arg Leu Asp Gly Lys Cys Ala Ile Ile
1               5                   10                  15 aca ggt gcg ggt gca ggt att ggt aaa gaa atc gcc att aca ttc gcg    96
Thr Gly Ala Gly Ala Gly Ile Gly Lys Glu Ile Ala Ile Thr Phe Ala
            20                  25                  30 aca gct ggc gca tct gtg gtg gtc agt gat att aac gcc gac gca gct   144
Thr Ala Gly Ala Ser Val Val Val Ser Asp Ile Asn Ala Asp Ala Ala
        35                  40                  45 aac cat gtt gta gac gaa att caa caa ctg ggt ggt cag gca ttt gcc   192
Asn His Val Val Asp Glu Ile Gln Gln Leu Gly Gly Gln Ala Phe Ala
    50                  55                  60 tgc cgt tgt gat att act tcc gaa cag gaa ctc tct gca ctg gca gac   240
Cys Arg Cys Asp Ile Thr Ser Glu Gln Glu Leu Ser Ala Leu Ala Asp
65                  70                  75                  80 ttt gct atc agt aag ctg ggt aaa gtt gat att ctg gtt aac aac gcc   288
Phe Ala Ile Ser Lys Leu Gly Lys Val Asp Ile Leu Val Asn Asn Ala
                85                  90                  95 ggt ggc ggt gga cct aaa ccg ttt gat atg cca atg gcg gat ttt cgc   336
Gly Gly Gly Gly Pro Lys Pro Phe Asp Met Pro Met Ala Asp Phe Arg
            100                 105                 110 cgt gct tat gaa ctg aat gtg ttt tct ttt ttc cat ctg tca caa ctt   384
```

-continued

```
Arg Ala Tyr Glu Leu Asn Val Phe Ser Phe His Leu Ser Gln Leu
            115                 120                 125 gtt gcg cca gaa atg gaa aaa aat ggc ggt ggc gtt att ctg acc atc       432
Val Ala Pro Glu Met Glu Lys Asn Gly Gly Gly Val Ile Leu Thr Ile
130                 135                 140 act tct atg gcg gca gaa aat aaa aat ata aac atg act tcc tat gca       480
Thr Ser Met Ala Ala Glu Asn Lys Asn Ile Asn Met Thr Ser Tyr Ala
145                 150                 155                 160 tca tct aaa gct gcg gcc agt cat ctg gtc aga aat atg gcg ttt gac       528
Ser Ser Lys Ala Ala Ala Ser His Leu Val Arg Asn Met Ala Phe Asp
                165                 170                 175 cta ggt gaa aaa aat att cgg gta aat ggc att gcg ccg ggg gca ata       576
Leu Gly Glu Lys Asn Ile Arg Val Asn Gly Ile Ala Pro Gly Ala Ile
            180                 185                 190 tta acc gat gcc ctg aaa tcc gtt att aca cca gaa att gaa caa aaa       624
Leu Thr Asp Ala Leu Lys Ser Val Ile Thr Pro Glu Ile Glu Gln Lys
        195                 200                 205 atg tta cag cac acg ccg atc aga cgt ctg ggc caa ccg caa gat att       672
Met Leu Gln His Thr Pro Ile Arg Arg Leu Gly Gln Pro Gln Asp Ile
210                 215                 220 gct aac gca gcg ctg ttc ctt tgc tcg cct gct gcg agc tgg gta agc       720
Ala Asn Ala Ala Leu Phe Leu Cys Ser Pro Ala Ala Ser Trp Val Ser
225                 230                 235                 240 gga caa att ctc acc gtc tcc ggt ggt ggg gta cag gag ctc aat taa       768
Gly Gln Ile Leu Thr Val Ser Gly Gly Gly Val Gln Glu Leu Asn
                245                 250                 255
```

<210> SEQ ID NO 6
<211> LENGTH: 255
<212> TYPE: PRT
<213> ORGANISM: Escherichia coli

<400> SEQUENCE: 6

```
Val Phe Asn Ser Asp Asn Leu Arg Leu Asp Gly Lys Cys Ala Ile Ile
1               5                   10                  15

Thr Gly Ala Gly Ala Gly Ile Gly Lys Glu Ile Ala Ile Thr Phe Ala
                20                  25                  30

Thr Ala Gly Ala Ser Val Val Ser Asp Ile Asn Ala Asp Ala Ala
            35                  40                  45

Asn His Val Val Asp Glu Ile Gln Gln Leu Gly Gly Gln Ala Phe Ala
        50                  55                  60

Cys Arg Cys Asp Ile Thr Ser Glu Gln Glu Leu Ser Ala Leu Ala Asp
65                  70                  75                  80

Phe Ala Ile Ser Lys Leu Gly Lys Val Asp Ile Leu Val Asn Asn Ala
                85                  90                  95

Gly Gly Gly Gly Pro Lys Pro Phe Asp Met Pro Met Ala Asp Phe Arg
            100                 105                 110

Arg Ala Tyr Glu Leu Asn Val Phe Ser Phe Phe His Leu Ser Gln Leu
        115                 120                 125

Val Ala Pro Glu Met Glu Lys Asn Gly Gly Val Ile Leu Thr Ile
    130                 135                 140

Thr Ser Met Ala Ala Glu Asn Lys Asn Ile Asn Met Thr Ser Tyr Ala
145                 150                 155                 160

Ser Ser Lys Ala Ala Ala Ser His Leu Val Arg Asn Met Ala Phe Asp
                165                 170                 175

Leu Gly Glu Lys Asn Ile Arg Val Asn Gly Ile Ala Pro Gly Ala Ile
            180                 185                 190
```

Leu Thr Asp Ala Leu Lys Ser Val Ile Thr Pro Glu Ile Glu Gln Lys
            195                 200                 205

Met Leu Gln His Thr Pro Ile Arg Arg Leu Gly Gln Pro Gln Asp Ile
    210                 215                 220

Ala Asn Ala Ala Leu Phe Leu Cys Ser Pro Ala Ala Ser Trp Val Ser
225                 230                 235                 240

Gly Gln Ile Leu Thr Val Ser Gly Gly Val Gln Glu Leu Asn
                245                 250                 255

<210> SEQ ID NO 7
<211> LENGTH: 786
<212> TYPE: DNA
<213> ORGANISM: Bacillus subtilis

<400> SEQUENCE: 7
atgtatccgg atttaaaagg aaaagtcgtc gctattacag agctgcttc agggctcgga      60 aaggcgatgg ccattcgctt cggcaaggag caggcaaaag tggttatcaa ctattatagt    120
aataaacaag atccgaacga ggtaaaagaa gaggtcatca aggcgggcgg tgaagctgtt    180
gtcgtccaag gagatgtcac gaaagaggaa gatgtaaaaa atatcgtgca acggcaatt     240 aaggagttcg gcacactcga tattatgatt aataatgccg gtcttgaaaa tcctgtgcca    300
tctcacgaaa tgccgctcaa ggattgggat aaagtcatcg gcacgaactt aacgggtgcc    360
tttttaggaa gccgtgaagc gattaaatat ttcgtagaaa acgatatcaa gggaaatgtc    420
attaacatgt ccagtgtgca cgaagtgatt ccttggccgt tatttgtcca ctatgcggca    480
agtaaaggcg gataaagct gatgacagaa acattagcgt ggaatacgc gccgaagggc     540 attcgcgtca ataatattgg gccaggtgcg atcaacacgc caatcaatgc tgaaaaattc    600
gctgacccta acagaaaagc tgatgtgaaa agcatgattc aatgggata tatcggcgaa    660 ccggaggaga tcgccgcagt agcagcctgg cttgcttcga aggaagccag ctacgtcaca    720
ggcatcacgt tattcgcgga cggcggtatg acacaatatc cttcattcca ggcaggccgc    780
ggttaa                                                              786

<210> SEQ ID NO 8
<211> LENGTH: 261
<212> TYPE: PRT
<213> ORGANISM: Bacillus subtilis

<400> SEQUENCE: 8

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

```
Lys Tyr Phe Val Glu Asn Asp Ile Lys Gly Asn Val Ile Asn Met Ser
            130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 9
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide derived from Collinsella aerofaciens (G39D)

<400> SEQUENCE: 9

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
                20                  25                  30

Met Asn Val Val Met Val Asp Arg Arg Glu Glu Lys Leu Asn Val Leu
            35                  40                  45

Ala Gly Glu Ile Arg Glu Thr Tyr Gly Val Glu Thr Lys Val Val Arg
50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
130                 135                 140

Thr Gly Ile Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
```

```
                210                 215                 220
Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
            245                 250                 255

Met Gly Ser Phe Tyr Arg Asp
        260

<210> SEQ ID NO 10
<211> LENGTH: 263
<212> TYPE: PRT
<213> ORGANISM: Artificial Sequence
<220> FEATURE:
<223> OTHER INFORMATION: Description of Artificial Sequence: Synthetic
      7Beta-HSDH mutant polypeptide

<400> SEQUENCE: 10

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Asp Ile Arg Glu Glu Lys Leu Asn Val Leu
        35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
130                 135                 140

Thr Gly Ile Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 11
<211> LENGTH: 263
<212> TYPE: PRT
<213> ORGANISM: Artificial Sequence
<220> FEATURE:
```

<223> OTHER INFORMATION: Description of Artificial Sequence: Synthetic
      7Beta-HSDH mutant polypeptide

<400> SEQUENCE: 11

```
Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Asp Phe Arg Glu Glu Lys Leu Asn Val Leu
        35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260
```

<210> SEQ ID NO 12
<211> LENGTH: 263
<212> TYPE: PRT
<213> ORGANISM: Artificial Sequence
<220> FEATURE:
<223> OTHER INFORMATION: Description of Artificial Sequence: Synthetic
      7Beta-HSDH mutant polypeptide

<400> SEQUENCE: 12

```
Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Asp Phe Lys Glu Glu Lys Leu Asn Val Leu
        35                  40                  45

Ala Gly Glu Ile Arg Glu Thr Tyr Gly Val Glu Thr Lys Val Val Arg
    50                  55                  60
```

```
Ala Asp Phe Ser Gln Pro Gly Ala Ala Glu Thr Val Phe Ala Ala Thr
 65                  70                  75                  80

Glu Gly Leu Asp Met Gly Phe Met Ser Tyr Val Ala Cys Leu His Ser
                 85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
                180                 185                 190

Ser Leu Leu Ser Asn Leu Pro Gly Gly Pro Gln Gly Ala Val Met
            195                 200                 205

Lys Ile Ala Leu Thr Pro Glu Glu Cys Val Asp Glu Ala Phe Glu Lys
210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 13
<211> LENGTH: 263
<212> TYPE: PRT
<213> ORGANISM: Artificial Sequence
<220> FEATURE:
<223> OTHER INFORMATION: Description of Artificial Sequence: Synthetic
      7Beta-HSDH mutant polypeptide

<400> SEQUENCE: 13

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
                20                  25                  30

Met Asn Val Val Met Val Asp Phe Lys Glu Glu Gly Leu Asn Val Leu
            35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Ala Thr
 65                  70                  75                  80

Glu Gly Leu Asp Met Gly Phe Met Ser Tyr Val Ala Cys Leu His Ser
                 85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160
```

```
Ala Phe Ile Leu Lys Met Thr Glu Ala Val Ala Cys Glu Cys Glu Gly
            165                 170                 175

Thr Gly Val Asp Val Glu Val Ile Thr Leu Gly Thr Thr Leu Thr Pro
        180                 185                 190

Ser Leu Leu Ser Asn Leu Pro Gly Gly Pro Gln Gly Glu Ala Val Met
    195                 200                 205

Lys Ile Ala Leu Thr Pro Glu Glu Cys Val Asp Glu Ala Phe Glu Lys
210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260
```

```
<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtcgtcatg gtcgactttc gcgagg                                          26

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccgccgcatc cataccgcca gttgtttacc c                                    31

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgtcgtcatg gtcgactttta aagaggagaa gctg                                34

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: a, c, t or g

<400> SEQUENCE: 17
gtcgacttta aagaggagnd tctgaacgtg ctc                                  33
```

<210> SEQ ID NO 18
<211> LENGTH: 7891
<212> TYPE: DNA
<213> ORGANISM: Artificial Sequence
<220> FEATURE:
<223> OTHER INFORMATION: Description of Artificial Sequence: Synthetic Plasmid p7(A)T3rG-A polynucleotide

<400> SEQUENCE: 18

| | | | | | |
|---|---|---|---|---|---|
| atccggatat | agttcctcct | ttcagcaaaa | aaccccctcaa | gacccgttta | gaggccccaa | 60 |
| ggggttatgc | tagttattgc | tcagcggtgg | cagcagccaa | ctcagcttcc | tttcgggctt | 120 |
| tgttagcagc | cggatctcag | tggtggtggt | ggtggtgctc | gagttaaccg | cggcctgcct | 180 |
| ggaatgaagg | atattgtgtc | ataccgccgt | ccgcgaataa | cgtgatgcct | gtgacgtagc | 240 |
| tggcttcctt | cgaagcaagc | caggctgcta | ctgcggcgat | ctcctccggt | tcgccgatat | 300 |
| atcccattgg | aatcatgctt | tctacatcag | ctttctgttt | agggtcagcg | aattttcag | 360 |
| cattgattgg | cgtgttgatc | gcacctggcc | caatattatt | gacgcgaatg | cccttcggcg | 420 |
| cgtattccaa | cgctaatgtt | tctgtcatca | gctttatccc | gcctttactt | gccgcatagt | 480 |
| ggacaaataa | cggccaagga | atcacttcgt | gcacactgga | catgttaatg | acatttccct | 540 |
| tgatatcgtt | ttctacgaaa | tatttaatcg | cttcacggct | tcctaaaaag | gcacccgtta | 600 |
| agttcgtgcc | gatgacttta | tcccaatcct | tgagcggcat | ttcgtgagat | ggcacaggat | 660 |
| tttcaagacc | ggcattatta | atcataatat | cgagtgtgcc | gaactcctta | attgccgttt | 720 |
| gcacgatatt | ttttacatct | tcctctttcg | tgacatctcc | ttggacgaca | acagcttcac | 780 |
| cgcccgcctt | gatgacctct | tcttttacct | cgttcggatc | ttgtttatta | ctataatagt | 840 |
| tgataaccac | ttttgcctgc | tccttgccga | agcgaatggc | catcgccttt | ccgagccctg | 900 |
| aagcagctcc | tgtaatagcg | acgacttttc | cttttaaatc | cggatacatg | tatatctcct | 960 |
| tgcggccgct | cagaactgtg | tcgggcgcat | caccgcatca | atgccgccat | caatgacgat | 1020 |
| ctgcgcgcca | tgcacatagc | ttgcggccgg | gctcatcaaa | aaggcgatga | ccgacgccat | 1080 |
| ctcggacggc | tcggcacggc | ggcccatggg | aggaacgaac | ttggcaatgg | attcgccata | 1140 |
| gcgcgggtcc | tgcaggcccg | cctgcagcaa | gggagtctcg | gttgcaccgg | gggcgatggt | 1200 |
| gttcaggcgc | acgccagcct | cgccccaggc | ggcggcgcgt | ttgcgcacag | ccaccgtcaa | 1260 |
| agcattcttg | ctgcccgcat | aggccagatt | tccgccctgc | tctcccgcat | gttcgacaat | 1320 |
| ggcgcgggcc | ttggcttcct | cgccggcttc | cagtgccagc | gccagtgggt | tcttgtcaaa | 1380 |
| agccagatgc | gcggaagcca | cggacgagat | gacgacggct | gcgggctgat | ggccttttt | 1440 |
| cagcgctggc | aaaaaggcat | ccatcagctc | ggtcgcgcca | aaataattga | ccgaaaccac | 1500 |
| attgccaagc | accttggtct | gcggtcccag | gccggcgcac | agcaccaggc | cgtccatgcc | 1560 |
| cttgctgcac | ttcgccagta | catcggcaat | cgcctgcttt | cgaccttcgg | ccgtcgagag | 1620 |
| atcggcaatc | acttccgcat | cgcgtatatc | gatgcctacg | atctggtgac | cggccgcctc | 1680 |
| caggaccttg | cgcgtagcgg | caccaatgcc | ggtggcgcag | ccgcttatca | cgatgatgga | 1740 |
| catcatatgt | atatctcctt | cttatactta | actaatatac | taagatgggg | aattgttatc | 1800 |
| cgctcacaat | tccccatatag | tgagtcgtat | taatttcgat | tatgcggccg | tgtacaatac | 1860 |
| gattactttc | tgttcgactt | aagcattata | agcttctagt | cgcggtagaa | cgaccccatg | 1920 |
| tagcggatgt | actcgtcctc | ggtgtggttt | gccttccagt | cgtggacgga | gtccttgttg | 1980 |
| cgctggccgg | cgatgacgga | gagctcctta | cccagcttct | caaaggcctc | gtcaacgcac | 2040 |
| tcctcggggg | tgagggcgat | cttcatgacg | gcctcgccct | gcgggccgcc | ggggaggttg | 2100 |

```
gacagcaggc tgggggttag ggtggtgccg agggtgatga cctcgacgtc gacgccggtg    2160
ccctcgcact cgcaggccac ggcctcggtc atcttgagga tgaaggcctt gcccgcgccg    2220
tactggccgt tccagggggct ggagctgatg ccggtcatcg acgagacgtt gatcacggcg   2280
```

```
gacagcaggc tgggggttag ggtggtgccg agggtgatga cctcgacgtc gacgccggtg    2160
ccctcgcact cgcaggccac ggcctcggtc atcttgagga tgaaggcctt gcccgcgccg    2220
tactggccgt tccagggct  ggagctgatg ccggtcatcg acgagacgtt gatcacggcg    2280
ccgcggtcct gggcggcaaa gatccgcatg tagtggtgga agcacttgag gaaggtcacg    2340
acgttgacgt tgatcatggc ctcgtgcttc tcccaggggg tgtcctggat cttaccgaag    2400
ctgtgcaggc aggccacgta gctcatgaag cccatgtcca ggcctcggt  cgcggcgaag    2460 acggtctcgg cagcgccggg ctggctaaag tcggcgcgca cgaccttggt ctccacgccg    2520
taggtctcgc ggatctcgcc tgcgagcacg ttcagcttct cctcgcgacg ggcgaccatg    2580
acgacgttca tgccgccggc ggcgatcttc tcgcagaacg ccttgccgac gccctcggtc    2640
gcgcccagga tcaggcccca ctcaccgtac ttctccctca ggttcatatg tatatctcct    2700
tcttaaagtt aaacaaaatt atttctagag gggaattgtt atccgctcac aattccccta    2760
tagtgagtcg tattaatttc gcgggatcga gatctcgatc ctctacgccg gacgcatcgt    2820
ggccggcatc accggcgcca caggtgcggt tgctggcgcc tatatcgccg acatcaccga    2880
tggggaagat cgggctcgcc acttcgggct catgagcgct tgtttcggcg tgggtatggt    2940
ggcaggcccc gtggccgggg gactgttggg cgccatctcc ttgcatgcac cattccttgc    3000
ggcggcggtg ctcaacggcc tcaacctact actgggctgc ttcctaatgc aggagtcgca    3060
taagggagag cgtcgagatc ccggacacca tcgaatggcg caaaaccttt cgcggtatgg    3120
catgatagcg cccggaagag agtcaattca gggtggtgaa tgtgaaacca gtaacgttat    3180
acgatgtcgc agagtatgcc ggtgtctctt atcagaccgt ttcccgcgtg gtgaaccagg    3240
ccagccacgt ttctgcgaaa acgcgggaaa aagtggaagc ggcgatggcg gagctgaatt    3300
acattcccaa ccgcgtggca caacaactgg cgggcaaaca gtcgttgctg attggcgttg    3360
ccacctccag tctggccctg cacgcgccgt cgcaaattgt cgcggcgatt aaatctcgcg    3420
ccgatcaact gggtgccagc gtggtggtgt cgatggtaga acgaagcggc gtcgaagcct    3480
gtaaagcggc ggtgcacaat cttctcgcgc aacgcgtcag tgggctgatc attaactatc    3540
cgctggatga ccaggatgcc attgctgtgg aagctgcctg cactaatgtt ccggcgttat    3600
ttcttgatgt ctctgaccag acacccatca acagtattat tttctcccat gaagacggta    3660
cgcgactggg cgtggagcat ctggtcgcat tgggtcacca gcaaatcgcg ctgttagcgg    3720
gcccattaag ttctgtctcg gcgcgtctgc gtctggctgg ctggcataaa tatctcactc    3780
gcaatcaaat tcagccgata gcggaacggg aaggcgactg gagtgccatg tccggttttc    3840
aacaaaccat gcaaatgctg aatgagggca tcgttcccac tgcgatgctg gttgccaacg    3900
atcagatggc gctgggcgca atgcgcgcca ttaccgagtc cgggctgcgc gttggtgcgg    3960
atatctcggt agtgggatac gacgataccg aagacagctc atgttatatc ccgccgttaa    4020
ccaccatcaa acaggatttt cgcctgctgg ggcaaaccag cgtggaccgc ttgctgcaac    4080
tctctcaggg ccaggcggtg aagggcaatc agctgttgcc cgtctcactg gtgaaaagaa    4140
aaaccaccct ggcgcccaat acgcaaaccg cctctccccg cgcgttggcc gattcattaa    4200
tgcagctggc acgacaggtt tcccgactgg aaagcgggca gtgagcgcaa cgcaattaat    4260
gtaagttagc tcactcatta ggcaccggga tctcgaccga tgcccttgag agccttcaac    4320
ccagtcagct ccttccggtg ggcgcggggc atgactatcg tcgccgcact tatgactgtc    4380
ttctttatca tgcaactcgt aggacaggtg ccggcagcgc tctgggtcat tttcggcgag    4440
```

```
gaccgctttc gctggagcgc gacgatgatc ggcctgtcgc ttgcggtatt cggaatcttg   4500
cacgccctcg ctcaagcctt cgtcactggt cccgccacca aacgtttcgg cgagaagcag   4560
gccattatcg ccggcatggc ggccccacgg gtgcgcatga tcgtgctcct gtcgttgagg   4620
acccggctag gctggcgggg ttgccttact ggttagcaga atgaatcacc gatacgcgag   4680
cgaacgtgaa gcgactgctg ctgcaaaacg tctgcgacct gagcaacaac atgaatggtc   4740
ttcggtttcc gtgtttcgta aagtctggaa acgcggaagt cagcgccctg caccattatg   4800
ttccggatct gcatcgcagg atgctgctgg ctaccctgtg gaacacctac atctgtatta   4860
acgaagcgct ggcattgacc ctgagtgatt tttctctggt cccgccgcat ccataccgcc   4920
agttgtttac cctcacaacg ttccagtaac cgggcatgtt catcatcagt aacccgtatc   4980
gtgagcatcc tctctcgttt catcggtatc attaccccca tgaacagaaa tccccctttac  5040 acggaggcat cagtgaccaa acaggaaaaa accgccctta acatggcccg ctttatcaga   5100
agccagacat taacgcttct ggagaaactc aacgagctgg acgcggatga acaggcagac   5160
atctgtgaat cgcttcacga ccacgctgat gagctttacc gcagctgcct cgcgcgtttc   5220
ggtgatgacg gtgaaaacct ctgacacatg cagctcccgg agacggtcac agcttgtctg   5280
taagcggatg ccgggagcag acaagcccgt cagggcgcgt cagcgggtgt tggcgggtgt   5340
cggggcgcag ccatgaccca gtcacgtagc gatagcggag tgtatactgg cttaactatg   5400
cggcatcaga gcagattgta ctgagagtgc accatatatg cggtgtgaaa taccgcacag   5460
atgcgtaagg agaaaatacc gcatcaggcg ctcttccgct tcctcgctca ctgactcgct   5520
gcgctcggtc gttcggctgc ggcgagcggt atcagctcac tcaaaggcgg taatacggtt   5580
atccacagaa tcaggggata acgcaggaaa gaacatgtga gcaaaaggcc agcaaaaggc   5640
caggaaccgt aaaaaggccg cgttgctggc gtttttccat aggctccgcc cccctgacga   5700
gcatcacaaa aatcgacgct caagtcagag gtggcgaaac ccgacaggac tataaagata   5760
ccaggcgttt ccccctggaa gctccctcgt gcgctctcct gttccgaccc tgccgcttac   5820
cggatacctg tccgcctttc tcccttcggg aagcgtggcg ctttctcata gctcacgctg   5880
taggtatctc agttcggtgt aggtcgttcg ctccaagctg ggctgtgtgc acgaaccccc   5940
cgttcagccc gaccgctgcg ccttatccgg taactatcgt cttgagtcca acccggtaag   6000
acacgactta tcgccactgg cagcagccac tggtaacagg attagcagag cgaggtatgt   6060
aggcggtgct acagagttct tgaagtggtg gcctaactac ggctacacta aggacagt     6120 atttggtatc tgcgctctgc tgaagccagt taccttcgga aaagagttg gtagctcttg    6180 atccggcaaa caaaccaccg ctggtagcgg tggtttttttt gtttgcaagc agcagattac   6240
gcgcagaaaa aaggatctca agaagatcc tttgatcttt tctacggggt ctgacgctca    6300
gtggaacgaa aactcacgtt aagggatttt ggtcatgaga ttatcaaaaa ggatcttcac    6360
ctagatcctt ttaaattaaa aatgaagttt taaatcaatc taaagtatat atgagtaaac    6420
ttggtctgac agttaccaat gcttaatcag tgaggcacct atctcagcga tctgtctatt    6480
tcgttcatcc atagttgcct gactccccgt cgtgtagata actacgatac gggagggctt    6540
accatctggc cccagtgctg caatgatacc gcgagaccca cgctcaccgg ctccagattt    6600
atcagcaata aaccagccag ccggaagggc cgagcgcaga agtggtcctg caactttatc    6660
cgcctccatc cagtctatta attgttgccg ggaagctaga gtaagtagtt cgccagttaa    6720 tagtttcgc aacgttgttg ccattgctgc aggcatcgtg gtgtcacgct cgtcgtttgg     6780
tatggcttca ttcagctccg gttcccaacg atcaaggcga gttacatgat cccccatgtt   6840
```

```
gtgcaaaaaa gcggttagct ccttcggtcc tccgatcgtt gtcagaagta agttggccgc    6900
agtgttatca ctcatggtta tggcagcact gcataattct cttactgtca tgccatccgt    6960
aagatgcttt tctgtgactg gtgagtactc aaccaagtca ttctgagaat agtgtatgcg    7020
gcgaccgagt tgctcttgcc cggcgtcaat acgggataat accgcgccac atagcagaac    7080
tttaaaagtg ctcatcattg gaaaacgttc ttcggggcga aaactctcaa ggatcttacc    7140
gctgttgaga tccagttcga tgtaacccac tcgtgcaccc aactgatctt cagcatcttt    7200
tactttcacc agcgtttctg ggtgagcaaa acaggaagg caaaatgccg caaaaaggg    7260 aataagggcg acacggaaat gttgaatact catactcttc ctttttcaat attattgaag    7320
catttatcag ggttattgtc tcatgagcgg atacatattt gaatgtattt agaaaaataa    7380
acaaataggg gttccgcgca catttccccg aaaagtgcca cctgaaattg taaacgttaa    7440
tattttgtta aaattcgcgt taaattttg ttaaatcagc tcattttta accaataggc    7500 cgaaatcggc aaaatccctt ataaatcaaa agaatagacc gagataggt tgagtgttgt    7560 tccagtttgg aacaagagtc cactattaaa gaacgtggac tccaacgtca aagggcgaaa    7620
aaccgtctat cagggcgatg gcccactacg tgaaccatca ccctaatcaa gttttttggg    7680
gtcgaggtgc cgtaaagcac taaatcggaa ccctaaaggg agcccccgat ttagagcttg    7740
acggggaaag ccggcgaacg tggcgagaaa ggaagggaag aaagcgaaag gagcgggcgc    7800
tagggcgctg gcaagtgtag cggtcacgct gcgcgtaacc accacacccg ccgcgcttaa    7860
tgcgccgcta cagggcgcgt cccattcgcc a                                  7891
```

<210> SEQ ID NO 19
<211> LENGTH: 7758
<212> TYPE: DNA
<213> ORGANISM: Artificial Sequence
<220> FEATURE:
<223> OTHER INFORMATION: Description of Artificial Sequence: Synthetic
    Plasmid p7(A)T3rG-K polynucleotide

<400> SEQUENCE: 19

```
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagttaaccg cggcctgcct    180
ggaatgaagg atattgtgtc ataccgccgt ccgcgaataa cgtgatgcct gtgacgtagc    240
tggcttcctt cgaagcaagc caggctgcta ctgcggcgat ctcctccggt cgccgatat    300 atcccattgg aatcatgctt tctacatcag ctttctgttt agggtcagcg aattttttcag    360 cattgattgg cgtgttgatc gcacctggcc caatattatt gacgcgaatg cccttcggcg    420
cgtattccaa cgctaatgtt tctgtcatca gctttatccc gcctttactt gccgcatagt    480
ggacaaataa cggccaagga atcacttcgt gcacactgga catgttaatg acatttccct    540
tgatatcgtt ttctacgaaa tatttaatcg cttcacggct tcctaaaaag gcacccgtta    600
agttcgtgcc gatgacttta tcccaatcct tgagcggcat ttcgtgagat ggcacaggat    660
tttcaagacc ggcattatta atcataatat cgagtgtgcc gaactcctta attgccgttt    720
gcacgatatt ttttacatct tcctctttcg tgacatctcc ttggacgaca acagcttcac    780
cgcccgcctt gatgacctct tcttttacct cgttcggatc ttgttattta ctataatagt    840
tgataaccac ttttgcctgc tccttgccga agcgaatggc catcgccttt ccgagccctg    900
aagcagctcc tgtaatagcg acgactttcct cttttaaatc cggatacatg tatatctcct    960
```

```
tgcggccgct cagaactgtg tcgggcgcat caccgcatca atgccgccat caatgacgat    1020
ctgcgcgcca tgcacatagc ttgcggccgg gctcatcaaa aaggcgatga ccgacgccat    1080
ctcggacggc tcggcacggc ggcccatggg aggaacgaac ttggcaatgg attcgccata    1140
gcgcgggtcc tgcaggcccg cctgcagcaa gggagtctcg gttgcaccgg gggcgatggt    1200
gttcaggcgc acgccagcct cgcccaggc ggcggcgcgt ttgcgcacag ccaccgtcaa     1260
agcattcttg ctgcccgcat aggccagatt tccgccctgc tctcccgcat gttcgacaat    1320
ggcgcgggcc ttggcttcct cgccggcttc cagtgccagc gccagtgggt tcttgtcaaa    1380
agccagatgc gcggaagcca cggacgagat gacgacggct gcgggctgat ggcctttttt    1440
cagcgctggc aaaaaggcat ccatcagctc ggtcgcgcca aataattga ccgaaaccac     1500
attgccaagc accttggtct gcggtcccag gccggcgcac agcaccaggc cgtccatgcc    1560
cttgctgcac ttcgccagta catcggcaat cgcctgcttt cgaccttcgg ccgtcgagag    1620
atcggcaatc acttccgcat cgcgtatatc gatgcctacg atctggtgac cggccgcctc    1680
caggaccttg cgcgtagcgg caccaatgcc ggtggcgcag ccgcttatca cgatgatgga    1740
catcatatgt atatctcctt cttatactta actaatatac taagatgggg aattgttatc    1800
cgctcacaat tcccctatag tgagtcgtat taatttcgat tatgcggccg tgtacaatac    1860
gattactttc tgttcgactt aagcattata agcttctagt cgcggtagaa cgaccccatg    1920
tagcggatgt actcgtcctc ggtgtggttt gccttccagt cgtggacgga gtccttgttg    1980
cgctggccgg cgatgacgga gagctcctta cccagcttct caaaggcctc gtcaacgcac    2040
tcctcggggg tgagggcgat cttcatgacg gcctcgccct gcggccgcc ggggaggttg     2100
gacagcaggc tgggggttag ggtggtgccg agggtgatga cctcgacgtc gacgccggtg    2160
ccctcgcact cgcaggccac ggcctcggtc atcttgagga tgaaggcctt gcccgcgccg    2220
tactggccgt tccaggggct ggagctgatg ccggtcatcg acgagacgtt gatcacggcg    2280
ccgcggtcct gggcggcaaa gatccgcatg tagtggtgga agcacttgag gaaggtcacg    2340
acgttgacgt tgatcatggc ctcgtgcttc tcccaggggg tgtcctggat cttaccgaag    2400
ctgtgcaggc aggccacgta gctcatgaag cccatgtcca ggcccctcggt cgcggcgaag   2460
acggtctcgg cagcgccggg ctggctaaag tcggcgcgca cgaccttggt ctccacgccg    2520
taggtctcgc ggatctcgcc tgcgagcacg ttcagcttct cctcgcgacg ggcgaccatg    2580
acgacgttca tgccgccggc ggcgatcttc tcgcagaacg ccttgccgac gccctcggtc    2640
gcgcccagga tcaggcccca ctcaccgtac ttctccctca ggttcatatg tatatctcct    2700
tcttaaagtt aaacaaaatt atttctagag gggaattgtt atccgctcac aattccccta    2760
tagtgagtcg tattaatttc gcgggatcga gatctcgatc ctctacgccg gacgcatcgt    2820
ggccggcatc accggcgcca caggtgcggt tgctggcgcc tatatcgccg acatcaccga    2880
tggggaagat cgggctcgcc acttcgggct catgagcgct tgtttcggcg tgggtatggt    2940
ggcaggcccc gtggccgggg gactgttggg cgccatctcc ttgcatgcac cattccttgc    3000
ggcggcggtg ctcaacggcc tcaacctact actgggctgc ttcctaatgc aggagtcgca    3060
taagggagag cgtcgagatc ccggacacca tcgaatggcc aaaacccttt cgcggtatgg    3120
catgatagcg cccggaagag agtcaattca gggtggtgaa tgtgaaacca gtaacgttat    3180
acgatgtcgc agagtatgcc ggtgtctctt atcagaccgt ttcccgcgtg gtgaaccagg    3240
ccagccacgt ttctgcgaaa acgcgggaaa aagtggaagc ggcgatggcg gagctgaatt    3300
```

```
acattcccaa ccgcgtggca caacaactgg cgggcaaaca gtcgttgctg attggcgttg    3360
ccacctccag tctggccctg cacgcgccgt cgcaaattgt cgcggcgatt aaatctcgcg    3420
ccgatcaact gggtgccagc gtggtggtgt cgatggtaga acgaagcggc gtcgaagcct    3480
gtaaagcggc ggtgcacaat cttctcgcgc aacgcgtcag tgggctgatc attaactatc    3540
cgctggatga ccaggatgcc attgctgtgg aagctgcctg cactaatgtt ccggcgttat    3600
ttcttgatgt ctctgaccag acacccatca acagtattat tttctcccat gaagacggta    3660
cgcgactggg cgtggagcat ctggtcgcat tgggtcacca gcaaatcgcg ctgttagcgg    3720
gcccattaag ttctgtctcg gcgcgtctgc gtctggctgg ctggcataaa tatctcactc    3780
gcaatcaaat tcagccgata gcggaacggg aaggcgactg gagtgccatg tccggttttc    3840
aacaaaccat gcaaatgctg aatgagggca tcgttcccac tgcgatgctg gttgccaacg    3900
atcagatggc gctgggcgca atgcgcgcca ttaccgagtc cgggctgcgc gttggtgcgg    3960
atatctcggt agtgggatac gacgataccg aagacagctc atgttatatc ccgccgttaa    4020
ccaccatcaa acaggatttt cgcctgctgg ggcaaaccag cgtggaccgc ttgctgcaac    4080
tctctcaggg ccaggcggtg aagggcaatc agctgttgcc cgtctcactg gtgaaaagaa    4140
aaaccaccct ggcgcccaat acgcaaaccg cctctccccg cgcgttggcc gattcattaa    4200
tgcagctggc acgacaggtt tcccgactgg aaagcgggca gtgagcgcaa cgcaattaat    4260
gtaagttagc tcactcatta ggcaccggga tctcgaccga tgcccttgag agccttcaac    4320
ccagtcagct ccttccggtg ggcgcggggc atgactatcg tcgccgcact tatgactgtc    4380
ttctttatca tgcaactcgt aggacaggtg ccggcagcgc tctgggtcat tttcggcgag    4440
gaccgctttc gctggagcgc gacgatgatc ggcctgtcgc ttgcggtatt cggaatcttg    4500
cacgccctcg ctcaagcctt cgtcactggt cccgccacca aacgtttcgg cgagaagcag    4560
gccattatcg ccggcatggc ggcccacgg gtgcgcatga tcgtgctcct gtcgttgagg    4620
acccggctag gctggcgggg ttgccttact ggttagcaga atgaatcacc gatacgcgag    4680
cgaacgtgaa gcgactgctg ctgcaaaacg tctgcgacct gagcaacaac atgaatggtc    4740
ttcggtttcc gtgtttcgta aagtctggaa acgcggaagt cagcgccctg caccattatg    4800
ttccggatct gcatcgcagg atgctgctgg ctaccctgtg gaacacctac atctgtatta    4860
acgaagcgct ggcattgacc ctgagtgatt tttctctggt cccgccgcat ccataccgcc    4920
agttgtttac cctcacaacg ttccagtaac cgggcatgtt catcatcagt aacccgtatc    4980
gtgagcatcc tctctcgttt catcggtatc attaccccca tgaacagaaa tcccccttac    5040
acggaggcat cagtgaccaa acaggaaaaa accgccctta acatggcccg ctttatcaga    5100
agccagacat taacgcttct ggagaaactc aacgagctgg acgcggatga acaggcagac    5160
atctgtgaat cgcttcacga ccacgctgat gagctttacc gcagctgcct cgcgcgtttc    5220
ggtgatgacg gtgaaaacct ctgacacatg cagctcccgg agacggtcac agcttgtctg    5280
taagcggatg ccgggagcag acaagcccgt cagggcgcgt cagcgggtgt tggcgggtgt    5340
cggggcgcag ccatgaccca gtcacgtagc gatagcggag tgtatactgg cttaactatg    5400
cggcatcaga gcagattgta ctgagagtgc accatatatg cggtgtgaaa taccgcacag    5460
atgcgtaagg agaaaatacc gcatcaggcg ctcttccgct tcctcgctca ctgactcgct    5520
gcgctcggtc gttcggctgc ggcgagcggt atcagctcac tcaaaggcgg taatacggtt    5580
atccacagaa tcaggggata acgcaggaaa gaacatgtga gcaaaaggcc agcaaaaggc    5640
caggaaccgt aaaaaggccg cgttgctggc gttttccat aggctccgcc cccctgacga    5700
```

```
gcatcacaaa aatcgacgct caagtcagag gtggcgaaac ccgacaggac tataaagata   5760
ccaggcgttt ccccctggaa gctccctcgt gcgctctcct gttccgaccc tgccgcttac   5820
cggatacctg tccgcctttc tcccttcggg aagcgtggcg ctttctcata gctcacgctg   5880
taggtatctc agttcggtgt aggtcgttcg ctccaagctg ggctgtgtgc acgaaccccc   5940
cgttcagccc gaccgctgcg ccttatccgg taactatcgt cttgagtcca acccggtaag   6000
acacgactta tcgccactgg cagcagccac tggtaacagg attagcagag cgaggtatgt   6060
aggcggtgct acagagttct tgaagtggtg gcctaactac ggctacacta aaggacagt    6120 atttggtatc tgcgctctgc tgaagccagt taccttcgga aaaagagttg gtagctcttg   6180
atccggcaaa caaaccaccg ctggtagcgg tggttttttt gtttgcaagc agcagattac   6240
gcgcagaaaa aaaggatctc aagaagatcc tttgatcttt tctacggggt ctgacgctca   6300
gtggaacgaa aactcacgtt aagggatttt ggtcatgaac aataaaactg tctgcttaca   6360
taaacagtaa tacaaggggt gttatgagcc atattcaacg ggaaacgtct tgctctaggc   6420
cgcgattaaa ttccaacatg gatgctgatt tatatgggta taaatgggct cgcgataatg   6480
tcgggcaatc aggtgcgaca atctatcgat tgtatgggaa gcccgatgcg ccagagttgt   6540
ttctgaaaca tggcaaaggt agcgttgcca atgatgttac agatgagatg gtcagactaa   6600
actggctgac ggaatttatg cctcttccga ccatcaagca ttttatccgt actcctgatg   6660
atgcatggtt actcaccact gcgatccccg gaaaacagc attccaggta ttagaagaat    6720
atcctgattc aggtgaaaat attgttgatg cgctggcagt gttcctgcgc cggttgcatt   6780
cgattcctgt ttgtaattgt cctttttaaca gcgatcgcgt atttcgtctc gctcaggcgc   6840
aatcacgaat gaataacggt ttggttgatg cgagtgattt tgatgacgag cgtaatggct   6900
ggcctgttga acaagtctgg aaagaaatgc ataaactttt gccattctca ccggattcag   6960
tcgtcactca tggtgatttc tcacttgata accttatttt tgacgagggg aaattaatag   7020
gttgtattga tgttggacga gtcggaatcg cagaccgata ccaggatctt gccatcctat   7080
ggaactgcct cggtgagttt tctccttcat tacagaaacg ctttttcaa aaatatggta    7140 ttgataatcc tgatatgaat aaattgcagt ttcatttgat gctcgatgag ttttttctaag  7200 aattaattca tgagcggata catatttgaa tgtatttaga aaataaaca aatagggggtt   7260 ccgcgcacat ttccccgaaa agtgccacct gaaattgtaa acgttaatat tttgttaaaa   7320
ttcgcgttaa attttgtta aatcagctca ttttttaacc aataggccga atcggcaaa    7380 atcccttata aatcaaaaga atagaccgag atagggttga gtgttgttcc agtttggaac   7440
aagagtccac tattaaagaa cgtggactcc aacgtcaaag ggcgaaaaac cgtctatcag   7500
ggcgatggcc cactacgtga accatcaccc taatcaagtt ttttggggtc gaggtgccgt   7560
aaagcactaa atcggaaccc taaagggagc ccccgattta gagcttgacg gggaaagccg   7620
gcgaacgtgg cgagaaagga agggaagaaa gcgaaaggag cgggcgctag gcgctggca    7680 agtgtagcgg tcacgctgcg cgtaaccacc acacccgccg cgcttaatgc gccgctacag   7740
ggcgcgtccc attcgcca                                                  7758
```

<210> SEQ ID NO 20
<211> LENGTH: 8019
<212> TYPE: DNA
<213> ORGANISM: Artificial Sequence
<220> FEATURE:
<223> OTHER INFORMATION: Description of Artificial Sequence: Synthetic
      Plasmid p7(A)T3TG-A polynucleotide

<400> SEQUENCE: 20

```
atccggatat agttcctcct ttcagcaaaa aacccctcaa gacccgttta gaggccccaa    60
ggggttatgc tagttattgc tcagcggtgg cagcagccaa ctcagcttcc tttcgggctt   120
tgttagcagc cggatctcag tggtggtggt ggtggtgctc gagttaaccg cggcctgcct   180
ggaatgaagg atattgtgtc ataccgccgt ccgcgaataa cgtgatgcct gtgacgtagc   240
tggcttcctt cgaagcaagc caggctgcta ctgcggcgat ctcctccggt cgccgatat    300
atcccattgg aatcatgctt tctacatcag ctttctgttt agggtcagcg aattttcag    360
cattgattgg cgtgttgatc gcacctggcc caatattatt gacgcgaatg cccttcggcg   420
cgtattccaa cgctaatgtt tctgtcatca gctttatccc gcctttactt gccgcatagt   480
ggacaaataa cggccaagga atcacttcgt gcacactgga catgttaatg acatttccct   540
tgatatcgtt ttctacgaaa tatttaatcg cttcacggct tcctaaaaag gcacccgtta   600
agttcgtgcc gatgacttta tcccaatcct tgagcggcat ttcgtgagat ggcacaggat   660
tttcaagacc ggcattatta atcataatat cgagtgtgcc gaactcctta attgccgttt   720
gcacgatatt ttttacatct tcctctttcg tgacatctcc ttggacgaca acagcttcac   780
cgcccgcctt gatgacctct tcttttacct cgttcggatc ttgtttatta ctataatagt   840
tgataaccac ttttgcctgc tccttgccga agcgaatggc catcgccttt ccgagccctg   900
aagcagctcc tgtaatagcg acgacttttc cttttaaatc cggatacata tgtatatctc   960
cttcttatac ttaactaata tactaagatg gggaattgtt atccgctcac aattcccta  1020
tagtgagtcg tattaatttc gattatgcgg ccgtgtacaa tacgattact ttctgttcga  1080
cttaagcatt atgcggccgc tcagaactgt gtcgggcgca tcaccgcatc aatgccgcca  1140
tcaatgacga tctgcgcgcc atgcacatag cttgcggccg ggctcatcaa aaaggcgatg  1200
accgacgcca tctcggacgg ctcggcacgg cggcccatgg gaggaacgaa cttggcaatg  1260
gattcgccat agcgcgggtc ctgcaggccc gcctgcagca agggagtctc ggttgcaccg  1320
ggggcgatgg tgttcaggcg cacgccagcc tcgccccagg cggcggcgcg tttgcgcaca  1380
gccaccgtca aagcattctt gctgcccgca taggccagat ttccgccctg ctctcccgca  1440
tgttcgacaa tggcgcgggc cttggcttcc tcgccggctt ccagtgccag cgccagtggg  1500
ttcttgtcaa aagccagatg cgcggaagcc acggacgaga tgacgacggc tgcgggctga  1560
tggcctttt tcagcgctgg caaaaaggca tccatcagct cggtcgcgcc aaaataattg  1620
accgaaacca cattgccaag caccttggtc tgcggtccca ggccggcgca cagcaccagg  1680
ccgtccatgc ccttgctgca cttcgccagt acatcggcaa tcgcctgctt tcgaccttcg  1740
gccgtcgaga gatcggcaat cacttccgca tcgcgtatat cgatgcctac gatctggtga  1800
ccggccgcct ccaggacctt gcgcgtagcg gcaccaatgc cggtggcgca gccgcttatc  1860
acgatgatgg acatatgtat atctccttct tatacttaac taatatacta agatggggaa  1920
tgttatccg ctcacaattc ccctatagtg agtcgtatta atttcgatta gcggccgtg  1980
tacaatacga ttactttctg ttcgacttaa gcattataag cttctagtcg cggtagaacg  2040
accccatgta gcggatgtac tcgtcctcgg tgtggtttgc cttccagtcg tggacggagt  2100
ccttgttgcg ctggccggcg atgacggaga gctccttacc cagcttctca aaggcctcgt  2160
caacgcactc ctcggggtg agggcgatct tcatgacggc ctcgccctgc gggccgccgg  2220
ggaggttgga cagcaggctg ggggttaggg tggtgccgag ggtgatgacc tcgacgtcga  2280
```

```
cgccggtgcc ctcgcactcg caggccacgg cctcggtcat cttgaggatg aaggccttgc    2340
ccgcgccgta ctggccgttc caggggctgg agctgatgcc ggtcatcgac gagacgttga    2400
tcacggcgcc gcggtcctgg gcggcaaaga tccgcatgta gtggtggaag cacttgagga    2460
aggtcacgac gttgacgttg atcatggcct cgtgcttctc ccaggggtg tcctggatct     2520 taccgaagct gtgcaggcag gccacgtagc tcatgaagcc catgtccagg ccctcggtcg    2580
cggcgaagac ggtctcggca gcgccgggct ggctaaagtc ggcgcgcacg accttggtct    2640
ccacgccgta ggtctcgcgg atctcgcctg cgagcacgtt cagcttctcc tcgcgacggg    2700
cgaccatgac gacgttcatg ccgccggcgg cgatcttctc gcagaacgcc ttgccgacgc    2760
cctcggtcgc gcccaggatc aggccccact caccgtactt ctccctcagg ttcatatgta    2820
tatctccttc ttaaagttaa acaaaattat ttctagaggg gaattgttat ccgctcacaa    2880 ttccccctata gtgagtcgta ttaatttcgc gggatcgaga tctcgatcct ctacgccgga    2940
cgcatcgtgg ccggcatcac cggcgccaca ggtgcggttg ctggcgccta tatcgccgac    3000
atcaccgatg gggaagatcg ggctcgccac ttcgggctca tgagcgcttg tttcggcgtg    3060
ggtatggtgg caggccccgt ggccggggga ctgttgggcg ccatctcctt gcatgcacca    3120
ttccttgcgg cggcggtgct caacggcctc aacctactac tgggctgctt cctaatgcag    3180
gagtcgcata agggagagcg tcgagatccc ggacaccatc gaatggcgca aaacctttcg    3240
cggtatggca tgatagcgcc cggaagagag tcaattcagg gtggtgaatg tgaaaccagt    3300
aacgttatac gatgtcgcag agtatgccgg tgtctcttat cagaccgttt ccgcgtggt     3360 gaaccaggcc agccacgttt ctgcgaaaac gcgggaaaaa gtggaagcgg cgatggcgga    3420
gctgaattac attcccaacc gcgtggcaca acaactggcg ggcaaacagt cgttgctgat    3480
tggcgttgcc acctccagtc tggccctgca cgcgccgtcg caaattgtcg cggcgattaa    3540
atctcgcgcc gatcaactgg gtgccagcgt ggtggtgtcg atggtagaac gaagcggcgt    3600
cgaagcctgt aaagcggcgg tgcacaatct tctcgcgcaa cgcgtcagtg ggctgatcat    3660
taactatccg ctggatgacc aggatgccat tgctgtggaa gctgcctgca ctaatgttcc    3720
ggcgttattt cttgatgtct ctgaccagac acccatcaac agtattattt ctcccatga    3780 agacggtacg cgactgggcg tggagcatct ggtcgcattg ggtcaccagc aaatcgcgct    3840
gttagcgggc ccattaagtt ctgtctcggc gcgtctgcgt ctggctggct ggcataaata    3900
tctcactcgc aatcaaattc agccgatagc ggaacgggaa ggcgactgga gtgccatgtc    3960
cggttttcaa caaaccatgc aaatgctgaa tgagggcatc gttcccactg cgatgctggt    4020
tgccaacgat cagatggcgc tgggcgcaat gcgcgccatt accgagtccg gctgcgcgt     4080 tggtgcggat atctcggtag tgggatacga cgataccgaa gacagctcat gttatatccc    4140
gccgttaacc accatcaaac aggattttcg cctgctgggg caaccagcg tggaccgctt     4200 gctgcaactc tctcagggcc aggcggtgaa gggcaatcag ctgttgcccg tctcactggt    4260
gaaaagaaaa accaccctgg cgcccaatac gcaaaccgcc tctccccgcg cgttggccga    4320
ttcattaatg cagctggcac gacaggtttc ccgactggaa agcgggcagt gagcgcaacg    4380
caattaatgt aagttagctc actcattagg caccgggat tcgaccgatg cccttgagag     4440
ccttcaaccc agtcagctcc ttccggtggg cgcggggcat gactatcgtc gccgcactta    4500
tgactgtctt ctttatcatg caactcgtag gacaggtgcc ggcagcgctc tgggtcattt    4560
tcggcgagga ccgctttcgc tggagcgcga cgatgatcgg cctgtcgctt gcggtattcg    4620
gaatcttgca cgccctcgct caagccttcg tcactggtcc cgccaccaaa cgtttcggcg    4680
```

```
agaagcaggc cattatcgcc ggcatggcgg ccccacgggt gcgcatgatc gtgctcctgt   4740
cgttgaggac ccggctaggc tggcggggtt gccttactgg ttagcagaat gaatcaccga   4800
tacgcgagcg aacgtgaagc gactgctgct gcaaaacgtc tgcgacctga gcaacaacat   4860
gaatggtctt cggtttccgt gtttcgtaaa gtctggaaac gcggaagtca gcgccctgca   4920
ccattatgtt ccggatctgc atcgcaggat gctgctggct accctgtgga cacctacat    4980
ctgtattaac gaagcgctgg cattgaccct gagtgatttt tctctggtcc cgccgcatcc   5040
ataccgccag ttgtttaccc tcacaacgtt ccagtaaccg ggcatgttca tcatcagtaa   5100
cccgtatcgt gagcatcctc tctcgtttca tcggtatcat taccccatg aacagaaatc    5160
ccccttacac ggaggcatca gtgaccaaac aggaaaaaac cgcccttaac atggcccgct   5220
ttatcagaag ccagacatta acgcttctgg agaaactcaa cgagctggac gcggatgaac   5280
aggcagacat ctgtgaatcg cttcacgacc acgctgatga gctttaccgc agctgcctcg   5340
cgcgtttcgg tgatgacggt gaaaacctct gacacatgca gctcccggag acggtcacag   5400
cttgtctgta agcggatgcc gggagcagac aagcccgtca gggcgcgtca gcgggtgttg   5460
gcgggtgtcg gggcgcagcc atgacccagt cacgtagcga tagcggagtg tatactggct   5520
taactatgcg gcatcagagc agattgtact gagagtgcac catatatgcg gtgtgaaata   5580
ccgcacagat gcgtaaggag aaaataccgc atcaggcgct cttccgcttc ctcgctcact   5640
gactcgctgc gctcggtcgt tcggctgcgg cgagcggtat cagctcactc aaaggcggta   5700
atacggttat ccacagaatc aggggataac gcaggaaaga acatgtgagc aaaaggccag   5760
caaaaggcca ggaaccgtaa aaaggccgcg ttgctggcgt ttttccatag gctccgcccc   5820
cctgacgagc atcacaaaaa tcgacgctca agtcagaggt ggcgaaaccc gacaggacta   5880
taaagatacc aggcgtttcc ccctggaagc tccctcgtgc gctctcctgt tccgaccctg   5940
ccgcttaccg gatacctgtc cgcctttctc ccttcgggaa gcgtggcgct ttctcatagc   6000
tcacgctgta ggtatctcag ttcggtgtag tcgttcgct  ccaagctggg ctgtgtgcac   6060
gaaccccccg ttcagcccga ccgctgcgcc ttatccggta actatcgtct tgagtccaac   6120
ccggtaagac acgacttatc gccactggca gcagccactg gtaacaggat tagcagagcg   6180
aggtatgtag gcggtgctac agagttcttg aagtggtggc ctaactacgg ctacactaga   6240
aggacagtat ttggtatctg cgctctgctg aagccagtta ccttcggaaa aagagttggt   6300
agctcttgat ccggcaaaca aaccaccgct ggtagcggtg ttttttttgt ttgcaagcag   6360
cagattacgc gcagaaaaaa aggatctcaa gaagatcctt tgatcttttc tacgggtct    6420
gacgctcagt ggaacgaaaa ctcacgttaa gggattttgg tcatgagatt atcaaaaagg   6480
atcttcacct agatcctttt aaattaaaaa tgaagtttta aatcaatcta agtatatat    6540
gagtaaactt ggtctgacag ttaccaatgc ttaatcagtg aggcacctat ctcagcgatc   6600
tgtctatttc gttcatccat agttgcctga ctccccgtcg tgtagataac tacgatacgg   6660
gagggcttac catctggccc cagtgctgca atgataccgc gagacccacg ctcaccggct   6720
ccagatttat cagcaataaa ccagccagcc ggaagggccg agcgcagaag tggtcctgca   6780
actttatccg cctccatcca gtctattaat tgttgccggg aagctagagt aagtagttcg   6840
ccagttaata gtttgcgcaa cgttgttgcc attgctgcag gcatcgtggt gtcacgctcg   6900
tcgtttggta tggcttcatt cagctccggt tcccaacgat caaggcgagt tacatgatcc   6960
cccatgttgt gcaaaaaagc ggttagctcc ttcggtcctc cgatcgttgt cagaagtaag   7020
```

| | |
|---|---|
| ttggccgcag tgttatcact catggttatg gcagcactgc ataattctct tactgtcatg | 7080 |
| ccatccgtaa gatgcttttc tgtgactggt gagtactcaa ccaagtcatt ctgagaatag | 7140 |
| tgtatgcggc gaccgagttg ctcttgcccg gcgtcaatac gggataatac cgcgccacat | 7200 |
| agcagaactt taaaagtgct catcattgga aaacgttctt cggggcgaaa actctcaagg | 7260 |
| atcttaccgc tgttgagatc cagttcgatg taacccactc gtgcacccaa ctgatcttca | 7320 |
| gcatctttta ctttcaccag cgtttctggg tgagcaaaaa caggaaggca aaatgccgca | 7380 |
| aaaaagggaa taagggcgac acggaaatgt tgaatactca tactcttcct ttttcaatat | 7440 |
| tattgaagca tttatcaggg ttattgtctc atgagcggat acatatttga atgtatttag | 7500 |
| aaaaataaac aaataggggt tccgcgcaca tttccccgaa aagtgccacc tgaaattgta | 7560 |
| aacgttaata ttttgttaaa attcgcgtta aattttttgtt aaatcagctc attttttaac | 7620 |
| caataggccg aaatcggcaa aatcccttat aaatcaaaag aatagaccga gatagggttg | 7680 |
| agtgttgttc cagtttggaa caagagtcca ctattaaaga acgtggactc caacgtcaaa | 7740 |
| gggcgaaaaa ccgtctatca gggcgatggc ccactacgtg aaccatcacc ctaatcaagt | 7800 |
| tttttggggt cgaggtgccg taaagcacta atcggaacc ctaaagggag ccccgatt | 7860 |
| agagcttgac ggggaaagcc ggcgaacgtg gcgagaaagg aagggaagaa agcgaaagga | 7920 |
| gcgggcgcta gggcgctggc aagtgtagcg gtcacgctgc gcgtaaccac cacacccgcc | 7980 |
| gcgcttaatg cgccgctaca gggcgcgtcc cattcgcca | 8019 |

<210> SEQ ID NO 21
<211> LENGTH: 7886
<212> TYPE: DNA
<213> ORGANISM: Artificial Sequence
<220> FEATURE:
<223> OTHER INFORMATION: Description of Artificial Sequence: Synthetic
    Plasmid p7(A)T3TG-K polynucleotide

<400> SEQUENCE: 21

| | |
|---|---|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagttaaccg cggcctgcct | 180 |
| ggaatgaagg atattgtgtc ataccgccgt ccgcgaataa cgtgatgcct gtgacgtagc | 240 |
| tggcttcctt cgaagcaagc caggctgcta ctgcggcgat ctcctccggt tcgccgatat | 300 |
| atcccattgg aatcatgctt tctacatcag cttttctgttt agggtcagcg aattttttcag | 360 |
| cattgattgg cgtgttgatc gcacctggcc caatattatt gacgcgaatg cccttcggcg | 420 |
| cgtattccaa cgctaatgtt tctgtcatca gctttatccc gcctttactt gccgcatagt | 480 |
| ggacaaataa cggccaagga atcacttcgt gcacactgga catgttaatg acatttccct | 540 |
| tgatatcgtt ttctacgaaa tatttaatcg cttcacggct tcctaaaaag gcacccgtta | 600 |
| agttcgtgcc gatgactta tcccaatcct tgagcggcat ttcgtgagat ggcacaggat | 660 |
| tttcaagacc ggcattatta atcataatat cgagtgtgcc gaactcctta attgccgttt | 720 |
| gcacgatatt ttttacatct tcctctttcg tgacatctcc ttggacgaca acagcttcac | 780 |
| cgcccgcctt gatgacctct tcttttacct cgttcggatc ttgttattta ctataatagt | 840 |
| tgataaccac ttttgcctgc tccttgccga agcgaatggc catcgccttt ccgagccctg | 900 |
| aagcagctcc tgtaatagcg acgacttttc cttttaaatc cggatacata tgtatatctc | 960 |
| cttcttatac ttaactaata tactaagatg gggaattgtt atccgctcac aattccccta | 1020 |

```
tagtgagtcg tattaatttc gattatgcgg ccgtgtacaa tacgattact ttctgttcga    1080
cttaagcatt atgcggccgc tcagaactgt gtcgggcgca tcaccgcatc aatgccgcca    1140
tcaatgacga tctgcgcgcc atgcacatag cttgcggccg ggctcatcaa aaaggcgatg    1200
accgacgcca tctcggacgg ctcggcacgg cggcccatgg gaggaacgaa cttggcaatg    1260
gattcgccat agcgcgggtc ctgcaggccc gcctgcagca agggagtctc ggttgcaccg    1320
ggggcgatgg tgttcaggcg cacgccagcc tcgcccagg cggcggcgcg tttgcgcaca     1380
gccaccgtca aagcattctt gctgcccgca taggccagat ttccgccctg ctctcccgca    1440
tgttcgacaa tggcgcgggc cttggcttcc tcgccggctt ccagtgccag cgccagtggg    1500
ttcttgtcaa aagccagatg cgcggaagcc acggacgaga tgacgacggc tgcgggctga    1560 tggcctttt tcagcgctgg caaaaaggca tccatcagct cggtcgcgcc aaaataattg      1620
accgaaacca cattgccaag caccttggtc tgcggtccca ggccggcgca cagcaccagg    1680
ccgtccatgc ccttgctgca cttcgccagt acatcggcaa tcgcctgctt tcgaccttcg    1740
gccgtcgaga gatcggcaat cacttccgca tcgcgtatat cgatgcctac gatctggtga    1800
ccggccgcct ccaggacctt gcgcgtagcg gcaccaatgc cggtggcgca gccgcttatc    1860
acgatgatgg acatatgtat atctccttct tatacttaac taatatacta agatggggaa    1920
ttgttatccg ctcacaattc ccctatagtg agtcgtatta atttcgatta tgcggccgtg    1980
tacaatacga ttactttctg ttcgacttaa gcattataag cttctagtcg cggtagaacg    2040
accccatgta gcggatgtac tcgtcctcgg tgtggtttgc cttccagtcg tggacggagt    2100
ccttgttgcg ctggccggcg atgacggaga gctccttacc cagcttctca aaggcctcgt    2160
caacgcactc ctcggggtg agggcgatct tcatgacggc ctcgccctgc gggccgccgg    2220
ggaggttgga cagcaggctg ggggttaggg tggtgccgag ggtgatgacc tcgacgtcga    2280
cgccggtgcc ctcgcactcg caggccacgg cctcggtcat cttgaggatg aaggccttgc    2340
ccgcgccgta ctgccgttc caggggctgg agctgatgcc ggtcatcgac gagacgttga     2400
tcacggcgcc gcggtcctgg gcggcaaaga tccgcatgta gtggtggaag cacttgagga    2460
aggtcacgac gttgacgttg atcatggcct cgtgcttctc ccaggggtg tcctggatct     2520 taccgaagct gtgcaggcag gccacgtagc tcatgaagcc catgtccagg ccctcggtcg    2580
cggcgaagac ggtctcggca gcgccgggct ggctaaagtc ggcgcgcacg accttggtct    2640
ccacgccgta ggtctcgcgg atctcgcctg cgagcacgtt cagcttctcc tcgcgacggg    2700
cgaccatgac gacgttcatg ccgccggcgg cgatcttctc gcagaacgcc ttgccgacgc    2760
cctcggtcgc gcccaggatc aggccccact caccgtactt ctccctcagg ttcatatgta    2820
tatctccttc ttaaagttaa acaaaattat ttctagaggg gaattgttat ccgctcacaa    2880 ttccctata gtgagtcgta ttaatttcgc gggatcgaga tctcgatcct ctacgccgga    2940
cgcatcgtgg ccggcatcac cggcgccaca ggtgcggttg ctggcgccta tatccgcgac    3000
atcaccgatg gggaagatcg ggctcgccac ttcgggctca tgagcgcttg tttcggcgtg    3060
ggtatggtgg caggccccgt ggccggggga ctgttgggcg ccatctcctt gcatgcacca    3120
ttccttgcgg cggcggtgct caacggcctc aacctactac tgggctgctt cctaatgcag    3180
gagtcgcata agggagagcg tcgagatccc ggacaccatc gaatggcgca aaacctttcg    3240
cggtatggca tgatagcgcc cggaagagag tcaattcagg gtggtgaatg tgaaaccagt    3300
aacgttatac gatgtcgcag agtatgccgg tgtctcttat cagaccgttt ccgcgtggt     3360 gaaccaggcc agccacgttt ctgcgaaaac gcgggaaaaa gtggaagcgg cgatggcgga    3420
```

```
gctgaattac attcccaacc gcgtggcaca acaactggcg ggcaaacagt cgttgctgat    3480
tggcgttgcc acctccagtc tggccctgca cgcgccgtcg caaattgtcg cggcgattaa    3540
atctcgcgcc gatcaactgg gtgccagcgt ggtggtgtcg atggtagaac gaagcggcgt    3600
cgaagcctgt aaagcggcgg tgcacaatct tctcgcgcaa cgcgtcagtg ggctgatcat    3660
taactatccg ctggatgacc aggatgccat tgctgtggaa gctgcctgca ctaatgttcc    3720
ggcgttattt cttgatgtct ctgaccagac acccatcaac agtattattt ctcccatga    3780 agacggtacg cgactgggcg tggagcatct ggtcgcattg ggtcaccagc aaatcgcgct    3840
gttagcgggc ccattaagtt ctgtctcggc gcgtctgcgt ctggctggct ggcataaata    3900
tctcactcgc aatcaaattc agccgatagc ggaacgggaa ggcgactgga gtgccatgtc    3960
cggttttcaa caaaccatgc aaatgctgaa tgagggcatc gttcccactg cgatgctggt    4020
tgccaacgat cagatggcgc tgggcgcaat gcgcgccatt accgagtccg ggctgcgcgt    4080
tggtgcggat atctcggtag tgggatacga cgataccgaa gacagctcat gttatatccc    4140
gccgttaacc accatcaaac aggattttcg cctgctgggg caaaccagcg tggaccgctt    4200
gctgcaactc tctcagggcc aggcggtgaa gggcaatcag ctgttgcccg tctcactggt    4260
gaaaagaaaa accaccctgg cgcccaatac gcaaaccgcc tctccccgcg cgttggccga    4320
ttcattaatg cagctggcac gacaggtttc ccgactggaa agcgggcagt gagcgcaacg    4380
caattaatgt aagttagctc actcattagg caccgggatc tcgaccgatg cccttgagag    4440
ccttcaaccc agtcagctcc ttccggtggg cgcggggcat gactatcgtc gccgcactta    4500
tgactgtctt ctttatcatg caactcgtag gacaggtgcc ggcagcgctc tgggtcattt    4560
tcggcgagga ccgctttcgc tggagcgcga cgatgatcgg cctgtcgctt gcggtattcg    4620
gaatcttgca cgccctcgct caagccttcg tcactggtcc cgccaccaaa cgtttcggcg    4680
agaagcaggc cattatcgcc ggcatggcgg ccccacgggt gcgcatgatc gtgctcctgt    4740
cgttgaggac ccggctaggc tggcggggtt gccttactgg ttagcagaat gaatcaccga    4800
tacgcgagcg aacgtgaagc gactgctgct gcaaaacgtc tgcgacctga gcaacaacat    4860
gaatggtctt cggtttccgt gtttcgtaaa gtctggaaac gcggaagtca gcgccctgca    4920
ccattatgtt ccggatctgc atcgcaggat gctgctggct accctgtgga acacctacat    4980
ctgtattaac gaagcgctgg cattgaccct gagtgatttt tctctggtcc cgccgcatcc    5040
ataccgccag ttgtttaccc tcacaacgtt ccagtaaccg ggcatgttca tcatcagtaa    5100
cccgtatcgt gagcatcctc tctcgtttca tcggtatcat taccccatg aacagaaatc    5160 cccttacac ggaggcatca gtgaccaaac aggaaaaaac cgcccttaac atggcccgct    5220
ttatcagaag ccagacatta acgcttctgg agaaactcaa cgagctggac gcggatgaac    5280
aggcagacat ctgtgaatcg cttcacgacc acgctgatga gctttaccgc agctgcctcg    5340
cgcgtttcgt tgatgacggt gaaaacctct gacacatgca gctcccggag acggtcacag    5400
cttgtctgta agcggatgcc gggagcagac aagcccgtca gggcgcgtca gcgggtgttg    5460
gcgggtgtcg gggcgcagcc atgacccagt cacgtagcga tagcggagtg tatactggct    5520
taactatgcg gcatcagagc agattgtact gagagtgcac catatatgcg gtgtgaaata    5580
ccgcacagat gcgtaaggag aaaataccgc atcaggcgct cttccgcttc ctcgctcact    5640
gactcgctgc gctcggtcgt tcggctgcgg cgagcggtat cagctcactc aaaggcggta    5700
atacggttat ccacagaatc aggggataac gcaggaaaga acatgtgagc aaaaggccag    5760
```

```
caaaaggcca ggaaccgtaa aaaggccgcg ttgctggcgt ttttccatag gctccgcccc    5820
cctgacgagc atcacaaaaa tcgacgctca agtcagaggt ggcgaaaccc gacaggacta    5880
taaagatacc aggcgtttcc ccctggaagc tccctcgtgc gctctcctgt tccgaccctg    5940
ccgcttaccg gatacctgtc cgcctttctc ccttcgggaa gcgtggcgct ttctcatagc    6000
tcacgctgta ggtatctcag ttcggtgtag gtcgttcgct ccaagctggg ctgtgtgcac    6060
gaaccccccg ttcagcccga ccgctgcgcc ttatccggta actatcgtct tgagtccaac    6120
ccggtaagac acgacttatc gccactggca gcagccactg gtaacaggat tagcagagcg    6180
aggtatgtag gcggtgctac agagttcttg aagtggtggc ctaactacgg ctacactaga    6240
aggacagtat ttggtatctg cgctctgctg aagccagtta ccttcggaaa aagagttggt    6300
agctcttgat ccggcaaaca aaccaccgct ggtagcggtg gtttttttgt ttgcaagcag    6360
cagattacgc gcagaaaaaa aggatctcaa gaagatcctt tgatctttc tacggggtct    6420 gacgctcagt ggaacgaaaa ctcacgttaa gggattttgg tcatgaacaa taaaactgtc    6480
tgcttacata acagtaata caaggggtgt tatgagccat attcaacggg aaacgtcttg    6540
ctctaggccg cgattaaatt ccaacatgga tgctgattta tatgggtata atgggctcg    6600 cgataatgtc gggcaatcag gtgcgacaat ctatcgattg tatgggaagc ccgatgcgcc    6660
agagttgttt ctgaaacatg gcaaaggtag cgttgccaat gatgttacag atgagatggt    6720
cagactaaac tggctgacgg aatttatgcc tcttccgacc atcaagcatt ttatccgtac    6780
tcctgatgat gcatggttac tcaccactgc gatccccggg aaaacagcat tccaggtatt    6840
agaagaatat cctgattcag gtgaaaatat tgttgatgcg ctggcagtgt tcctgcgccg    6900
gttgcattcg attcctgttt gtaattgtcc ttttaacagc gatcgcgtat ttcgtctcgc    6960
tcaggcgcaa tcacgaatga ataacggttt ggttgatgcg agtgattttg atgacgagcg    7020
taatggctgg cctgttgaac aagtctggaa agaaatgcat aaacttttgc cattctcacc    7080
ggattcagtc gtcactcatg gtgatttctc acttgataac cttatttttg acgaggggaa    7140
attaataggt tgtattgatg ttggacgagt cggaatcgca gaccgatacc aggatcttgc    7200
catcctatgg aactgcctcg gtgagttttc tccttcatta cagaaacggc tttttcaaaa    7260
atatggtatt gataatcctg atatgaataa attgcagttt catttgatgc tcgatgagtt    7320
tttctaagaa ttaattcatg agcggataca tatttgaatg tatttagaaa aataaacaaa    7380
taggggttcc gcgcacattt ccccgaaaag tgccacctga aattgtaaac gttaatattt    7440
tgttaaaatt cgcgttaaat ttttgttaaa tcagctcatt ttttaaccaa taggccgaaa    7500
tcggcaaaat cccttataaa tcaaaagaat agaccgagat agggttgagt gttgttccag    7560
tttggaacaa gagtccacta ttaaagaacg tggactccaa cgtcaagggc gaaaaaccg    7620 tctatcaggg cgatggccca ctacgtgaac catcacccta atcaagtttt tggggtcga    7680 ggtgccgtaa agcactaaat cggaacccta agggagccc ccgatttaga gcttgacggg    7740
gaaagccggc gaacgtggcg agaaaggaag ggaagaaagc gaaaggagcg ggcgctaggg    7800
cgctggcaag tgtagcggtc acgctgcgcg taaccaccac acccgccgcg cttaatgcgc    7860
cgctacaggg cgcgtcccat tcgcca                                        7886
```

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic

```
                           6xHis tag

<400> SEQUENCE: 22

His His His His His His
1               5

<210> SEQ ID NO 23
<211> LENGTH: 774
<212> TYPE: DNA
<213> ORGANISM: Comamonas testosteroni

<400> SEQUENCE: 23
atgtccatca tcgtgataag cggctgcgcc accggcattg gtgcggctac gcgcaaggtc        60
ctggaggcgg ccggtcacca gatcgtaggc atcgatatac gcgatgcgga agtgattgcc       120
gatctctcga cggccgaagg tcgaaagcag gcgattgccg atgtactggc gaagtgcagc       180
aagggcatgg acggcctggt gctgtgcgcc ggcctgggac cgcagaccaa ggtgcttggc       240
aatgtggttt cggtcaatta ttttggcgcg accgagctga tggatgcctt tttgccagcg       300
ctgaaaaaag gccatcagcc cgcagccgtc gtcatctcgt ccgtggcttc cgcgcatctg       360
gcttttgaca agaacccact ggcgctggca ctggaagccg gcgaggaagc caaggcccgc       420
gccattgtcg aacatgcggg agagcagggc ggaaatctgg cctatgcggg cagcaagaat       480
gctttgacgg tggctgtgcg caaacgcgcc gccgcctggg gcgaggctgg cgtgcgcctg       540
aacaccatcg ccccoggtgc aaccgagact cccttgctgc aggcgggcct gcaggacccg       600
cgctatggcg aatccattgc caagttcgtt cctcccatgg gccgccgtgc cgagccgtcc       660
gagatggcgt cggtcatcgc cttttttgatg agcccggccg caagctatgt gcatggcgcg       720
cagatcgtca ttgatggcgg cattgatgcg gtgatgcgcc cgacacagtt ctga             774
```